(12) United States Patent
Martinez et al.

(10) Patent No.: US 11,629,350 B2
(45) Date of Patent: *Apr. 18, 2023

(54) SINGLE-VECTOR TYPE I VECTORS

(71) Applicant: SNIPR Biome ApS, Copenhagen Ø (DK)

(72) Inventors: Virginia Martinez, Copenhagen Ø (DK); Ruben Vazquez-Uribe, London (GB); Adam Takos, Copenhagen Ø (DK); Eric Van Der Helm, London (GB); Jasper Clube, London (GB)

(73) Assignee: SNIPR BIOME APS, Copenhagen Ø (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/166,941

(22) Filed: Feb. 3, 2021

(65) Prior Publication Data

US 2021/0163960 A1    Jun. 3, 2021

Related U.S. Application Data

(63) Continuation of application No. 16/201,736, filed on Nov. 27, 2018.

(30) Foreign Application Priority Data

Oct. 14, 2018 (GB) ..................... 1816700
Oct. 27, 2018 (GB) ..................... 1817509

(51) Int. Cl.
| | |
|---|---|
| *C12N 15/70* | (2006.01) |
| *C12N 9/22* | (2006.01) |
| *C12N 15/11* | (2006.01) |
| *A61K 38/46* | (2006.01) |
| *A61K 31/7088* | (2006.01) |
| *C07K 14/33* | (2006.01) |
| *A61P 31/04* | (2006.01) |

(52) U.S. Cl.
CPC .......... *C12N 15/70* (2013.01); *A61K 31/7088* (2013.01); *A61K 38/465* (2013.01); *A61P 31/04* (2018.01); *C07K 14/33* (2013.01); *C12N 9/22* (2013.01); *C12N 15/11* (2013.01); *C12N 2310/20* (2017.05); *C12N 2800/80* (2013.01); *C12N 2820/002* (2013.01); *C12N 2820/007* (2013.01); *C12N 2820/55* (2013.01); *C12N 2830/005* (2013.01)

(58) Field of Classification Search
CPC ....................................... C12N 15/70
See application file for complete search history.

(56) References Cited

U.S. PATENT DOCUMENTS

| | | |
|---|---|---|
| 4,626,504 A | 12/1986 | Puhler |
| 5,633,154 A | 5/1997 | Schaefer |
| 8,241,498 B2 | 8/2012 | Summer |
| 8,252,576 B2 | 8/2012 | Campbell |
| 8,906,682 B2 | 12/2014 | June |
| 8,911,993 B2 | 12/2014 | June |
| 8,916,381 B1 | 12/2014 | June |
| 8,975,071 B1 | 3/2015 | June |
| 9,101,584 B2 | 8/2015 | June |
| 9,102,760 B2 | 8/2015 | June |
| 9,102,761 B2 | 8/2015 | June |
| 9,113,616 B2 | 8/2015 | Stevens |
| 9,328,156 B2 | 5/2016 | June |
| 9,464,140 B2 | 10/2016 | June |
| 9,481,728 B2 | 11/2016 | June |
| 9,499,629 B2 | 11/2016 | June |
| 9,518,123 B2 | 12/2016 | June |
| 9,540,445 B2 | 1/2017 | June |
| 9,701,964 B2 | 7/2017 | Clube |
| 10,300,138 B2 | 5/2019 | Clube |
| 10,463,049 B2 | 11/2019 | Clube |
| 10,506,812 B2 | 12/2019 | Clube |
| 10,524,477 B2 | 1/2020 | Clube |
| 10,561,148 B2 | 2/2020 | Clube |
| 10,582,712 B2 | 3/2020 | Clube |
| 10,596,255 B2 | 3/2020 | Clube |
| 10,624,349 B2 | 4/2020 | Clube |
| 11,141,481 B2 | 10/2021 | Clube |
| 11,147,830 B2 | 10/2021 | Clube |
| 2004/0096974 A1 | 5/2004 | Herron |
| 2005/0118719 A1 | 6/2005 | Schmidt |
| 2011/0136688 A1 | 6/2011 | Scholl |
| 2013/0109053 A1 | 5/2013 | Macdonald |
| 2013/0287748 A1 | 10/2013 | June |
| 2013/0288368 A1 | 10/2013 | June |
| 2013/0309258 A1 | 11/2013 | June |
| 2014/0106449 A1 | 4/2014 | June |
| 2014/0107092 A1 | 4/2014 | Meyerson |
| 2014/0234972 A1 | 8/2014 | Zhang |

(Continued)

FOREIGN PATENT DOCUMENTS

| | | |
|---|---|---|
| CN | 107557378 A | 1/2018 |
| EP | 2840140 A1 | 2/2015 |

(Continued)

OTHER PUBLICATIONS

Mutalik et. al. Precise and reliable gene expression via standard transcription and translation initiation elements. 2013 Nature Methods, vol. 1-(4), pp. 354-360 (Year: 2013).*

Rolf Lutz and Hermann Bujard. Independent and tight regulation of transcriptional units in *Escherichia coli* via the LacR/O, the TetR/O and AraC/I1-I2 regulatory elements. Nucleic Acids Research, 1997, vol. 25, No. 6 1203-1210 (Year: 1997).*

(Continued)

*Primary Examiner* — Samuel C Woolwine
*Assistant Examiner* — Tiffany Nicole Grooms
(74) *Attorney, Agent, or Firm* — Morrison & Foerster LLP

(57) ABSTRACT

The invention relates to the production and use of Cas-encoding sequences and vectors comprising these. Aspects of the invention provide products, vectors, delivery vehicles, uses and methods for producing Cas-encoding sequences in bacterial or archaeal cells.

21 Claims, 6 Drawing Sheets

Specification includes a Sequence Listing.

(56) References Cited

U.S. PATENT DOCUMENTS

| | | |
|---|---|---|
| 2014/0370017 A1 | 12/2014 | June |
| 2015/0050699 A1 | 2/2015 | Siksnys |
| 2015/0050729 A1 | 2/2015 | June |
| 2015/0064138 A1 | 3/2015 | Lu |
| 2015/0093822 A1 | 4/2015 | June |
| 2015/0099299 A1 | 4/2015 | June |
| 2015/0118202 A1 | 4/2015 | June |
| 2015/0125463 A1 | 5/2015 | Cogswell |
| 2015/0132419 A1 | 5/2015 | Arvik |
| 2015/0139943 A1 | 5/2015 | Campana |
| 2015/0140001 A1 | 5/2015 | Lee |
| 2015/0290244 A1 | 10/2015 | June |
| 2016/0009805 A1 | 1/2016 | Kowanetz |
| 2016/0024510 A1 | 1/2016 | Bikard |
| 2016/0081314 A1 | 3/2016 | Thurston |
| 2016/0115488 A1 | 4/2016 | Zhang |
| 2016/0115489 A1 | 4/2016 | Zhang |
| 2016/0130355 A1 | 5/2016 | June |
| 2016/0159907 A1 | 6/2016 | June |
| 2016/0160186 A1 | 6/2016 | Parsley |
| 2016/0168594 A1 | 6/2016 | Zhang et al. |
| 2016/0194404 A1 | 7/2016 | June |
| 2016/0208012 A1 | 7/2016 | June |
| 2016/0324938 A1 | 11/2016 | Bikard |
| 2016/0333348 A1 | 11/2016 | Clube |
| 2016/0345578 A1 | 12/2016 | Barrangou |
| 2016/0347836 A1 | 12/2016 | Grosso |
| 2016/0354416 A1 | 12/2016 | Gajewski |
| 2017/0022499 A1 | 1/2017 | Lu |
| 2017/0173085 A1 | 6/2017 | Kovarik |
| 2017/0173086 A1* | 6/2017 | Boyle ................ A61K 35/741 |
| 2017/0175142 A1 | 6/2017 | Zhang |
| 2017/0196225 A1 | 7/2017 | Clube |
| 2017/0233708 A1* | 8/2017 | Liu .................... C12N 15/1037 |
| | | 435/219 |
| 2017/0246221 A1 | 8/2017 | Clube |
| 2017/0304443 A1 | 10/2017 | Lebwohl |
| 2017/0327582 A1 | 11/2017 | Bissonnette |
| 2017/0340733 A1 | 11/2017 | Cao |
| 2018/0015131 A1 | 1/2018 | Gajewski |
| 2018/0055852 A1 | 3/2018 | Kutok |
| 2018/0064114 A1 | 3/2018 | Clube |
| 2018/0064115 A1 | 3/2018 | Clube |
| 2018/0070594 A1 | 3/2018 | Clube |
| 2018/0084785 A1 | 3/2018 | Clube |
| 2018/0084786 A1 | 3/2018 | Clube |
| 2018/0140698 A1 | 5/2018 | Clube |
| 2018/0146681 A1 | 5/2018 | Clube |
| 2018/0155729 A1 | 6/2018 | Beisel |
| 2018/0179547 A1 | 6/2018 | Zhang |
| 2018/0200342 A1 | 7/2018 | Bikard |
| 2018/0273940 A1 | 9/2018 | Sommer |
| 2018/0303934 A1 | 10/2018 | Clube |
| 2018/0305714 A1* | 10/2018 | Maresca ............... C12N 15/79 |
| 2019/0133135 A1 | 5/2019 | Clube |
| 2019/0134194 A1 | 5/2019 | Clube |
| 2019/0160120 A1 | 5/2019 | Haaber |
| 2019/0230936 A1 | 8/2019 | Clube |
| 2019/0240325 A1 | 8/2019 | Clube |
| 2019/0240326 A1 | 8/2019 | Clube |
| 2019/0321468 A1 | 10/2019 | Clube |
| 2019/0321469 A1 | 10/2019 | Clube |
| 2019/0321470 A1 | 10/2019 | Clube |
| 2019/0367947 A1* | 12/2019 | Lopes Ferreira .... C12N 15/102 |
| 2020/0068901 A1 | 3/2020 | Clube |
| 2020/0077663 A1 | 3/2020 | Clube |
| 2020/0085066 A1 | 3/2020 | Clube |
| 2020/0102551 A1* | 4/2020 | Barrangou ........... C12N 15/102 |
| 2020/0115716 A1 | 4/2020 | Martinez |
| 2020/0121787 A1 | 4/2020 | Clube |
| 2020/0128832 A1 | 4/2020 | Clube |
| 2020/0164070 A1 | 5/2020 | Clube |
| 2020/0205416 A1 | 7/2020 | Clube |
| 2020/0254035 A1 | 8/2020 | Haaber |
| 2020/0267992 A1 | 8/2020 | Clube |
| 2020/0337313 A1 | 10/2020 | Clube |
| 2020/0390886 A1 | 12/2020 | Clube |
| 2021/0147827 A1 | 5/2021 | Clube |
| 2021/0147857 A1 | 5/2021 | Clube |
| 2021/0189406 A1 | 6/2021 | Martinez et al. |
| 2021/0230559 A1 | 7/2021 | Clube |
| 2021/0283167 A1 | 9/2021 | Clube |
| 2021/0386773 A1 | 12/2021 | Clube |

FOREIGN PATENT DOCUMENTS

| | | |
|---|---|---|
| EP | 3132035 B8 | 4/2020 |
| EP | 3132036 B8 | 4/2020 |
| EP | 3630975 A1 | 4/2020 |
| EP | 3633032 A2 | 4/2020 |
| EP | 3634442 A1 | 4/2020 |
| EP | 3634473 A1 | 4/2020 |
| RU | 2531343 C2 | 10/2014 |
| WO | 2005046579 A2 | 5/2005 |
| WO | 2005046579 A3 | 8/2005 |
| WO | 2007025097 A2 | 3/2007 |
| WO | 2008108989 A2 | 9/2008 |
| WO | 2010011961 A2 | 1/2010 |
| WO | 2010075424 A2 | 7/2010 |
| WO | 2012079000 A1 | 6/2012 |
| WO | 2012079000 A4 | 8/2012 |
| WO | 2012164565 A1 | 12/2012 |
| WO | 2013063361 A1 | 5/2013 |
| WO | 2013176772 A1 | 11/2013 |
| WO | 2014012001 A2 | 1/2014 |
| WO | 2014018423 A2 | 1/2014 |
| WO | 2014124226 A1 | 8/2014 |
| WO | 2015034872 A2 | 3/2015 |
| WO | 2014012001 A3 | 4/2015 |
| WO | 2015058018 A1 | 4/2015 |
| WO | 2015069682 A2 | 5/2015 |
| WO | 2015071474 A2 | 5/2015 |
| WO | 2015088643 A1 | 6/2015 |
| WO | 2015089419 A2 | 6/2015 |
| WO | 2015089419 A3 | 9/2015 |
| WO | 2015136541 A2 | 9/2015 |
| WO | 2015148680 A1 | 10/2015 |
| WO | 2015155686 A2 | 10/2015 |
| WO | 2015159068 A1 | 10/2015 |
| WO | 2015159086 A1 | 10/2015 |
| WO | 2015159087 A1 | 10/2015 |
| WO | 2015136541 A3 | 11/2015 |
| WO | 2016033088 A1 | 3/2016 |
| WO | 2016044745 A1 | 3/2016 |
| WO | 2016063263 A2 | 4/2016 |
| WO | 2016177682 A1 | 11/2016 |
| WO | 2016196361 A1 | 12/2016 |
| WO | 2016196605 A1 | 12/2016 |
| WO | 2017042347 A1 | 3/2017 |
| WO | 2017058751 A1 | 4/2017 |
| WO | 2017112620 A1 | 6/2017 |
| WO | 2017118598 A1 | 7/2017 |
| WO | 2018064165 A2 | 4/2018 |
| WO | 2018081502 A1 | 5/2018 |
| WO | 2018141907 A1 | 8/2018 |
| WO | 2018217351 A1 | 11/2018 |
| WO | 2018217981 A1 | 11/2018 |
| WO | 2018222969 A1 | 12/2018 |
| WO | 2018226853 A1 | 12/2018 |
| WO | 2019002207 A1 | 1/2019 |
| WO | 2019002218 A2 | 1/2019 |
| WO | 2020072248 A1 | 4/2020 |
| WO | 2020072250 A1 | 4/2020 |
| WO | 2020072253 A1 | 4/2020 |
| WO | 2020072254 A1 | 4/2020 |

OTHER PUBLICATIONS

Gomaa et al. Programmable Removal of Bacterial Strains by Use of Genome-Targeting CRISPR-Cas Systems (2014) MBio 5(1):e00928-00913 (Year: 2014).*

(56) References Cited

OTHER PUBLICATIONS

Vercoe et al. Cytotoxic Chromosomal Targeting by CRISPR/Cas Systems Can Reshape Bacterial Genomes and Expel or Remodel Pathogenicity Islands 2013 PLOS Genetics; vol. 9 | Issue 4 | e1003454 (Year: 2013).*
Aklujkar et al. (2010) "Interference With Histidyl-tRNA Synthetase by a CRISPR Spacer Sequence as a Factor in the Evolution of Pelobacter Carbinolicus," BMC Evolutionary Biology 10:203, 15 pages.
American Lung Association (2019). "Preventing COPD," retrieved from https://www.lung.org/lung-health-and-diseases/lung-disease-lookup/copd/symptoms-causes-risk-factors/preventing-copd.html, last visited Aug. 5, 2019, 1 page.
Anderson Catalog, retrieved from https//parts.igem.org/Promoters/Catalog/Anderson lasted visited Nov. 29, 2018, 2 pages.
Anderson Promotor Collection, BBa_J23100, (Aug. 4, 2006), 3 pages.
Anderson Promotor Collection, BBa_J23101, (Aug. 4, 2006), 2 pages.
Anderson Promotor Collection, BBa_J23102, (Aug. 4, 2006), 1 pages.
Anderson Promotor Collection, BBa_J23103, (Aug. 4, 2006), 2 pages.
Anderson Promotor Collection, BBa_J23104, (Aug. 4, 2006), 2 pages.
Anderson Promotor Collection, BBa_J23105, (Aug. 14, 2006), 2 pages.
Anderson Promotor Collection, BBa_J23106, (Aug. 14, 2006), 5 pages.
Anderson Promotor Collection, BBa_J23107, (Aug. 17, 2006), 1 pages.
Anderson Promotor Collection, BBa_J23108, (Aug. 17, 2006), 3 pages.
Anderson Promotor Collection, BBa_J23109, (Aug. 17, 2006), 2 pages.
Anderson Promotor Collection, BBa_J23110, (Aug. 17, 2006), 2 pages.
Anderson Promotor Collection, BBa_J23111, (Aug. 17, 2006), 1 pages.
Anderson Promotor Collection, BBa_J23112, (Aug. 17, 2006), 1 pages.
Anderson Promotor Collection, BBa_J23113, (Aug. 17, 2006), 1 pages.
Anderson Promotor Collection, BBa_J23114, (Aug. 17, 2006), 2 pages.
Anderson Promotor Collection, BBa_J23115, (Aug. 17, 2006), 1 pages.
Anderson Promotor Collection, BBa_J23116, (Aug. 17, 2006), 1 pages.
Anderson Promotor Collection, BBa_J23117, (Aug. 17, 2006), 1 pages.
Anderson Promotor Collection, BBa_J23118, (Aug. 17, 2006), 1 pages.
Anderson Promotor Collection, BBa_J23119, (Aug. 24, 2006), 3 pages.
Ang, Y.L.E. et al. (2015). "Best Practice in the Treatment of Advanced Squamous Cell Lung Cancer," Ther. Adv. Respir. Dis. 9(5):224-235.
Anonymous (Apr. 2016). "Checkpoint Inhibition: A Promising Immunotherapeutic Approach for Colorectal Cancer," Oncology, 5(3):1-5, retrieved from http//www.personalizedmedonc.com/publications/prno/april-2016-vol-5-no-3/checkpoint-inhibition-a-promising-irmunotherapeutic-approach-for-colorectal-cancer-2/, last visited Aug. 27, 2019, 5 pages.
Arnold, I.C. et al. (Apr. 8, 2015, e-pub. Mar. 4, 2015). "Helicobacter Hepaticus Infection in BALB/c Mice Abolishes Subunit-Vaccine-Induced Protection Against *M. tuberculosis*," Vaccine 33(15):1808-1814.

Arslan, Z. et al. (May 7, 2013). "RcsB-BglJ-Mediated Activation of Cascade Operon Does Not Induce the Maturation of CRISPR RNAs in *E. coli* K12," RNA Biology 10(5):708-715.
Arumugam et al. (May 12, 2011). "Enterotypes of the human gut microbiome," Nature 473(7346):174-180, 16 pages.
Barrangou, R. et al. (Mar. 2007). "CRISPR Provides Acquired Resistance Against Viruses in Prokaryotes," Science, 315:1709-1712.
Barrett, K.J. et al. (1976). "Interactions Between a Satellite Bacteriophage and Its Helper," J. Mol. Biol. 106:683-707.
Beisel, C.L. et al. (2014). "A CRISPR Design for Next-Generation Antimicrobials," Genome Biology 15:516, 4 pages.
Belizario, J.E. et al. (Oct. 6, 2015). "Human Microbiomes and Their Roles in Dysbiosis, Common Diseases, and Novel Therapeutic Approaches," Frontiers in Microbiology 6(1050):1-16.
Bikard, D. et al. (2013, e-pub. Jun. 12, 2013). "Programmable Repression and Activation of Bacterial Gene Expression Using an Engineered CRISPR-Cas System," Nucleic Acids Research 41(15):7429-7437.
Bikard, D. et al. (2017, e-pub. Sep. 6, 2017). "Using CRISPR-Cas Systems as Antimicrobials," Current Opinion in Microbiology 37:155-160.
Bikard, D. et al. (Aug. 16, 2012). "CRISPR Interference Can Prevent Natural Transformation and Virulence Acquisition during In Vivo Bacterial Infection," Cell Host & Microbe 12(2):177-186.
Bikard, D. et al. (Nov. 2014). "Development of Sequence-Specific Antimicrobials Based on Programmable CRISPR-Cas Nucleases," Nature Biotechnology 32(11):1146-1151, 16 pages.
Broaders, E. et al. (Jul./Aug. 2013). "Mobile Genetic Elements of the Human Gastrointestinal Tract," Gut Microbes 4(4):271-280.
Brouns, S.J.J. et al. (Aug. 15, 2008). Supplemental Material for "Small CRISPR RNAs Guide Antiviral Defense in Prokaryotes," Science 321:960-964.
Brouns, S.J.J. et al. (Aug. 15, 2008)."Small CRISPR RNAs Guide Antiviral Defense in Prokaryotes," Science 321:960-964.
Bryksin, A. V. et al. (Oct. 8, 2010). "Rational Design of a Plasmid Origin That Replicates Efficiently in Both Gram-Positive and Gram-Negative Bacteria," PloS One 5(10):e13244, 9 pages.
Bugrysheva, J.V. et al. (Jul. 2011, E-Pub. Apr. 29, 2011). "The Histone-Like Protein Hlp Is Essential for Growth of *Streptococcus pyogenes*: Comparison of Genetic Approaches to Study Essential Genes," Appl. Environ. Microbiol. 77(13):4422-4428.
Chan, B.K. et al. (2013). "Phage Cocktails and the Future of Phage Therapy," Future Microbiol. 8(6):769-783.
Chan, C.T.Y. et al. (Dec. 2015). "'Deadman' and 'Passcode' Microbial Kill Switches for Bacterial Containment," Nat. Chem. Biol. 12(2):82-86.
Chasteen, L. et al. (2006, e-pub. Nov. 6, 2006). "Eliminating Helper Phage From Phage Display," Nucleic Acids Research 34(21):e145, 11 pages.
Cheadle, E.J. et al. (2012). "Chimeric Antigen Receptors for T-Cell Based Therapy," Methods Mol. Biol. 907:645-666, 36 pages.
Christie, G.E. (1990). "Interactions Between Satellite Bacteriophage P4 and Its Helpers," Annu. Rev. Genet. 24:465-490.
Christie, G.E. (2012, e-pub. Nov. 3, 2012). "Pirates of the Caudovirales," Virology 434:210-221.
Citorik, R.J. et al. (Nov. 2014, e-pub Sep. 21, 2014). "Sequence-Specific Antimicrobials Using Efficiently Delivered RNA-Guided Nucleases," Nat. Biotechnol. 32(11):1141-1145, 18 pages.
Cochrane, K. et al. (2016, e-pub. Nov. 3, 2015). "Complete Genome Sequences and Analysis of the *Fusobacterium nucleatum* Subspecies *animalis* 7-1 Bacteripophage Φfunu1 and Φfunu2," Anaerobe 38:125-129. Abstract Only.
Coyne, M.J. et al. (2014). "Evidence of Extensive DNA Transfer between *Bacteroidales* Species Within the Human Gut," mBio 5(3):e01305-14, 12 pages.
De Filippo, C. et al. (Aug. 33, 2010). "Impact of Diet in Shaping Gut Microbiota Revealed by a Comparative Study in Children From Europe and Rural Africa," Proc. Natl. Acad. Sci. USA 107(33):14691-14696, 6 pages.
De Paepe, M. et al. (Mar. 28, 2014). "Bacteriophages: An Underestimated Role in Human and Animal Health?" Frontiers in Cellular and Infection Microbiology 4(39):1-11.

(56) References Cited

OTHER PUBLICATIONS

Deeks, E.D. (2014, e-pub. Jul. 15, 2014). "Nivolumab: A Review of Its Use in Patients With Malignant Melanoma," Drugs 74:1233-1239.

Deghorain, M. et al. (Nov. 23, 2012). "The Staphylococci Phages Family: An Overview," Viruses 4:3316-3335.

Dickson, R.P. et al. (Jan./Feb. 2017). "Bacterial Topography of the Healthy Human Lower Respiratory Tract," American Society for Microbiology 8(1):e02287-6, 12 pages.

Diez-Villasenor, C. et al. (May 2013). "CRISPR-Spacer Integration Reporter Plasmids Reveal Distinct Genuine Acquisition Specificities Among CROSPR-Cas 1-E Variants of *Escherichia coli*," RNA Biology 10(5):792-802.

Dutilh, B.E. et al. (Jul. 24, 2014). "A Highly Abundant Bacteriophage Discovered in the Unknown Sequences of Human Faecal Metagenomes," Nature Communications 5(4498):1-10.

Edgar et al. (Dec. 2010). "The *Escherichia coli* CRISPR System Protects From λ Lysogenization, Lysogens, and Prophage Induction," Journal of Bacteriology 192(23):6291-6294.

Ex Parte Re-Exam, mailed Dec. 10, 2018, for U.S. Appl. No. 90/014,184, filed Aug. 10, 2018, for U.S. Pat. No. Re. 9,701,964 102 pages.

Extended European Search Report, dated Mar. 6, 2020, for European Patent Application No. 190202999.99, 10 pages.

Final Office Action, dated May 29, 2020, for U.S. Appl. No. 16/201,736, filed Nov. 27, 2018, 10 pages.

Foca, A. et al. (2015, e-pub. Apr. 7, 2015). Gut Inflammation and Immunity: What Is the Role of the Human Gut Virome? Mediators of Inflammation 2015(326032):1-7.

Galperin, M.Y. (Dec. 2013). "Genome Diversity of Spore-Forming Firmicutes," Microbiology Spectrum 1(2):TBS-0015-2012, 27 pages.

Garon, E.B. et al. (Oct. 2015). "Current Perspectives in Immunotherapy for Non-Small Cell Lung Cancer," Seminars in Oncology 42(5 Supp. 2):S11-S18.

Garrett W.S. et al. (Oct. 5, 2007). "Communicable Ulcerative Colitis Induced by T-Bet Deficiency in the Innate Immune System," Cell 131(1):33-45, 23 pages.

Golubovskaya, V. et al. (Mar. 15, 2016). "Different Subsets of T Cells, Memory, Effector Functions, and CAR-T Immunotherapy," Cancers 8(36), 12 pages.

Gomaa et al. (Jan. 28, 2014). "Programmable Removal of Bacterial Strains by Use of Genome-Targeting CRISPR-Cas Systems," mBio, 5(1):e000928-13.

Gomaa, A.A. et al. (Jan./Feb. 2014). Supplemental Material to "Programmable Removal of Bacterial Strains by Use of GenomeTargeting CRISPR-Cas Systems," American Society for Microbiology 5(1):1-9.

Gudbergsdottir, S. et al. (2011, e-pub. Nov. 18, 2010). "Dynamic Properties of the Sulfolobus CRISPR/Cas and CRISPR/Cmr Systems When Challenged With Vector-Borne Viral and Plasmid Genes and Protospacers," Molecular Microbiology 79(1):35-49.

Guedan, S. et al. (Aug. 14, 2014). "ICOS-Based Chimeric Antigen Receptors Program Bipolar TH17/TH1 Cells," Blood 124(7):1070-1080.

Hargreaves, K.R. et al. (Aug. 26, 2014). "Abundant and Diverse Clustered Regularly Interspaced Short Palindromic Repeat Spacers in Clostridium difficile Strains and Prophages Target Multiple Phage Types within This Pathogen," mBio 5(5):e01045-13.

Harrington, L.E. (Nov. 2005, e-pub. Oct. 2, 2005). "Interleukin 17-producing CD4+ Effector T Cells Develop via a Lineage Distinct From the T Helper Type 1 and 2 Lineages," Nat. Immunol. 6(11):1123-1132.

Hooper, L.V. et al. (Jun. 8, 2012). "Interactions Between the Microbiota and the Immune System," Science 336(6086):1268-1273, 16 pages.

Horvath, P. et al. (2008, e-pub. Dec. 7, 2007). "Diversity, Activity, and Evolution of CRISPR Loci in *Streptococcus thermophiles*," Journal of Bacteriology 190(4):1401-1412.

Huddleston, J.R. (Jun. 20, 2014). "Horizontal Gene Transfer in the Human Gastrointestinal Tract: Potential Spread of Antibiotic Resistance Genes," Infection and Drug Resistance 7:167-176.

International Search Report and the Written Opinion of the International Searching Authority for PCT/EP2018/066954, dated Oct. 23, 2018, filed Jun. 25, 2018, 14 pages.

International Search Report for PCT/EP2016/059803, dated Jun. 30, 2016, filed May 3, 2016, 6 pages.

International Search Report for PCT/EP2018/082053, dated Mar. 14, 2019, filed Nov. 21, 2018, 9 pages.

International Search Report for PCT/EP2019/077760, dated Mar. 6, 2020, filed Oct. 14, 2019, 15 pages.

Ivanov, I.I. et al. (May 2010). "Segmented Filamentous Bacteria Take the Stage," Muscosal Immunol. 3(3):209-212, 7 pages.

Jiang, W. et al. (Nov. 2013). "Demonstration of CRISPR/Cas9/sgRNA-Mediated Targeted Gene Modification in *Arabidopsis*, Tobacco, Sorghum and Rice," Nucleic Acids Research 41(20):e188, 12 pages.

Jin, Y. et al. (2019, e-pub. Apr. 23, 2019). "The Diversity of Gut Microbiome is Associated With Favorable Responses to Anti-Programmed Death 1 Immunotherapy in Chinese Patients With NSCLC," Journal of Thoracic Oncology 14(8):1378-1389.

Jinek et al. (Aug. 17, 2012). "A Programmable Dual-RNA-Guided DNA Endonuclease in Adaptive Bacterial Immunity," Science 337(6096):816-821.

Kanhere, A. et al. (2005). Structural Properties of Promoters: Similarities and Differences Between Prokaryotes and Eukaryotes Nucleic Acids Research 33(10):3165-3175.

Khoja, L. et al. (2015). "Pembrolizumab," Journal for ImmunoTherapy of Cancer 3(36):1-13.

Kim, J.-S. (2016). "CRISPR/Cas9-Mediated Re-Sensitization of Antibiotic-Resistant *Escherichia coli* Harboring Extended-Spectrum β-Lactamases," Microbiol. Biotechnol. 26(2):394-401.

Kochenderfer, J.N. et al. (Sep. 2009). "Construction and Pre-clinical Evaluation of an Anti-CD19 Chimeric Antigen Receptor," J. Immunother. 32(7):689-702, 26 pages.

Kosiewicz, M.M. et al. (2014, e-pub. Mar. 26, 2014). "Relationship Between Gut Microbiota and Development of T Cell Associated Disease," FEBS Lett. 588:4195-4206.

Krom, R.J. et al. (Jul. 5, 2015). "Engineered Phagemids for Nonlytic, Targeted Antibacterial Therapies," Nano Letters 15(7):4808-4813.

Lim, H.N. et al. (Jun. 28, 2011, e-pub. Jun. 13, 2011). "Fundamental Relationship Between Operon Organization and Gene Expression," PNAS 108(26):10626-10631.

Lopez-Sanchez, M.-J. et al. (2012, e-pub. Jul. 27, 2012). "The Highly Dynamic CRISPR1 System of *Streptococcus agalactiae* Controls the Diversity of its Mobilome," Molecular Microbiology 85(6):1057-1071.

Ludwig, E.S. et al. (1985). "The Phylogenetic Position of *Streptococcus* and *Enterococcus*," Journal of General Microbiology 131:543-551.

Luo, M.L. et al. (2015, e-pub. Oct. 17, 2014). "Repurposing Endogenous Type I CRISPR-Cas Systems for Programmable Gene Repression," Nucleic Acids Research 43(1):674-681.

López, P. et al. (Apr. 5, 2016). "Th17 Responses and Natural IgM Antibodies Are Related to Gut Microbiota Composition in Systemic Lupus Erythematosus Patients," Sci. Rep. 6:24072, 12 pages.

Magee, M.S. et al. (Nov. 2014). "Challenges to Chimeric Antigen Receptor (CAR)-T Cell Therapy for Cancer," Discov. Med. 18(100):265-271, 6 pages.

Mahoney, K.M. et al. (2015). "The Next Immune-Checkpoint Inhibitors: PD-1/PD-L1 Blockade in Melanoma," Clinical Therapeutics 37(4):764-782.

Maikova, A. et al. (Jul. 31, 2018), "New Insights Into Functions and Possible Applications of Clostridium difficile CRISPR-Cas System," Frontiers in Microbiology 9(1740):1-8.

Majsec, K. et al. (2016). "Cas3 Is a Limiting Factor for CRISPR-Cas Immunity in *Escherichia coli* Cells Lacking H-NS," BMC Microbiology 16:28, 9 pages.

Makarova, J.S. et al. (Nov. 2015, e-pub. Sep. 28, 2015). "An Updated Evolutionary Classification of CRISPR-Cas Systems," Nature Rev. Microbiol. 13:722-736.

Makarova, K.S. et al. (2015). "Annotation and Classification of CRISPR-Cas Systems," Methods Mol. Biol. 1311:47-75, 27 pages.

(56) References Cited

OTHER PUBLICATIONS

Makarova, K.S. et al. (Feb. 27, 2017). "Snapshot: Class 1 CRISPR-Cas Systems," Cell 168(5):946, 2 pages.
Mancha-Agresti, P. et al. (Mar. 2017). "A New Broad Range Plasmid for DNA Delivery in Eukaryotic Cells Using Lactic Acid Bacteria: In Vitro and In Vivo Assays," Molecular Therapy: Methods & Clinical Development 4:83-91.
Manica, A. et al. (2011, e-pub. Mar. 8, 2011). "In vivo Activity of CRISPR-Mediated Virus Defence in a Hyperthermophilic Archaeon," Molecular Microbiology 80(2):481-491.
Marraffini, L.A. et al. (Dec. 19, 2008). "CRISPR Interference Limits Horizontal Gene Transfer in *Staphylococci* by Targeting DNA," Science 322(5909):1843-1845, 12 pages.
Mayo Clinic (2019). "Pulmonary Embolism," retrieved from https://www.nnayoclinic.org/diseases-conditions/pulnnonary-ennbolisnn/synnptonns-causes/syc-20354647, last visited Aug. 5, 2019, 8 pages.
Mayo Clinic (2020). "Infectious Diseases," retrieved from https://www.nnayoclinic.org/diseases-conditions/infectious-diseases/diagnosis-treatnnent/drc-20351179, last visited Jan. 17, 2020, 5 pages.
Mayo Clinic (2020). "Malaria," retrieved from https://www.nnayoclinic.org/diseases-conditions/nnalaria/diagnosis-treatnnent/drc-20351190, last visited Jan. 17, 2020, 3 pages.
Mayo Clinic (2020). "Sexually Transmitted Diseases (STDs)," retrieved from https://www.nnayoclinic.org/diseases-conditions/sexually-transnnitted-diseases-stds/diagnosis-treatnnent/drc-20351246, last visited Jan. 17, 2020, 5 pages.
Medina-Aparicio, L. et al. (May 2011, e-pub. Mar. 11, 2011). "The CRI SPR/Cas Immune System Is an Operon Regulated by LeuO, H-NS, and Leucine-Responsive Regulatory Protein in *Salmonella enterica* Serovar *typhi*," Journal of Bacteriology 193(10):2396-2407.
Mercenier, A. (1990). "Molecular Genetics of *Streptococcus thermophiles*," FEMS Microbiology Letters 87(1-2):61-77.
Mick, E. et al. (May 2013). "Holding a Grudge: Persisting Anti-Phage CRISPR Immunity in Multiple Human Gut Microbiomes," RNA Biology 10(5):900-906.
Mills, S. et al. (Jan./Feb. 2013). "Movers and Shakers: Influence of Bacteriophages in Shaping the Mammalian Gut Microbiota," Gut Microbes 4(1):4-16.
Moon, B.Y. et al. (Mar. 8, 2016). "Mobilization of Genomic Islands of *Staphylococcus aureus* by Temperate Bacteriophage," PLOS One 11(3):e0151409, 16 pages.
Mutalik, V.K. et al. (Apr. 2013, e-pub. Mar. 10, 2013) "Precise and Reliable Gene Expression via Standard Transcription and Translation Initiation Elements," Nat. Methods 10(4):354-360.
Nakamura, S. et al. (Nov. 2008). "Metagenomic Diagnosis of Bacterial Infections," Emerging Infectious Diseases 14(11):1784-1786.
Nale, J.Y. et al. (2012). "Diverse Temperate Bacteriophage Carriage in Clostridium Difficile 027 Strains," PloS One 7(5):e37263, 9 pages.
Navarre, L. et al. (2007). "Silencing of Xenogeneic DNA by H-NS-Facilitation of Lateral Gene Transfer in Bacteria by a Defense System That Recognizes Foreign DNA," Genes & Development 21:1456-1471.
Nelson, M.H. et al. (2015). "Harnessing the Microbiome to Enhance Cancer Immunotherapy," Journal of Immunology Research 2015:Article 368736, 12 pages.
Non-Final Office Action, dated Nov. 25, 2019, for U.S. Appl. No. 16/201,736, filed Nov. 27, 2018, 8 pages.
Non-Final Office Action, dated Nov. 30, 2020, for U.S. Appl. No. 16/201,736, filed Nov. 27, 2018, 35 pages.
Norris, J.S. et al. (2000). "Prokaryotic Gene Therapy to Combat Multidrug Resistant Bacterial Infection," Gene Therapy 7:723-725.
Novick, R. (May 18, 2018). "Reincarnation of a Staphylococcal Pathogenicity Island as an antibacterial Drone," 5th World Congress on Targeting Infectious Diseases: Targeting Phage & Antibiotic Resistance: Phage Therapy and Other Innovative Ideas.
Nowak, P. et al. (Nov. 28, 2015). "Gut Microbiota Diversity Predicts Immune Status in HIV-1 Infection," AIDS 29(18):2409-2418.
O'Hara, B.J. et al. (Jun. 8, 2017). "A Highly Specific Phage Defense System Is a Conserved Feature of the Vibrio cholera Mobilome," PLOS Genetics 13(6):e1006838, 17 pages.
Park, A. (Oct. 18, 2011). "A Surprising Link Between Bacteria and Colon Cancer," Cancer retrieved from http://healthlande.time.com/2011/10/18/a-surprising-link-between-bacteria-and-colon-cancer/, last visited Aug. 27, 2019, 3 pages.
Park, H. et al. (2005). "A Distinct Lineage Of CD4 T Cells Regulates Tissue Inflammation by Producing Interleukin 17," Nat. Immunol. 6(11):1133-1141, 24 pages.
Patterson, A.G. et al. (2017, e-pub. Mar. 27, 2017). "Regulation of CRISPR-Cas Adaptive Immune Systems," Current Opinion in Microbiology 37:1-7.
Pawluk, A. et al. (Apr. 15, 2014). "A New Group of Phage Anti-CRISPR Genes Inhibits the Type I-E CRISPR-Cas System of Pseudomonas aeruginosa," mBio. 5(2):e00896.
PCT Application No. PCT/EP2018/0071454.
Penades, J.R. et al. (Nov. 2015). "The Phage-Inducible Chromosomal Islands: A Family of Highly Evolved Molecular Parasites," Annual Review of Virology 2:181-201.
Pires, D.P. et al. (Sep. 2016, e-pub. Jun. 1, 2016). "Genetically Engineered Phages: A Review of Advances Over the Last Decade," Microbiology and Molecular Biology Reviews 80(3):523-543.
Pul, Ü. et al. (2010, e-pub. Feb. 17, 2010). "Identification and Characterization of *E. coli* CRISPR-cas Promoters and Their Silencing by H-NS," Molecular Microbiology 75(6):1495-1512.
Ram, G. et al. (Oct. 2, 2012). "Staphylococcal Pathogenicity Island Interference With Helper Phage Reproduction Is a Paradigm of Molecular Parasitism," Proc. Natl. Acad. Sci. USA 109(40):16300-16305.
Ramalingam, S.S. et al. (2014). "LB2-Metastatic Non-Small Cell Lung Cancer: Phase II Study of Nivolumab (Anti-PD-1, BMS-936558, ONO-4538) in Patients With Advanced, Refractory Squamous Non-Small Cell Lung Cancer," International Journal of Radiation Oncology Biology Physics Late Breaking Abstract (LB2).
Ran, F.A. et al. (Apr. 9, 2015). "In Vivo Genome Editing Using *Staphylococcus aureus* Cas9," Nature 570(7546):186-191, 28 pages.
Rashid, T. et al. (2013). "The Role of Klebsiella in Crohn's Disease With a Potential for the Use of Antimicrobial Measures," International Journal of Rheumatology 2013(Article ID 610393):1-9.
Request for Ex Parte Reexamination mailed Aug. 10, 2018, for U.S. Appl. No. 15/160,405, now U.S. Pat. No. 9,701,964, 42 pages.
Request for Ex Parte Reexamination mailed Nov. 1, 2018, for U.S. Appl. No. 15/160,405, now U.S. Pat. 9,701,964, 35 pages.
RFP Reporter, https://parts.igem.org/Part:BBa_J61022 lasted visited Nov. 29, 2018, 1 page.
Richter, C. et al. (2012, e-pub. Oct. 19, 2012). "Function and Regulation of Clustered Regularly Interspaced Short Palindromic Repeats (CRISPR) / CRISPR Associated (Cas) Systems," Viruses 4(12):2291-2311.
Ridaura, V.K. et al. (Sep. 6, 2013). "Cultured Gut Microbiota From Twins Discordant for Obesity Modulate Adiposity and Metabolic Phenotypes in Mice," Science 341(6150):1241214, 22 pages.
Roberts, A.P. et al. (Jun. 2009, e-pub. May 20, 2009). "A Modular Master on the Move: The Tn916 Family of Mobile Genetic Elements," Trends Microbiol. 17(6):251-258. Abstract Only.
Ryan, O.W. et al. (2014). "Multiplex Engineering of Industrial Yeast Genomes Using CRISPRm," Methods in Enzymology 546:473-489.
Samaržija, D. et al. (2001). "Taxonomy, Physiology and Growth of Lactococcus Lactis: A Review," Mljekarstvo 51(1):35-48.
Sapranauskas, R. et al. (Nov. 1, 2011, e-pub. Aug. 3, 2011). "The *Streptococcus thermophilus* CRISPR/Cas System Provides Immunity in *Escherichia coli*," Nucleic Acids Research 39(21):9275-9282.
Seed, K.D. et al. (Feb. 27, 2013). "A Bacteriophage Encodes Its Own CRISPR/Cas Adaptive Response to Evade Host Innate Immunity," Nature 494(7438):489-491.
Selle, K. et al. (Apr. 1, 2015). "Harnessing CRISPR-Cas Systems for Bacterial Genome Editing," Trends in Microbiology 23(4):225-232.

(56) References Cited

OTHER PUBLICATIONS

Sepsis Alliance. (Dec. 14, 2017). "What Are Vaccines," Retrieved from https://www.sepsis.org/sepsisand/prevention-vaccinations/; last visited Jul. 8, 2019, 3 pages.
Sepsis Alliance. (Jul. 8, 2019). "Prevention," Retrieved from https://www.sepsis.org/sepsisand/prevention/; accessed last visited Jul. 8, 2019, 5 pages.
Shoemaker, N.B. et al. (Feb. 2001). "Evidence for Extensive Resistance Gene Transfer Among *Bacteroides* spp. and Among *Bacteroides* and Other Genera in the Human Colon," Appl. Environ. Microbiol. 67(2):561-68.
Sivan, A. et al. (Nov. 27, 2015, e-pub Nov. 5, 2015). "Commensal Bifidobacterium Promotes Antitumor Immunity and Facilitates Anti-PD-L1 Efficacy," Science 350(6264):1084-1089, 13 pages.
Somkuti, G. A. et al. (Apr. 1988). "Genetic Transformation of *Streptococcus thermophilus* by Electroporation," Biochimie 70(4):579-585. Abstract Only.
Sorg, R. A. et al. (2014). "Gene Expression Platform for Synthetic Biology in the Human Pathogen *Streptococcus pneumoniae*," ACS Synthetic Biology 4(3):228-239. Abstract Only.
Soutourina, O.A. et al. (May 9, 2013). "Genome-Wide Identification of Regulatory RNAs in the Human Pathogen Clostridium difficile," PLos Genet. 9(5):e1003493, 20 pages.
Stern, A. et al. (2012). "CRISPR Targeting Reveals a Reservoir of Common Phages Associated With the Human Gut Microbiome," Genome Research 22(10):1985-1994.
Stern, A. et al. (Aug. 2010), Self-Targeting by CRISPR: Gene Regulation or Autoimmunity? Trends Genet. 26(8):335-340, 10 pages.
Stiefel, U. et al. (Aug. 2014, e-pub. May 27, 2014). "Gastrointestinal Colonization With a Cephalosporinase-Producing *Bacteroides* Species Preserves Colonization Resistance Against Vancomycin-Resistant Enterococcus and Clostridium Difficile in Cephalosporin-Treated Mice," Antimicrob. Agents Chemother. 58(8):4535-4542.
Stoebel, D.M. et al. (2008). "Anti-Silencing: Overcoming H-NS-Mediated Repression of Transcription in Gramnegative Enteric Bacteria," Microbiology 154:2533-2545.
Suvorov, A. (1988). "Transformation of Group A *Streptococci* by Electroporation," FEMS Microbiology Letters 56(1):95-100.
Takaishi, H. et al. (2008). "Imbalance in Intestinal Microflora Constitution Could Be Involved in the Pathogenesis of Inflammatory Bowel Disease," Int. J. Med. Microbiol.298:463-472.
Tan, J. (Dec. 17, 2015). "Immunotherapy Meets Microbiota," Cell 163:1561.
Topalian, S.L. et al. (Jun. 28, 2012). "Safety, Activity, and Immune Correlates of Anti-PD-1 Antibody in Cancer," N. Engl. J. Med. 366(26):2443-2454, 19 pages.
Tormo et al. (Apr. 2008). "*Staphylococcus aureus* Pathogenicity Island DNA Is Packaged in Particles Composed of Phage Proteins," Journal of Bacteriology 190(7):2434-2440.
Turnbaugh, P.J. et al. (Dec. 2006). "An Obesity-Associated Gut Microbiome With Increased Capacity for Energy Harvest," Nature 444:1027-1131.
U.S. Appl. No. 62/168,355, filed May 29, 2015, Barrangou, R. et al.
U.S. Appl. No. 62/296,853, filed Feb. 18, 2016, Barrangou, R. et al.
Uchiyama, J. et al. (2013, e-pub. Mar. 8, 2013). "Characterization of Helicobacter pylori Bacteriophage KHP30," Applied and Environmental Microbiology 79(10):3176-3184.
Veeranagouda, Y. et al. (Jun. 4, 2014). "Identification of Genes Required for the Survival of *B. fragilis* Using Massive Parallel Sequencing of a Saturated Transposon Mutant Library," BMC Genomics 15:429, 11 pages.
Vercoe, R.B. et al. (Apr. 18, 2013). "Cytotoxic Chromosomal Targeting by CRISPR/Cas Systems Can Reshape Bacterial Genomes and Expel or Remodel Pathogenicity Islands," PLOS Genetics 9(4):e1003454, 13 pages.
Villarino, N.F. et al. (Feb. 23, 2016, e-pub. Feb. 8, 2016). "Composition of the Gut Microbiota Modulates the Severity of Malaria," Proc. Natl. Acad. Sci. USA 113(8):2235-2240.

Vétizou, M. et al. (Nov. 27, 2015, e-pub Nov. 5, 2015). "Anticancer Immunotherapy by CTLA-4 Blockade Relies on the Gut Microbiota," Science 350(6264):1079-1084, 13 pages.
Walters, W.A. et al. (Nov. 17, 2014). "Meta-Analyses of Human Gut Microbes Associated With Obesity and IBD," FEBS Letters 588(22):4223-4233, 34 pages.
Wegmann, U. et al. (2007). "Complete Genome Sequence of the Prototype Lactic Acid Bacterium *Lactococcus lactis* Subsp. *cremoris* MG1363," Journal of Bacteriology, 189(8):3256-3270.
Wei, Y. et al. (2015, e-pub. Jan. 14, 2015). "Sequences Spanning the Leader-Repeat Junction Mediate CRISPR Adaptation to Phage in *Streptococcus thermophiles*," Nucleic Acids Research 43(3):1749-1758.
Westra, E.R. et al. (Sep. 1, 2010, e-pub. Aug. 18, 2010). "H-NS-Mediated Repression of CRISPR-Based Immunity in *Escherichia coli* K12 Can Be Relieved by the Transcription Activator LeuO," Molecular Microbiology 77(6):1380-1393.
Westwater, C. et al. (Apr. 2003). "Use of Genetically Engineered Phage to Deliver Antimicrobial Agents to Bacteria: An Alternative Therapy for Treatment of Bacterial Infections," Antimicrobial Agents and Chemotherapy 47(4):1301-1307.
Wexler, H.M. (Oct. 2007). "Bacteroides: the Good, the Bad, and the Nitty-Gritty," Clinical Microbiology Reviews 20(4):593-621.
Written Opinion for PCT Application No. PCT/EP2016/059803, dated Jun. 30, 2016, filed May 3, 2016, 6 pages.
Written Opinion for PCT/EP2018/082053, dated Mar. 14, 2019, filed Nov. 21, 2018, 6 pages.
Xie, Z. et al. (2013, e-pub. Aug. 9, 2013). "Development of a Tunable Wide-Range Gene Induction System Useful for the Study of Streptococcal Toxin-Antitoxin Systems," Applied and Environmental Microbiology 79(20):6375-6384.
Yang, C.-D. et al. (2014, e-pub. May 2, 2014). "CRP Represses the CRISPR/Cas System in *Escherichia coli*: Evidence That Endogenous CRISPR Spacers Impede Phage P1 Replication," Molecular Microbiology 92(5):1072-1091.
Yang, Y. et al. (Jun. 5, 2014, e-pub. Apr. 13, 2014). "Focused Specificity of Intestinal Th17 Cells Towards Commensal Bacterial Antigens," Nature 510(7503):152-156, 29 pages.
Yosef, I. et al. (2011). "High-Temperature Protein G Is Essential for Activity of the *Escherichia coli* Clustered Regularly Interspaced Palindromic Repeats (CRISPR)/Cas System," Proc. Natl. Acad. Sci. USA 108(50):20136-20141.
Zhang, X.Z. (2011). "Simple, Fast and High-Efficiency Transformation System for Directed Evolution of Cellulase in Bacillus Subtilis," Microbial Biotechnology 4(1):98-105.
Ziermann, R. et al. (1990). "Characterization of the cos Sites of Bacteriophages P2 and P4," Gene 96:9-15.
Zitvogel, L. et al. (Jan. 2015), "Cancer and the Gut Microbiota: An Unexpected Link," Sci. Transl. Med. 7(271):271ps1, 10 pages.
Bertram, R. et al. (2008). "The Application of Tet Repressor in Prokaryotic Gene Regulation and Expression," Microbial Biotechnology 1(1):1-6.
Chen, S. et al. (Feb. 2007, e-pub. Dec. 22, 2006). "Characterization of Strong Promoters From an Environmental Flavobacterium himemum Strain by Using a Green Fluorescent Protein-based Reporter System," Applied and Environmental Microbiology 73(4):1089-1100.
Extended European Search Report, dated May 10, 2021, for European Patent Application No. 20217137.7, 5 pages.
Lutz, R. et al. (1997). "Independent and Tight Regulation of Transcriptional Units in *Escherichia coli* via the LacR/O, the TetR/O and AraC/I1-I2 Regulatory elements," Nucleic Acids Research 25(6):1203-1210.
Nakade, S. et al. (2017, e-pub. Jan. 31, 2017). "Cas9, Cpf1 and C2c1/2/3—What's Next?" Bioengineered 8(3):265-273.
Petris, G. et al. (May 22, 2017). "Hit and Go CAS9 Delivered Through a Lentiviral Based Self-Limiting Circuit," Nature Communications 8:15334, 9 pages.
Yao, R. et al. (Sep. 2018). "CRISPR-Cas9/Cas 12a Biotechnology and Application in Bacteria," Synthetic and Systems Biotechnology 3(3):135-149.
Zhang, J. et al. (2019, e-pub. Jul. 30, 2019). "Drug Inducible CRISPR/Cas Systems," Computational and Structural Biotechnology Journal 17:1171-1177.

(56) References Cited

OTHER PUBLICATIONS

Leon, L.M. et al. (Apr. 2018). "How Bacteria Control the CRISPR-Cas Arsenal," Current Opinion in Microbiology 42:87-95, 17 pages.
Non-Final Office Action, dated Aug. 20, 2021, for U.S. Appl. No. 17/195,157, filed Mar. 8, 2021, 17 pages.
Tao, P. et al. (Feb. 14, 2018). "Unexpected Evolutionary Benefit to Phages Imparted by Bacterial CRISPR-Cas9," Sci. Adv. 4:eaar4134, 10 pages.
U.S. Appl. No. 17/105,392, Clube et al., filed Nov. 25, 2020.
Ungerer, J. et al. (Dec. 21, 2016). "Cpf1 Is a Versatile Tool for CRISPR Genome Editing Across Diverse Species of *Cyanobacteria*," Scientific Reports 6:39681, 9 pages.
Wendt, K.E. et al. (2016). "CRISPR/Cas9 Mediated Targeted Mutagenesis of the Fast Growing Cyanobacterium Synechococcus elongates UTEX 2973," Microbial Cell Factories 15:115, 8 pages.
Li, Q. et al. (2016, e-pub. May 23, 2016). "CRISPR-Based Genome Editing and Expression Control Systems in Clostridium acetobutylcum and Clostridium beijerinckii," Biotechnology Journal 11:961-972.
Xu, T. et al. (Jul. 2015). "Efficient Genome Editing in Clostridium cellulolyticum via CRISPR-Cas9 Nickase," Applied and Environmental Microbiology 81(13):4423-4431.

\* cited by examiner

SINGLE-VECTOR TYPE I VECTORS

CROSS-REFERENCE TO RELATED APPLICATIONS

This application is a continuation of U.S. patent application Ser. No. 16/201,736, filed Nov. 27, 2018 which claims priority to Great Britain Patent Application No. 1816700.7, filed Oct. 14, 2018, and Great Britain Patent Application No. 1817509.1, filed Oct. 27, 2018, the contents of each of which are hereby incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 786212000601SEQLIST.TXT, date recorded: Feb. 1, 2021, size: 23 KB).

TECHNICAL FIELD

The invention relates to the production and use of Cas-encoding sequences and vectors comprising these. Aspects of the invention provide products, vectors, delivery vehicles, uses and methods for producing Cas-encoding sequences in bacterial or archaeal cells.

BACKGROUND

The state of the art describes vectors and uses of these that employ CRISPR/Cas systems. For example, reference is made to WO2017/118598, US20180140698, US20170246221, US20180273940, US20160115488, US20180179547, US20170175142, US20160024510, US20150064138, US20170022499, US20160345578, US20180155729, US20180200342, WO2017112620, WO2018081502, PCT/EP2018/066954, PCT/EP2018/066980, PCT/EP2018/071454 and U.S. Ser. No. 15/985,658 and equivalent publications by the US Patent and Trademark Office (USPTO) or WIPO, the disclosures of which are incorporated herein by reference.

SUMMARY OF THE INVENTION

The invention provides the following configurations.

In a First Configuration A nucleic acid vector for introduction into a host cell, the vector comprising a first nucleotide sequence encoding a Type I Cas3 and a second nucleotide sequence encoding one or more Cascade proteins, wherein the first and second sequences are under the control of one or more promoters comprised by the vector for expression of the proteins in the cell.

In an example, the vector comprises an operon for expression in the cell of the Cas3 and Cascade proteins from a Cas module, the module comprising the nucleotide sequences encoding the Cas3 and Cascade proteins, and the operon comprising the Cas module under the control of a promoter for controlling the expression of both the Cas3 and Cascade proteins.

The invention also provides a delivery vehicle comprising the vector, as well as a pharmaceutical composition comprising the vector or vehicle and a pharmaceutically acceptable diluent, excipient or carrier.

The invention also provides a method of treating or reducing the risk of a disease or condition in a human or animal subject, the method comprising administering the vector, vehicle or composition to the subject, and introducing the vector into target host bacterial or archaeal cells in the subject (eg, in a gut microbiota, lung, eye or blood of the subject), wherein the Cas cuts (or otherwise modifies) one or more target sequences in the target cells and the cells are killed or growth or proliferation of the cells is reduced.

In a Second Configuration

A method of amplifying copies of a DNA encoding a functional Cas protein (optionally a Cas nuclease) in a bacterial or archaeal production strain of cells, the method comprising
(a) Providing production strain cells, each cell comprising a copy of said DNA, wherein each DNA comprises a nucleotide sequence encoding said Cas, wherein the nucleotide sequence is under the control of a promoter for controlling the expression of the Cas in the production strain cell, the DNA comprising an origin of replication that is operable in the cell for replication of the DNA;
(b) Culturing the cells to allow replication of the DNA, whereby the DNA is amplified; and
(c) Optionally isolating copies of the DNA,
Optionally wherein the promoter is an attenuated constitutive promoter.

In a Third Configuration

Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for enhancing the yield of amplified DNA produced by the production host cells.

In a Fourth Configuration

Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing toxicity of the Cas in the production strain.

In a Fifth Configuration

Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing mutation of the DNA (optionally the Cas-encoding sequence) in the production strain.

In a Sixth Configuration

Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for promoting production cell viability during the amplification of the DNA.

In a Seventh Configuration

Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing the occurrence of Cas cutting of DNA.

In an Eighth Configuration

A method for enhancing the yield of amplified copies of a DNA construct in a population of bacterial or archaeal production strain cells, wherein the construct comprises a nucleotide sequence encoding a functional Cas protein (optionally a Cas nuclease) that is under the control of a promoter, the method comprising culturing the cells to allow replication of the DNA thereby amplifying the DNA in the cells, wherein the promoter is an attenuated promoter.

In a Ninth Configuration

A method for reducing toxicity of a functional Cas protein (optionally a Cas nuclease) in a population of bacterial or archaeal production strain cells in a process of amplifying copies of a DNA construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated promoter.

In a Tenth Configuration

A method for reducing mutation of a DNA construct encoding a functional Cas protein (optionally a Cas nuclease) in a population of bacterial or archaeal production strain cells in a process of amplifying copies of the construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated promoter.

In an Eleventh Configuration

A method for promoting production cell viability of a population of bacterial or archaeal production strain cells in a process of amplifying copies of a DNA construct comprised by the cells, wherein the construct comprises a nucleotide sequence encoding a functional Cas protein (optionally a Cas nuclease) and the sequence is under the control of a promoter, the method comprising culturing the cells to allow replication of the DNA thereby amplifying the DNA in the cells, wherein the promoter is an attenuated promoter.

In a Twelfth Configuration

A method for reducing the occurrence of Cas nuclease cutting of a DNA construct in a population of bacterial or archaeal production strain cells in a process of amplifying copies of the construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated promoter.

BRIEF DESCRIPTION OF THE DRAWINGS

(FIG. 1A) Layout of the CRISPR Guided Vector™, CGV™. Plasmid 1: pSC101 or pBAD promoter (induced by arabinose), cas3 and cascade genes. Plasmid 2: pCloDF13 ori, pTac promoter (induced by IPTG), CRISPR array. (FIG. 1B) Dilution series ($10^1$-$10^6$) of drop spots (5 µl) of *E. coli* MG1655 harboring the CGV on LB agar plates with and without inducers. (FIG. 1C) CRISPR induction killed 99.9% of the population (grey bar). Growth in absence of induction is shown in black. CGV™ refers to a CRISPR Guided Vector™, which is a nucleic acid vector comprising nucleotide sequences encoding CRISPR/Cas components.

(FIG. 2A) Layout of the CRISPR Guided Vector™, CGV™. pSC101 or pTac promoter (induced by IPTG), CRISPR array, pBAD promoter (induced by arabinose), cas3 and cascade genes. (FIG. 2B) Dilution series ($10^1$-$10^6$) of drop spots (5 µl) of *E. coli* MG1655 harboring the CGV on SM agar plates with and without inducers. (FIG. 2C) CRISPR induction killed 99% of the population (grey bar). Growth in absence of induction is shown in black. CGV™ refers to a CRISPR Guided Vector™, which is a nucleic acid vector comprising nucleotide sequences encoding CRISPR/Cas components.

(FIG. 3A) CRISPR induction killed 99% of the population in 60 minutes (dashed line). Growth in absence of induction is shown in black lines. CRISPR/Cas was induced at time-point 0 and monitored until 120 minutes. (FIG. 3B) Dilution series ($10^1$-$10^6$) of drop spots (5 µl) on SM agar plates of *E. coli* MG1655 after 60 minutes of induction.

(FIG. 4A) Bacteria count of a synthetic population composed of three different strains. CRISPR was induced at time-point 0 and monitored for 60 minutes. Growth in absence of induction is shown in black. CRISPR induction prompted 1-$\log_{10}$ reduction in viable cells of target strain *E. coli* MG1655, while leaving *E. coli* Top10 and *L. lactis* NZ9000 populations intact (dark grey bars). (FIG. 4B) Dilution series ($10^1$-$10^6$) of drop spots (5 µl) of the bacterial community mixture after 60 minutes of induction. *E. coli* MG1655 grows selectively on BHI+ streptomycin, *E. coli* Top10 on ampicillin, and *L. lactis* NZ9000 on chloramphenicol.

(FIG. 5A) CRISPR induction generated 4-$\log_{10}$ reductions in viable cells of target strain *E. coli* MG1655, both in the pure culture and in the community mixture (grey bars). Growth in absence of induction is shown in black. (FIG. 5B) Dilution series of a pure culture of *E. coli* MG1655 and the bacterial community mixture on streptomycin plates with and without inducers.

(FIG. 6A) Dilution series ($10^1$-$10^6$) of drop spots (5 µl) of *E. coli* MG1655 harboring the CGV on SM agar plates with and without inducers. (FIG. 6B) CRISPR induction killed 99% of the population (grey bar). Growth in absence of induction is shown in black. CGV™ refers to a CRISPR Guided Vector™ which is a nucleic acid vector comprising nucleotide sequences encoding CRISPR/Cas components.

DETAILED DESCRIPTION

Figure 1A:
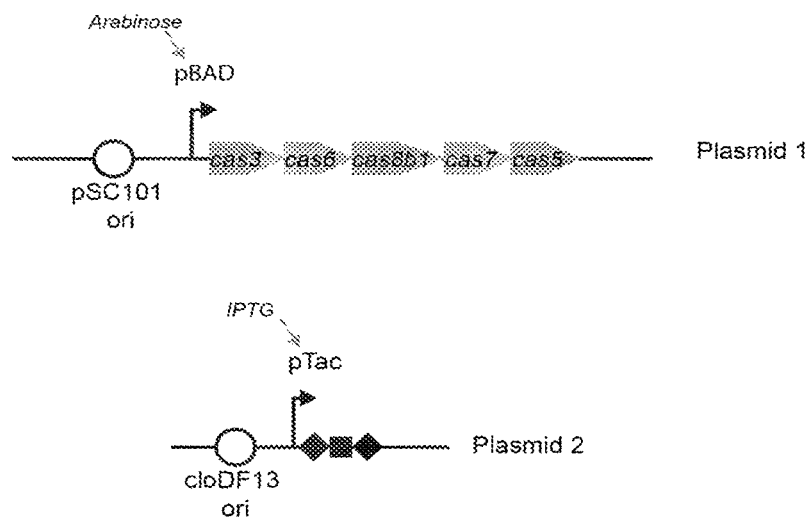
FIGS. 1A-1C. Type I CRISPR-Cas system of *C. difficile* targeting *E. coli* MG1655.

The invention relates to the production and use of Cas-encoding sequences and vectors comprising these. Aspects of the invention provide products, vectors, delivery vehicles, uses and methods for producing Cas-encoding sequences in bacterial or archaeal cells.

An aspect of the invention provides for the control of expression of Cas and optionally also Cascade proteins from single vectors, such as by regulated use of Cas modules in an operon and/or using attenuated promoters.

Concepts:

An aspect of the invention provides nucleic acid vectors that are useful for introducing into target host cells of any eukaryotic or prokaryotic species (eg, ex vivo or in vitro) for expressing Type I Cas and optionally other components of a Type I CRISPR/Cas system. Usefully, the vector may in some examples therefore provide a single-vector means for introducing a complete exogenous Type I CRISPR/Cas system into a target cell for modification (eg, cutting by Cas3) of DNA in the target cell. In an example, a chromosomal target sequence (ie, protospacer that is cognate with the Cas3) is modified. In another example, an episomal DNA sequence is modified, for example a plasmid sequence or a DNA that has been introduced into the cell. The latter may be useful in a recombineering method of the invention wherein exogenous DNA in the target cell is cut by the Cas3 and optionally this produces one or more recombinogenic ends for recombination of the cut DNA with a further DNA of interest, thereby producing a recombination product in the cell. For example, in such a recombineering method, the target cell is a recombinogenic *E coli* cell, eg, comprising a red/ET system. In another example, the target cell is an undesired cell (eg, a cell of a species or strain that is pathogenic to humans or animals, such as a bacterial disease-causing species or strain) and the cutting by Cas3 kills the cell. This may be useful for treating or preventing an infection in a human or animal harbouring target cells. The provision of single-vector means that express minimally a Cas endonuclease (eg, Cas3), cognate accessory proteins (eg, Cascade proteins) and at least one CRISPR array (or nucleotide sequence encoding a guide RNA (eg, a single guide RNA)), wherein the Cas, accessory proteins and array (or nucleotide sequence) comprise a functional CRISPR/Cas system is more convenient and the inventors believe more efficient for introducing into a target cell and effecting CRISPR/Cas modification of a target sequence therein than the use of 2 or 3 or more separate vectors (eg, a vector encoding the Cas nuclease and a different vector encoding the accessory proteins, and possibly a further vector comprising the array (or gRNA-encoding nucleotide sequence) which all need to transform the target cell for the system to function). This may provide one or more benefits, therefore, such as simplifying delivery (and thus the design of delivery vehicles), simplifying construction of the vector and vehicle and/or providing for better cutting or killing efficiencies. Conveniently, an example of the invention therefore uses an operon for the coordinated expression in the target cells of the Cas and accessory proteins (and optionally also the array or gRNA-encoding sequence(s)). Whilst not wishing to be bound by any particular theory, the introduction of a single vector (eg, using an operon) as per the invention may advantageously coordinate the expression of the Cas and accessory proteins (and optionally production of cRNAs or gRNAs) so that these are available to operate together without undue delay in the target cell. This may be important to tip the balance between, on the one hand the target cell using its endogenous anti-restriction, endogenous Cas or other endogenous mechanisms that seek out and degrade invading phage and DNA, and on the other hand efficient cell killing or deactivation of such mechanisms by the invading CRISPR components of the vector of the invention. In such an arms race, concerted and early operation of the CRISPR components in the cell are likely to be important to gain the upper hand and effect cell killing. The invention provides means to assist this.

By way of example, the invention thus provides the following Concepts:—

1. A nucleic acid vector for introduction into a host cell, the vector comprising a first nucleotide sequence encoding a Type I Cas3 and a second nucleotide sequence encoding one or more Cascade proteins, wherein the first and second sequences are under the control of one or more promoters comprised by the vector for expression of the proteins in the cell.

2. The vector of concept 1, wherein the vector comprises an operon for expression in the cell of the Cas3 and Cascade proteins from a Cas module, the module comprising the nucleotide sequences encoding the Cas3 and Cascade proteins, and the operon comprising the Cas module under the control of a promoter for controlling the expression of both the Cas3 and Cascade proteins.

3. The vector of concept 2, wherein
   (a) the first sequence is between the promoter and the second sequence in the operon;
   (b) the operon comprises no Cas-encoding nucleotide sequences between the promoter and the first nucleotide sequence; and/or
   (c) the operon comprises (in 5' to 3' direction) the promoter, the first sequence and the second sequence.

4. The vector of any preceding concept, wherein each promoter is a constitutive promoter.

5. The vector of any one of concepts 1 to 3, wherein the promoter is repressible (optionally repressible by a tetracycline repressor or lac repressor).

6. The vector of any one of concepts 1 to 3, wherein the promoter is inducible.

7. The vector of any preceding concept, wherein the first sequence is under the control of a medium strength promoter.

8. The vector of any preceding concept, wherein the first sequence is under the control of a promoter that has an Anderson Score (AS) of 0.5>AS>0.1.

9. The vector of any preceding concept, wherein the first sequence (and optionally the second sequence) is under the control of a promoter and translation initiation site (TIS) combination that is capable of producing expression of green fluorescent protein (GFP) from a first expression operating unit (EOU) in *E. coli* strain BW25113 cells with a fluorescence of from 0.5 to 4 times the fluorescence produced in *E. coli* strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.

10. The vector of concept 9, wherein fluorescence using the first EOU is 0.5 to 2 times the fluorescence using the second EOU.

11. The vector of any preceding concept, wherein the vector comprises an origin of replication that is operable in the host cell.

12. The vector of any preceding concept, wherein the vector comprises an origin of replication that is operable in a bacterial cell of a vector production strain, wherein the Cas3 is not operable in the production strain cell to target and cut a chromosomal sequence thereof.
13. The vector of concept 12, wherein the first sequence is under the control of a promoter that is capable of controlling expression of the Cas3 at a level that is not toxic to the production strain cell.
14. The vector of any preceding concept, wherein the vector is a high copy number vector.
15. The vector of any preceding concept, wherein the first nucleotide sequence or operon is comprised by a mobile genetic element.
16. The vector of any preceding concept, wherein the vector is devoid of a Cas adaption module.
17. The vector of any preceding concept, wherein the vector is devoid of nucleotide sequence encoding one, more or all of a Cas1, Cast, Cas4, Cas6, Cas7 and Cas 8.
18. The vector of any preceding concept, wherein the vector comprises (optionally in 5' to 3' direction) nucleotide sequence encoding one, more or all of Cas11, Cas7 and Cas8a1.
19. The vector of concept 18, wherein the vector comprises nucleotide sequence encoding Cas3' and/or Cas3".
20. The vector or concept 19, wherein the nucleotide sequences encoding the Cas3' and/or Cas3" are between the promoter and the sequence(s) recited in concept 18.
21. The vector of any one of concepts 18 to 20, wherein the host cell comprises a Type IA CRISPR array that is cognate with the Cas3.
22. The vector of any one of concepts 18 to 20, wherein the host cell comprises an endogenous Type TB, C, U, D, E or F CRISPR/Cas system.
23. The vector of any one of concepts 1 to 17, wherein the vector comprises (optionally in 5' to 3' direction) nucleotide sequence encoding one, more or all of Cas8b1, Cas7 and Cas5.
24. The vector of concept 23, wherein the vector comprises a nucleotide sequence encoding Cas3 between the promoter and the sequence(s) recited in concept 23.
25. The vector of concept 23 or 24, wherein the host cell comprises a Type IB CRISPR array that is cognate with the Cas3.
26. The vector of concept 23 or 24, wherein the host cell comprises an endogenous Type IA, C, U, D, E or F CRISPR/Cas system.
27. The vector of any one of concepts 1 to 17, wherein the vector comprises (optionally in 5' to 3' direction) nucleotide sequence encoding one, more or all of Cas5, Cas8c and Cas7.
28. The vector of concept 27, wherein the vector comprises a nucleotide sequence encoding Cas3 between the promoter and the sequence(s) recited in concept 27.
29. The vector of concept 27 or 28, wherein the host cell comprises a Type IC CRISPR array that is cognate with the Cas3.
30. The vector of concept 27 or 28, wherein the host cell comprises an endogenous Type IA, B, U, D, E or F CRISPR/Cas system.
31. The vector of any one of concepts 1 to 17, wherein the vector comprises (optionally in 5' to 3' direction) nucleotide sequence encoding one, more or all of Cas8U2, Cas7, Cas5 and Cas6.
32. The vector of concept 31, wherein the vector comprises a nucleotide sequence encoding Cas3 between the promoter and the sequence(s) recited in concept 31.
33. The vector of concept 31 or 32, wherein the host cell comprises a Type IU CRISPR array that is cognate with the Cas3.
34. The vector of concept 31 or 32, wherein the host cell comprises an endogenous Type IA, B, C, D, E or F CRISPR/Cas system.
35. The vector of any one of concepts 1 to 17, wherein the vector comprises (optionally in 5' to 3' direction) nucleotide sequence encoding one, more or all of Cas10d, Cas7 and Cas5.
36. The vector of concept 35, wherein the vector comprises a nucleotide sequence encoding Cas3' and/or Cas3".
37. The vector of concept 36, wherein the nucleotide sequences encoding the Cas3' and/or Cas3" are between the promoter and the sequence(s) recited in concept 35.
38. The vector of any one of concepts 35 to 37, wherein the host cell comprises a Type ID CRISPR array that is cognate with the Cas3.
39. The vector of any one of concepts 35 to 37, wherein the host cell comprises an endogenous Type IA, B, C, U, E or F CRISPR/Cas system.
40. The vector of any one of concepts 1 to 17, wherein the vector comprises (optionally in 5' to 3' direction) nucleotide sequence encoding one, more or all of Cas8e, Cas11, Cas7, Cas5 and Cas6.
41. The vector of concept 40, wherein the vector comprises a nucleotide sequence encoding Cas3 between the promoter and the sequence(s) recited in concept 40.
42. The vector of concept 40 or 41, wherein the host cell comprises a Type IE CRISPR array that is cognate with the Cas3.
43. The vector of concept 40 or 41, wherein the host cell comprises an endogenous Type IA, B, C, D, U or F CRISPR/Cas system.
44. The vector of any one of concepts 1 to 17, wherein the vector comprises (optionally in 5' to 3' direction) nucleotide sequence encoding one, more or all of Cas8f, Cas5, Cas7 and Cas6f.
45. The vector of concept 44, wherein the vector comprises a nucleotide sequence encoding Cas3 between the promoter and the sequence(s) recited in concept 44, wherein the vector is devoid of nucleotide sequence encoding further Cas between the promoter and the sequence encoding the Cas3.
46. The vector of concept 44 or 45, wherein the host cell comprises a Type IF CRISPR array that is cognate with the Cas3.
47. The vector of concept 44 or 45, wherein the host cell comprises an endogenous Type IA, B, C, D, U or E CRISPR/Cas system.
48. The vector of any one of concepts 1 to 17, wherein the Cas and Cascade are
  (a) Type IA Cas and Cascade proteins;
  (b) Type IB Cas and Cascade proteins;
  (c) Type IC Cas and Cascade proteins;
  (d) Type ID Cas and Cascade proteins;
  (e) Type IE Cas and Cascade proteins;
  (f) Type IF Cas and Cascade proteins; or
  (g) Type IU Cas and Cascade proteins.
49. The vector of any preceding concept, wherein the Cas and Cascade are *E coli* (optionally Type IE or IF) Cas and Cascade proteins.
50. The vector of concept 49, wherein the *E coli* is ESBL-producing *E. coli* or *E. coli* ST131-O25b:H4.
51. The vector of any preceding concept, wherein the Cas and Cascade are
  (a) *Clostridium* (eg, *C dificile*) Cas and Cascade proteins, optionally *C dificile* resistant to one or more antibiotics selected from aminoglycosides, lincomycin, tetracyclines, erythromycin, clindamycin, penicillins, cephalosporins and fluoroquinolones;
(b) *Pseudomonas aeruginosa* Cas and Cascade proteins, optionally *P aeruginosa* resistant to one or more antibiotics selected from carbapenems, aminoglycosides, cefepime, ceftazidime, fluoroquinolones, piperacillin and tazobactam; or
(c) *Klebsiella pneumoniae* (eg, carbapenem-resistant *Klebsiella pneumoniae* or Extended-Spectrum Beta-Lactamase (ESBL)-producing *K pneumoniae*) Cas and Cascade proteins.
52. The vector of any preceding concept, wherein the Cas and Cascade are *E coli, C difficile, P aeruginosa, K pneumoniae, P furiosus* or *B halodurans* Cas and Cascade proteins.
53. The vector of any preceding concept, wherein the Cas3 is a Cas3 of a CRISPR/Cas locus of a first bacterial or archaeal species, wherein the distance between the Cas3-encoding sequence of the locus and its cognate promoter is further than the distance between the Cas3-encoding sequence and the respective promoter comprised by the vector.
54. The vector of any preceding concept, wherein the distance between the promoter and the Cas3-encoding sequence and/or Cascade protein-encoding sequence(s) is shorter than in a corresponding wild-type Type I locus.
55. The vector of any preceding concept, wherein the vector comprises (i) a CRISPR array for producing crRNAs in the host cell and/or (ii) one or more nucleotide sequences encoding one or more guide RNAs (gRNAs or single gRNAs), wherein the crRNAs or gRNAs are cognate to the Cas3 (and optionally cognate to the Cascade proteins).
56. The vector of concept 55 when dependent from concept 2, wherein the array or gRNA-encoding sequence(s) are comprised by the operon and under the control of the promoter.
57. The vector of concept 56, wherein the array or gRNA-encoding sequence(s) are under the control of a promoter that is different from the promoter that controls the expression of the Cas3.
58. The vector of concept 56 or 57, wherein one or more of the crRNAs or gRNAs comprises a spacer sequence that is capable of hybridising to a target nucleotide sequence of the host cell, wherein the target sequence is adjacent a PAM, the PAM being cognate to the Cas3.
59. The vector of concept 58, wherein the target sequence is a chromosomal sequence of the host cell.
60. The vector of concept 58 or 59, wherein the Cas3 is operable to cut the target sequence.
61. The vector of any preceding concept, wherein the vector is a plasmid or phagemid.
62. A delivery vehicle comprising the vector of any preceding concept, wherein the delivery vehicle is capable of delivering the vector into the host cell.
63. The vehicle of concept 62, wherein the delivery vehicle is a phage, non-replicative transduction particle, nanoparticle carrier, bacterium or liposome.
64. The vector or vehicle of any preceding concept, wherein the host cell is a bacterial or archaeal cell, optionally, the host cell is a *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cell.
65. The vector or vehicle of any preceding concept for administration to a human or animal subject for treating or reducing the risk of a disease or condition in the subject.
66. The vector or vehicle of concept 65, wherein the disease or condition is an infection of the subject with host cells (eg, bacterial cells), or wherein the disease or condition is mediated by host cells (eg, bacterial cells).
67. A pharmaceutical composition comprising the vector or vehicle of any preceding concept and a pharmaceutically acceptable diluent, excipient or carrier.
68. A method of treating or reducing the risk of a disease or condition in a human or animal subject, the method comprising administering the vector, vehicle or composition of any preceding concept to the subject, and introducing the vector into target host bacterial or archaeal cells in the subject (eg, in a gut microbiota, lung, eye or blood of the subject), wherein the Cas cuts (or otherwise modifies) one or more target sequences in the target cells and the cells are killed or growth or proliferation of the cells is reduced.
69. The method of concept 68, wherein the target cells are cells of a disease pathogen species.
70. The method of concept 68 or 69, wherein the target cells are *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cells.

Embodiments

An aspect of the invention provides improved ways of amplifying DNA constructs in bacterial and archaeal production strain cells. For example, the DNA may be a high copy number plasmid or phagemid comprising a constitutive promoter for controlling the expression of one or more Cas proteins when the DNA has been introduced into a target host bacterial or host cell. It is desirable, according to an aspect of the invention, to consider attenuating the promoter activity during amplification of the DNA in the production strain. This is useful, since the inventors have found that Cas expression in production strains may be toxic to production strain cells, thereby reducing the yield of amplified DNA. Toxicity may be due, for example, to off-target cutting of the production strain chromosomal DNA when the Cas is a nuclease (such as Cas9 or Cas3) and/or due to relatively high levels of expression of the Cas in the cells. Additionally or alternatively, undesirably the Cas expression or activity may impose a selective pressure that favours mutation and propagation of mutated DNA constructs (such as mutation in one more or all of a CRISPR/Cas operon, Cas-encoding gene, Cascade-encoding gene, CRISPR array and gRNa-encoding sequence of the DNA construct) in production cells, thereby reducing the yield of desired amplified constructs and imposing an undesired step of separating desired from mutated DNA constructs for further formulation into useful compositions. Such compositions may be pharmaceutical compositions, herbicides, pesticides, environmental remediation compositions etc. In one example, the promoter attenuation in production strains is achieved by using a medium strength (not high or low) promoter to control the Cas-encoding nucleotide sequence of the DNA constructs. A medium level of Cas expression may be tolerable in the production strains, and yet once the DNA is subsequently introduced into target host cells the Cas is expressed at sufficiently high levels to produce desired activity to modify (eg, cut) target sequences in target cells. In an alternative, the invention uses a repressible promoter, wherein the promoter is repressed in production strain, but not repressed in target host cells. For example, aspects of the invention use a tetracycline repressor (tetR) expressed in production strain cells that represses the promoter.

Thus, the yield can be enhanced by one or more of
(a) reducing toxicity of the Cas in the production strain;
(b) reducing mutation of the DNA (optionally the Cas-encoding sequence) in the production strain;
(c) promoting production cell viability during the amplification of the DNA; and
(d) reducing the occurrence of Cas cutting of DNA (optionally cutting of production host cell chromosomal DNA or said DNA construct).

To this end, the invention provides Embodiments as follows:—

1. A method of amplifying copies of a DNA encoding a functional Cas protein (optionally a Cas nuclease) in a bacterial or archaeal production strain of cells, the method comprising
   (a) Providing production strain cells, each cell comprising a copy of said DNA, wherein each DNA comprises a nucleotide sequence encoding said Cas, wherein the nucleotide sequence is under the control of a promoter for controlling the expression of the Cas in the production strain cell, the DNA comprising an origin of replication that is operable in the cell for replication of the DNA;
   (b) Culturing the cells to allow replication of the DNA, whereby the DNA is amplified; and
   (c) Optionally isolating copies of the DNA,
   wherein the promoter is an attenuated constitutive promoter.

In an example, promoter is a medium strength promoter. In another example, the promoter is repressed in the production strain cell. Hence, the promoter is an attenuated promoter in these examples.

2. Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for enhancing the yield of amplified DNA produced by the production host cells.

3. The use of paragraph 2, wherein the use is for enhancing said yield by
   (a) reducing toxicity of the Cas in the production strain;
   (b) reducing mutation of the DNA (optionally the Cas-encoding sequence) in the production strain;
   (c) promoting production cell viability during the amplification of the DNA; and/or
   (d) reducing the occurrence of Cas cutting of DNA (optionally cutting of production host cell chromosomal DNA or said DNA construct).

4. Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing toxicity of the Cas in the production strain.

5. Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing mutation of the DNA (optionally the Cas-encoding sequence) in the production strain.

6. Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for promoting production cell viability during the amplification of the DNA.

7. Use of an attenuated promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing the occurrence of Cas cutting of DNA.

8. A method for enhancing the yield of amplified copies of a DNA construct in a population of bacterial or archaeal production strain cells, wherein the construct comprises a nucleotide sequence encoding a functional Cas protein (optionally a Cas nuclease) that is under the control of a promoter, the method comprising culturing the cells to allow replication of the DNA thereby amplifying the DNA in the cells, wherein the promoter is an attenuated promoter.

9. A method for reducing toxicity of a functional Cas protein (optionally a Cas nuclease) in a population of bacterial or archaeal production strain cells in a process of amplifying copies of a DNA construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated promoter.

10. A method for reducing mutation of a DNA construct encoding a functional Cas protein (optionally a Cas nuclease) in a population of bacterial or archaeal production strain cells in a process of amplifying copies of the construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated promoter.

11. A method for promoting production cell viability of a population of bacterial or archaeal production strain cells in a process of amplifying copies of a DNA construct comprised by the cells, wherein the construct comprises a nucleotide sequence encoding a functional Cas protein (optionally a Cas nuclease) and the sequence is under the control of a promoter, the method comprising culturing the cells to allow replication of the DNA thereby amplifying the DNA in the cells, wherein the promoter is an attenuated promoter.

12. A method for reducing the occurrence of Cas nuclease cutting of a DNA construct in a population of bacterial or archaeal production strain cells in a process of amplifying copies of the construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated promoter.

13. The use of paragraph 5 or 7, or the method of paragraph 10 or 12, wherein the mutation or cutting is mutation or cutting of host cell chromosomal DNA or the construct DNA.

14. The method or use of any one of paragraphs 2 to 13, wherein the promoter is a constitutive promoter.

15. The method or use of any preceding paragraph, wherein the promoter is repressed in the production strain cells (optionally repressed by a tetracycline repressor or a lac repressor).

16. The method or use of paragraph 15, wherein the promoter is $P_{LtetO-1}$, $P_{Llaco-1}$ or a repressible homologue thereof.

Other examples of suitable repressible promoters are Ptac (repressed by lad) and he Leftward promoter (pL) of phage lambda (which repressed by the λcI repressor). In an example, the promoter comprises a repressible operator (eg, tetO or lacO) fused to a promoter sequence. The corresponding repressor is encoded by a nucleic acid in the production strain (eg, a chromosomally-integrated sequence or a sequence comprised by an episome) and the repressor is expressed during the DNA or vector amplification method of the invention, whereby the promoter controlling Cas expression is repressed. In delivery vehicles that are subsequently produced from isolated amplified DNA/vector, the vehicle is devoid of an expressible nucleotide sequence encoding the repressor, whereby the promoter is functional when the DNA/vector is introduced into a target host cell. For example, in the absence of the repressor the promoter is constitutively ON for expression of the Cas. The system is therefore primed to work once the DNA/vector is introduced into the host cells, and this effect can be enhanced further by using a high copy number DNA/vector comprising an origin of replication that is operable in the host cell. A high copy number vector or DNA is also desirable in the production strain cells for enhancing yield of the DNA/vector, and by use of an attenuated promoter as described herein (eg, medium strength promoter and/or repressed promoter in the production strain cells) one can minimise Cas toxicity whilst culturing to maximise amplification and thus yield of the DNA/vector.

17. The method or use of any preceding paragraph, wherein the promoter is a medium strength promoter.

18. The method or use of any preceding paragraph, wherein the promoter has an Anderson Score (AS) of 0.5>AS>0.1.

19. The method or use of any preceding paragraph, wherein the nucleotide sequence encoding said Cas is under the control of a promoter and translation initiation site (TIS) combination that is capable of producing expression of green fluorescent protein (GFP) from a first expression operating unit (EOU) in *E. coli* strain BW25113 cells with a fluorescence of from 0.5 to 4 times the fluorescence produced in *E. coli* strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.

20. The method or use of paragraph 19, wherein fluorescence using the first EOU is 0.5 to 2 times the fluorescence using the second EOU.

21. The method or use of any preceding paragraph, wherein the nuclease is Cas3 and optionally the DNA or cell encodes cognate Cascade proteins.

22. The method or use of any one of paragraphs 1 to 20, wherein the Cas is a Cas9.

23. The method or use of any preceding paragraph, wherein the production strain cells comprise a helper phage genome that is inducible to produce phage coat proteins in the cells, wherein the method further comprises inducing production of the phage proteins and causing packaging of the amplified DNA into phage particles or non-self-replicative transduction particles, and further isolating the phage or transduction particles and optionally formulating the particles into a pharmaceutical composition for administration to a human or animal subject for treating or reducing the risk of a disease or condition in the subject.

24. The method or use of paragraph 23, wherein the particles are capable of infecting target host cells in the subject and transducing the cells with the DNA, wherein the Cas and crRNAs (or guide RNAs, gRNAs) encoded by the DNA are expressed in the cells, the crRNAs or (gRNAs) being operable to guide the Cas to a target nucleotide sequence (optionally a chromosomal sequence) comprised by the cells, wherein the Cas cuts the target sequences in the cells, thereby killing host cells and treating or reducing the risk of the disease or condition.

25. The method or use of paragraph 24, wherein the host cells are bacterial or archaeal cells, optionally, the host cells are *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cells.

26. The method or use of any preceding paragraph, wherein each DNA is comprised by a high copy number plasmid or phagemid.

27. The method or use of any preceding paragraph, wherein the DNA construct comprises one or more nucleotide sequences for producing crRNAs or gRNAs that are operable for Cas nuclease targeting in target host cells.

Paragraphs & Generally Applicable Features:

The invention provides the following Paragraphs, which are supported by the Examples below. Any features of the Concepts are combinable with any features of the Embodiments. Any features of the Concepts are combinable with any features of the Embodiments. Any features of the Paragraphs are combinable with any features of the Embodiments.

Any cell herein (eg, a production strain cell or target host cell) may be a bacterial cell, archaeal cell, algal cell, fungal cell, protozoan cell, invertebrate cell, vertebrate cell, fish cell, bird cell, mammal cell, companion animal cell, dog cell, cat cell, horse cell, mouse cell, rat cell, rabbit cell, eukaryotic cell, prokaryotic cell, human cell, animal cell, rodent cell, insect cell or plant cell. Preferably, the cell is a bacterial cell. Alternatively, the cell is a human cell. Optionally, the production strain cell(s) and target host cell(s) are of the same phylum, order, family, genus, species or strain.

1. A nucleic acid vector for introduction into a host cell, the vector comprising a first nucleotide sequence encoding a Type I Cas3, wherein the sequence is under the control of a promoter comprised by the vector for expression of the Cas3 in the cell.

In an example, the vector is a DNA vector, eg, ssDNA vector or dsDNA vector.

2. The vector of paragraph 1, wherein the vector comprises a second nucleotide sequence encoding one or more Cascade proteins, wherein the first and second sequences are under the control of one or more promoters comprised by the vector for expression of the proteins in the cell.

3. The vector of paragraph 2, wherein the Cascade protein(s) are cognate with the Cas3.

In an example, the Cas3 is cognate with Cascade proteins encoded by the host cell and/or encoded by a second operon. Optionally, the second operon is comprised by the vector. Optionally, the second operon is comprised by a second vector that is capable of introducing the second operon into the host cell, whereby the Cas3 and Cascade proteins are expressed from the operons in the host cell and are operable with crRNA or gRNA to target the Cas to a host cell target sequence, wherein the Cas3 is capable of modifying the target sequence.

4. The vector of paragraph 2 or 3, wherein the vector comprises an operon for expression in the cell of the Cas3 and Cascade proteins from a Cas module, the module comprising the nucleotide sequences encoding the Cas3 and Cascade proteins, and the operon comprising the Cas module under the control of a promoter for controlling the expression of both the Cas3 and Cascade proteins.

The term "operon" is known to the skilled person such as relating to a functioning unit of DNA containing at least expressible 2 nucleotide sequences respectively encoding for an expression product (eg, a respective translatable mRNA), wherein the sequences are under common promoter control.

5. The vector of paragraph 4, wherein the first sequence is between the promoter and the second sequence in the operon.

6. The vector of paragraph 4 or 5, wherein the operon comprises no Cas-encoding nucleotide sequences between the promoter and the first nucleotide sequence.

Optionally, the Cas3 is a Cas3 encoded by a CRISPR/Cas locus of a first bacterial or archaeal species, wherein in the locus the Cas3-encoding sequence is 3' of Cascade protein-encoding sequences (ie, the latter are between the Cas3 and the 5'-most promoter of the locus).

Optionally, the Cas3 is a ygcB protein (eg, wherein the production strain cell and/or host target cell is an $E\ coli$).
Optionally, the Cascade proteins comprise or consist of
cas5 (casD, csy2)
cas6 (cas6f, cse3, casE)
cas7 (csc2, csy3, cse4, casC)
cas8 (casA, cas8a1, cas8b1, cas8c, cas10d, cas8e, cse1, cas8f, csy1).

Optionally herein the promoter and the Cas3-encoding sequence are spaced no more than 150, 100, 50, 40, 30, 20 or 10 bp apart, eg, from 30-45, or 30-40, or 39 or around 39 bp apart.

Optionally herein a ribosome binding site and the Cas3-encoding sequence are spaced no more than 20, 15, 14, 13, 12, 11, 10, 9, 8, 7, 6, 4 or 3 bp apart, eg, from 10-5, 6 or around 6 bp apart.

7. The vector of any one of paragraphs 4 to 6, wherein the operon comprises (in 5' to 3' direction) the promoter, the first sequence and the second sequence.

8. The vector of any preceding paragraph, wherein each promoter is a constitutive promoter.

9. The vector of any one of paragraphs 1 to 7, wherein the promoter is repressible (optionally repressible by a tetracycline repressor or lac repressor).

10. The vector of any one of paragraphs 1 to 7, wherein the promoter is inducible.

11. The vector of any preceding paragraph, wherein the first sequence is under the control of a weak promoter.

12. The vector of any one of paragraphs 1 to 7, wherein the first sequence is under the control of a medium strength promoter.

13. The vector of any one of paragraphs 1 to 7, wherein the first sequence is under the control of a strong promoter.

In an example, the promoter is in combination with a Shine-Dalgarno sequence comprising the sequence 5'-aaagaggagaaa-3' (SEQ ID NO: 5) or a ribosome binding site homologue thereof.

14. The vector of any one of paragraphs 1 to 7, wherein the first sequence is under the control of a promoter that has an Anderson Score (AS) of AS>0.5.

See Table 2 for more information on Anderson Scores in relation to promoters.

15. The vector of any one of paragraphs 1 to 7, wherein the first sequence is under the control of a promoter that has an Anderson Score (AS) of 0.5>AS>0.1.

16. The vector of any one of paragraphs 1 to 7, wherein the first sequence is under the control of a promoter that has an Anderson Score (AS) of <0.1.

17. The vector of any one of paragraphs 1 to 7, wherein the first sequence (and optionally the second sequence) is under the control of a promoter and translation initiation site (TIS) combination that is capable of producing expression of green fluorescent protein (GFP) from a first expression operating unit (EOU) in $E.\ coli$ strain BW25113 cells with a fluorescence of from 0.5 to 4 times the fluorescence produced in $E.\ coli$ strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.

18. The vector of paragraph 17, wherein fluorescence using the first EOU is 0.5 to 2 times the fluorescence using the second EOU.

For example, fluorescence using the first EOU is 0.5 to X times the fluorescence using the second EOU, wherein X is from 3.0 to 1.0, eg, 3, 2.5, 2, 1.5 or 1, wherein fluorescence is determined using excitation at 481 nm and emission at 507 nm. Optionally, $E\ coli$ cultures at OD600 of 0.3-0.5 in the exponential growth phase are used.

For example, the upstream insulator, the nucleotide sequence encoding GFP, 3' UTR, transcription terminator and downstream insulator of each EOU are as disclosed in Mutalik et al (2013). For example, the upstream insulator, the nucleotide sequence encoding GFP, 3' UTR, transcription terminator and downstream insulator of each EOU are corresponding sequences of SEQ ID NO: 4. For example, the $E\ coli$ is $E.\ coli$ BW25113 is grown in MOPS EZ Rich Medium (Teknova) supplemented with 50 µg/ml kanamycin (kan) at 37° C., shaken at 900 r.p.m. For example, each EOUs is comprised by a medium copy plasmid, eg, a plasmid derived from pFAB217 comprising a p15A replication origin and a kan resistance gene.

19. The vector of any preceding paragraph, wherein the vector comprises an origin of replication that is operable in the host cell.

20. The vector of any preceding paragraph, wherein the vector comprises an origin of replication that is operable in a bacterial cell of a vector production strain, wherein the Cas3 is not operable in the production strain cell to target and cut a chromosomal sequence thereof.

An example of a production strain cell is an *E coli* cell. A production strain cell is a cell that is used to amplify DNA encoding Cas (and optionally other components of a CRISPR/Cas system). Usefully, the strain may package the amplified DNA into transduction particles that are may be isolated to produce a composition that can be contacted with a population of target host cells (eg, bacterial, archaeal, prokaryotic, eukaryotic, human, animal, mammal, rodent, mouse, rat, rabbit, *Xenopus*, fish, bird, amphibian, insect, plant, amoeba or algae cells) wherein the DNA is introduced into the cells for expression of the Cas (and optional other CRISPR/Cas system components), wherein the Cas is guided to a protospacer target sequence in the host cells and modifies (eg, cuts) the sequence. In another example, the amplified DNA isolated from a population of production strain cells and is combined with a delivery vehicle (eg, a carrier bacterium, nanoparticle or liposome), wherein the delivery vehicle can be contacted with a population of target host cells (eg, bacterial, archaeal, prokaryotic, eukaryotic, human, animal, mammal, rodent, mouse, rat, rabbit, *Xenopus*, fish, bird, amphibian, insect, plant, amoeba or algae cells) wherein the DNA is introduced into the cells for expression of the Cas (and optional other CRISPR/Cas system components), wherein the Cas is guided to a protospacer target sequence in the host cells and modifies (eg, cuts) the sequence.

21. The vector of paragraph 20, wherein the first sequence is under the control of a promoter that is capable of controlling expression of the Cas3 at a level that is not toxic to the production strain cell.

In an example, substantially no production strain cells are killed when the Cas3-encoding sequence is amplified therein. In another example, no more than 40, 30, 20, 10, 5, 4, 3, 2, or 1% of production strain cells are killed when the Cas3-encoding sequence is amplified therein. For example this is in a 1, 2, 3, 4, 5, 6, 7, 8 9 10, 12 or 24 hour period of culturing the cells.

22. The vector of paragraph 20, wherein the first sequence is under the control of a promoter that controls expression of the Cas3 in the production strain cell such that the cell is capable of growth and propagation sufficient to produce at least 1000 copies of the vector.

For example this is in a 1, 2, 3, 4, 5, 6, 7, 8 9 10, 12 or 24 hour period of culturing the cells. For example, at least $10^4$, $10^5$, $10^6$, $10^7$, $10^8$, $10^9$, $10^{10}$, $10^{11}$, $10^{12}$, $10^{13}$, $101^4$, $10^{15}$, $10^{16}$, $10^{17}$ or $10^{18}$ copies of the vector are produced per $10^3$, $10^4$, $10^5$, $10^6$, $10^7$, $10^8$, $10^9$, $10^{10}$, $10^{11}$, $10^{12}$, $10^{13}$, $101^4$, $10^{15}$, $10^{16}$, $10^{17}$ production strain cells respectively.

23. The vector of any one of paragraphs 20 to 22, wherein the cell is capable of at least 2 or 3 logs of expansion when the vector is comprised therein.

For example, this is in a 1, 2, 3, 4, 5, 6, 7, 8 9 10, 12 or 24 hour period of culturing the cells.

24. The vector of any preceding paragraph, wherein the vector is a high copy number vector.

25. The vector of any preceding paragraph, wherein the first nucleotide sequence or operon is comprised by a mobile genetic element.

Suitable mobile genetic elements, eg, transposons, are disclosed in WO2016177682 and US20170246221, the disclosures of which are explicitly incorporated herein for possible use in the invention and for providing one or more features for the claims herein.

26. The vector of any preceding paragraph, wherein the vector is devoid of a Cas adaption module. For example, the vector is devoid of nucleotide sequences encoding a Cas1, Cas2 and/or Cas4.

27. The vector of any preceding paragraph, wherein the vector is devoid of nucleotide sequence encoding one, more or all of a Cas1, Cas2, Cas4, Cas6 (optionally Cas6f), Cas7 and Cas 8 (optionally Cas8f).

28. The vector of any preceding paragraph, wherein the vector is devoid of a sequence encoding a Cas6 (optionally a Cas6f).

29. The vector of any one of paragraphs 1 to 27, wherein the module encodes a Cas6 (optionally a Cas6f).

30. The vector of any preceding paragraph, wherein the vector comprises (optionally in 5' to 3' direction) nucleotide sequence encoding one, more or all of Cas11, Cas7 and Cas8a1.

31. The vector of paragraph 30, wherein the vector comprises nucleotide sequence encoding Cas3' and/or Cas3" (optionally wherein the nucleotide sequences encoding the Cas3' and/or Cas3" are between the promoter and the sequence(s) recited in paragraph 30).

In one embodiment, the vector comprises nucleotide sequences (in 5' to 3' direction) that encode a Cas3 (eg, Cas3' and/or Cas3"), Cas11, Cas7 and Cas8a1. Optionally, a nucleotide sequence encoding Cas6 is between the Cas3 sequence(s) and the Cas11 sequence. Optionally, the vector comprises a Type IA CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

32. The vector of paragraph 30 or 31, wherein the host cell comprises a Type IA CRISPR array that is cognate with the Cas3.

33. The vector of paragraph 30 or 31, wherein the host cell comprises an endogenous Type IB, C, U, D, E or F CRISPR/Cas system.

34. The vector of any one of paragraphs 1 to 29, wherein the vector comprises (optionally in 5' to 3' direction) nucleotide sequence encoding one, more or all of Cas8b1, Cas7 and Cas5.

35. The vector of paragraph 34, wherein the vector comprises a nucleotide sequence encoding Cas3 between the promoter and the sequence(s) recited in paragraph 34.

In one embodiment, the vector comprises nucleotide sequences (in 5' to 3' direction) that encode a Cas3, Cas8b1, Cas7 and Cas5. Optionally, a nucleotide sequence encoding Cas6 is between the Cas3 sequence(s) and the Cas8b1 sequence. Optionally, the vector comprises a Type IB CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

36. The vector of paragraph 34 or 35, wherein the host cell comprises a Type IB CRISPR array that is cognate with the Cas3.
37. The vector of paragraph 34 or 35, wherein the host cell comprises an endogenous Type IA, C, U, D, E or F CRISPR/Cas system.
38. The vector of any one of paragraphs 1 to 29, wherein the vector comprises (optionally in 5' to 3' direction) nucleotide sequence encoding one, more or all of Cas5, Cas8c and Cas7.
39. The vector of paragraph 38, wherein the vector comprises a nucleotide sequence encoding Cas3 between the promoter and the sequence(s) recited in paragraph 38.

In one embodiment, the vector comprises nucleotide sequences (in 5' to 3' direction) that encode a Cas3, Cas5, Cas8c and Cas7. Optionally, a nucleotide sequence encoding Cas6 is between the Cas3 sequence(s) and the Cas5 sequence. Optionally, the vector comprises a Type IC CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

40. The vector of paragraph 38 or 39, wherein the host cell comprises a Type IC CRISPR array that is cognate with the Cas3.
41. The vector of paragraph 38 or 39, wherein the host cell comprises an endogenous Type IA, B, U, D, E or F CRISPR/Cas system.
42. The vector of any one of paragraphs 1 to 29, wherein the vector comprises (optionally in 5' to 3' direction) nucleotide sequence encoding one, more or all of Cas8U2, Cas7, Cas5 and Cas6.
43. The vector of paragraph 42, wherein the vector comprises a nucleotide sequence encoding Cas3 between the promoter and the sequence(s) recited in paragraph 42.

In one embodiment, the vector comprises nucleotide sequences (in 5' to 3' direction) that encode a Cas3, Cas8U2, Cas7, Cas5 and Cas6. Optionally, a nucleotide sequence encoding Cas6 is between the Cas3 sequence(s) and the Cas8U2 sequence. Optionally, the vector comprises a Type IU CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

44. The vector of paragraph 42 or 43, wherein the host cell comprises a Type IU CRISPR array that is cognate with the Cas3.
45. The vector of paragraph 42 or 43, wherein the host cell comprises an endogenous Type IA, B, C, D, E or F CRISPR/Cas system.
46. The vector of any one of paragraphs 1 to 29, wherein the vector comprises (optionally in 5' to 3' direction) nucleotide sequence encoding one, more or all of Cas10d, Cas7 and Cas5.
47. The vector of paragraph 46, wherein the vector comprises a nucleotide sequence encoding Cas3' and/or Cas3" (optionally wherein the nucleotide sequences encoding the Cas3' and/or Cas3" are between the promoter and the sequence(s) recited in paragraph 46).

In one embodiment, the vector comprises nucleotide sequences (in 5' to 3' direction) that encode a Cas3, Cas10d, Cas7 and Cas5. Optionally, a nucleotide sequence encoding Cas6 is between the Cas3 sequence(s) and the Cas10d sequence. Optionally, the vector comprises a Type ID CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

48. The vector of paragraph 46 or 47, wherein the host cell comprises a Type ID CRISPR array that is cognate with the Cas3.
49. The vector of paragraph 46 or 47, wherein the host cell comprises an endogenous Type IA, B, C, U, E or F CRISPR/Cas system.
50. The vector of any one of paragraphs 1 to 29, wherein the vector comprises (optionally in 5' to 3' direction) nucleotide sequence encoding one, more or all of Cas8e, Cas11, Cas7, Cas5 and Cas6.
51. The vector of paragraph 50, wherein the vector comprises a nucleotide sequence encoding Cas3 between the promoter and the sequence(s) recited in paragraph 50.

In one embodiment, the vector comprises nucleotide sequences (in 5' to 3' direction) that encode a Cas3, Cas8e, Cas11, Cas7, Cas5 and Cas6. Optionally, a nucleotide sequence encoding Cas6 is between the Cas3 sequence(s) and the Cas11 sequence. Optionally, the vector comprises a Type IE CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

52. The vector of paragraph 50 or 51, wherein the host cell comprises a Type IE CRISPR array that is cognate with the Cas3.

53. The vector of paragraph 50 or 51, wherein the host cell comprises an endogenous Type IA, B, C, D, U or F CRISPR/Cas system.
54. The vector of any one of paragraphs 1 to 29, wherein the vector comprises (optionally in 5' to 3' direction) nucleotide sequence encoding one, more or all of Cas8f, Cas5, Cas7 and Cas6f.
55. The vector of paragraph 54, wherein the vector comprises a nucleotide sequence encoding Cas3 between the promoter and the sequence(s) recited in paragraph 54, wherein the vector is devoid of nucleotide sequence encoding further Cas between the promoter and the sequence encoding the Cas3.

In one embodiment, the vector comprises nucleotide sequences (in 5' to 3' direction) that encode a Cas3, Cas8f, Cas5, Cas7 and Cas6f. Optionally, a nucleotide sequence encoding Cas6 is between the Cas3 sequence(s) and the Cas8f sequence. Optionally, the vector comprises a Type IF CRISPR array or one or more nucleotide sequences encoding single guide RNA(s) (gRNA(s)), wherein the array and each gRNA comprises repeat sequence that is cognate with the Cas3. Thus, the array is operable in a host cell when the vector has been introduced into the cell for production of guide RNAs, wherein the guide RNAs are operable with the Cas and Cascade proteins to target and modify (eg, cut) a target nucleotide sequence in the host cell, optionally thereby killing the host cell. Similarly, the single guide RNAs encoded by the vector in one embodiment are operable with the Cas and Cascade proteins to target and modify (eg, cut) a target nucleotide sequence in the host cell, optionally thereby killing the host cell.

56. The vector of paragraph 54 or 55, wherein the host cell comprises a Type IF CRISPR array that is cognate with the Cas3.
57. The vector of paragraph 54 or 55, wherein the host cell comprises an endogenous Type IA, B, C, D, U or E CRISPR/Cas system.
58. The vector of any one of paragraphs 1 to 29, wherein the Cas and Cascade are Type IA Cas and Cascade proteins.
59. The vector of any one of paragraphs 1 to 29, wherein the Cas and Cascade are Type IB Cas and Cascade proteins.
60. The vector of any one of paragraphs 1 to 29, wherein the Cas and Cascade are Type IC Cas and Cascade proteins.
61. The vector of any one of paragraphs 1 to 29, wherein the Cas and Cascade are Type ID Cas and Cascade proteins.
62. The vector of any one of paragraphs 1 to 29, wherein the Cas and Cascade are Type IE Cas and Cascade proteins.
63. The vector of any one of paragraphs 1 to 29, wherein the Cas and Cascade are Type IF Cas and Cascade proteins.
64. The vector of any one of paragraphs 1 to 29, wherein the Cas and Cascade are Type IU Cas and Cascade proteins.
65. The vector of any one of paragraphs 1 to 29, wherein the Cas and Cascade are *E coli* (optionally Type IE or IF) Cas and Cascade proteins, optionally wherein the *E coli* is ESBL-producing *E. coli* or *E. coli* ST131-025b:H4.
66. The vector of any one of paragraphs 1 to 29, wherein the Cas and Cascade are *Clostridium* (eg, *C dificile*) Cas and Cascade proteins, optionally *C dificile* resistant to one or more antibiotics selected from aminoglycosides, lincomycin, tetracyclines, erythromycin, clindamycin, penicillins, cephalosporins and fluoroquinolones.
67. The vector of any one of paragraphs 1 to 29, wherein the Cas and Cascade are *Pseudomonas aeruginosa* Cas and Cascade proteins, optionally *P aeruginosa* resistant to one or more antibiotics selected from carbapenems, aminoglycosides, cefepime, ceftazidime, fluoroquinolones, piperacillin and tazobactam.
68. The vector of any one of paragraphs 1 to 29, wherein the Cas and Cascade are *Klebsiella pneumoniae* (eg, carbapenem-resistant *Klebsiella pneumoniae* or Extended-Spectrum Beta-Lactamase (ESBL)-producing *K pneumoniae*) Cas and Cascade proteins.
69. The vector of any one of paragraphs 1 to 29, wherein the Cas and Cascade are *E coli, C difficile, P aeruginosa, K pneumoniae, P furiosus* or *B halodurans* Cas and Cascade proteins.
70. The vector of any preceding paragraph, wherein the Cas3 is a Cas3 of a CRISPR/Cas locus of a first bacterial or archaeal species, wherein the distance between the Cas3-encoding sequence of the locus and its cognate promoter is further than the distance between the Cas3-encoding sequence and the respective promoter comprised by the vector.

The cognate promoter here is the one that controls expression of Cas3 in the wild-type locus.

71. The vector of any preceding paragraph, wherein the distance between the promoter and the Cas3-encoding sequence and/or Cascade protein-encoding sequence(s) is shorter than in a corresponding wild-type Type I locus.

A corresponding locus is a wild-type locus of a bacterial or archaeal species or strain that comprises an endogenous CRISPR/Cas system encoding the Cas3 and/or Cascade proteins of the type that are also encoded by the vector. Thus, when the vector comprises an operon, the operon may comprise Cas3- and Cascade-encoding nucleotide sequences that are not in a natural configuration.

72. The vector of any preceding paragraph, wherein the vector comprises (i) a CRISPR array for producing crRNAs in the host cell and/or (ii) one or more nucleotide sequences encoding one or more single guide RNAs (gRNAs), wherein the crRNAs or gRNAs are cognate to the Cas3 (and optionally cognate to the Cascade proteins).
73. The vector of paragraph 72 when dependent from paragraph 4, wherein the array or gRNA-encoding sequence(s) are comprised by the operon and under the control of the promoter.
74. The vector of paragraph 72, wherein the array or gRNA-encoding sequence(s) are under the control of a promoter that is different from the promoter that controls the expression of the Cas3.
75. The vector of any one of paragraphs 72 to 74, wherein one or more of the crRNAs or gRNAs comprises a spacer sequence that is capable of hybridising to a target nucleotide sequence of the host cell, wherein the target sequence is adjacent a PAM, the PAM being cognate to the Cas3. Thus, the spacer hybridises to the protospacer to guide the Cas3 to the protospacer. Optionally, the Cas3 cuts the protospacer, eg, using exo- and/or endonuclease activity of the Cas3. Optionally, the Cas3 removes a plurality (eg, at least 2, 3,4, 5, 6, 7, 8, 9 or 10) nucleotides from the protospacer.
76. The vector of paragraph 75, wherein the target sequence is a chromosomal sequence of the host cell.
77. The vector of paragraph 75 or 76, wherein the Cas3 is operable to cut the target sequence.
78. The vector of any preceding paragraph, wherein the vector is a plasmid or phagemid.
79. A delivery vehicle comprising the vector of any preceding paragraph, wherein the delivery vehicle is capable of delivering the vector into the host cell.
80. The vehicle of paragraph 79, wherein the delivery vehicle is a phage, non-replicative transduction particle, nanoparticle carrier, bacterium or liposome.

The phage or particles comprise phage coat proteins encapsidating DNA, wherein the DNA comprises the vector. Suitable examples of phage and particles are disclosed in U.S. Ser. No. 15/985,658 (and its equivalent publication by USPTO) the disclosures of which are incorporated herein by reference for possible use in the invention and for providing one or more features that may be included in the claims herein. Phage or particle is capable of infecting the cell, thereby introducing the vector into the cell.

81. The vector or vehicle of any preceding paragraph, wherein the host cell is a bacterial or archaeal cell, optionally, the host cell is a *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cell.
82. The vector or vehicle of any preceding paragraph for administration to a human or animal subject for treating or reducing the risk of a disease or condition in the subject.
83. The vector or vehicle of paragraph 82, wherein the disease or condition is an infection of the subject with host cells (eg, bacterial cells), or wherein the disease or condition is mediated by host cells (eg, bacterial cells).
84. A pharmaceutical composition comprising the vector or vehicle of any preceding paragraph and a pharmaceutically acceptable diluent, excipient or carrier.
85. A method of amplifying copies of a DNA encoding a functional Cas protein (optionally a Cas nuclease) in a bacterial or archaeal production strain of cells, the method comprising
    (a) Providing production strain cells, each cell comprising a copy of said DNA, wherein each DNA comprises a nucleotide sequence encoding said Cas, wherein the nucleotide sequence is under the control of a promoter for controlling the expression of the Cas in the production strain cell, the DNA comprising an origin of replication that is operable in the cell for replication of the DNA;
    (b) Culturing the cells to allow replication of the DNA, whereby the DNA is amplified; and
    (c) Optionally isolating copies of the DNA,
86. The method of paragraph 85, wherein the promoter is a constitutive promoter.
87. The method of paragraph 85, wherein the promoter is repressible (optionally repressible by a tetracycline repressor or a lac repressor).
88. The method of paragraph 85, wherein the promoter is inducible.
89. The method of any one of paragraphs 85 to 88, wherein the promoter is a medium strength promoter.
90. The method of any one of paragraphs 85 to 89, wherein the promoter has an Anderson Score (AS) of 0.5>AS>0.1.
91. The method of any one of paragraphs 85 to 90, wherein the nucleotide sequence encoding said Cas is under the control of a promoter and translation initiation site (TIS) combination that is capable of producing expression of green fluorescent protein (GFP) from a first expression operating unit (EOU) in *E. coli* strain BW25113 cells with a fluorescence of from 0.5 to 4 times the fluorescence produced in *E. coli* strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.
92. The method of paragraph 91, wherein fluorescence using the first EOU is 0.5 to 2 times the fluorescence using the second EOU.
93. The method of any one of paragraphs 85 to 92, wherein the nuclease is Cas3 and optionally the DNA or cell encodes cognate Cascade proteins and/or one or more crRNAs that are operable for Cas nuclease targeting.

For example, the targeting is targeting of the Cas to a protospacer sequence comprised by a host cell chromosome or an episome thereof. In another example the targeting is in a recombineering method and the Cas is targeted to a protospacer sequence of a DNA that has been introduced into or amplified in the host cell. In an example of such recombineering, the host cell is an *E coli* cell.

94. The method of any one of paragraphs 85 to 92, wherein the Cas is a Cas9.
95. The method of any one of paragraphs 85 to 92, wherein the Cas is a Type IIIA csm protein or a Type IIIB cmr protein.
96. The method of any one of paragraphs 85 to 92, wherein the Cas is a Csf1.
97. The method of any one of paragraphs 85 to 92, wherein the Cas is a Cpf1.
98. The method of any one of paragraphs 85 to 92, wherein the Cas is a Cas13 (optionally Cas13a or Cas13b).
99. The method of any one of paragraphs 85 to 92, wherein the Cas is selected from a Cas3, Cas8a, Cas5, Cas8b, Cas8c, Cas10d, Cse1, Cse2, Csy1, Csy2, Csy3, GSU0054, Cas10, Csm2, Cmr5, Cas10, Csx11, Csx10, Csf1, Cas9, Csn2, Cas4, Cpf1, C2c1, C2c3, Cas13a, Cas13b and Cas13c.
100. The method of any one of paragraphs 85 to 99, wherein the production strain cells comprise a helper phage genome that is inducible to produce phage coat proteins in the cells, wherein the method further comprises inducing production of the phage proteins and causing packaging of the amplified DNA into phage particles or non-self-replicative transduction particles, and further isolating the phage or transduction particles and optionally formulating the particles into a pharmaceutical composition for administration to a human or animal subject for treating or reducing the risk of a disease or condition in the subject.
101. The method of paragraph 100, wherein the particles are capable of infecting target host cells in the subject and transducing the cells with the DNA, wherein the Cas and crRNAs (or gRNAs) encoded by the DNA are expressed in the cells, the crRNAs or (gRNAs) being operable to guide the Cas to a target nucleotide sequence (optionally a chromosomal sequence) comprised by the cells, wherein the Cas cuts the target sequences in the cells, thereby killing host cells and treating or reducing the risk of the disease or condition.
102. The method of paragraph 101, wherein the host cells are bacterial or archaeal cells, optionally, the host cells are *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cells.
103. The method of any one of paragraphs 85 to 102, wherein each DNA is comprised by a high copy number vector, optionally a high copy number plasmid (an optionally the promoter is a constitutive promoter).

104. The method of any one of paragraphs 85 to 103, wherein each DNA is comprised by a vector or vehicle according to any one of paragraphs 1 to 83.

105. Use of an attenuated strength promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for enhancing the yield of amplified DNA produced by the production host cells.

Thus, said enhancing may be relative to the yield produced using a strong promoter, eg, a strong constitutive promoter (for example a promoter having an Anderson Score (AS) of AS>0.5). In another example, the strong promoter is a promoter comprised by a promoter and translation initiation site (TIS) combination that is capable of producing expression of green fluorescent protein (GFP) from a first expression operating unit (EOU) in *E. coli* strain BW25113 cells with a fluorescence of >4 times the fluorescence produced in *E. coli* strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.

106. The use of paragraph 105, wherein the use is for enhancing said yield by
   (d) reducing toxicity of the Cas in the production strain;
   (e) reducing mutation of the DNA (optionally the Cas-encoding sequence) in the production strain;
   (f) promoting production cell viability during the amplification of the DNA; and/or
   (g) reducing the occurrence of Cas cutting of DNA (optionally cutting of production host cell chromosomal DNA or said DNA construct).

107. Use of an attenuated strength promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing toxicity of the Cas in the production strain.

108. Use of an attenuated strength promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing mutation of the DNA (optionally the Cas-encoding sequence) in the production strain.

109. Use of an attenuated strength promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for promoting production cell viability during the amplification of the DNA.

110. Use of an attenuated strength promoter in a DNA construct comprising a nucleotide sequence encoding a functional Cas protein (optionally a Cas nuclease) that is under the control of the promoter, in a method of amplifying copies of the DNA in a population of bacterial or archaeal production strain cells, the method comprising culturing the cells to allow replication of the DNA thereby amplifying the DNA in the cells, for reducing the occurrence of Cas cutting of DNA.

111. A method for enhancing the yield of amplified copies of a DNA construct in a population of bacterial or archaeal production strain cells, wherein the construct comprises a nucleotide sequence encoding a functional Cas protein (optionally a Cas nuclease) that is under the control of a promoter, the method comprising culturing the cells to allow replication of the DNA thereby amplifying the DNA in the cells, wherein the promoter is an attenuated strength promoter.

112. A method for reducing toxicity of a functional Cas protein (optionally a Cas nuclease) in a population of bacterial or archaeal production strain cells in a process of amplifying copies of a DNA construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated strength promoter.

113. A method for reducing mutation of a DNA construct encoding a functional Cas protein (optionally a Cas nuclease) in a population of bacterial or archaeal production strain cells in a process of amplifying copies of the construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated strength promoter.

114. A method for promoting production cell viability of a population of bacterial or archaeal production strain cells in a process of amplifying copies of a DNA construct comprised by the cells, wherein the construct comprises a nucleotide sequence encoding a functional Cas protein (optionally a Cas nuclease) and the sequence is under the control of a promoter, the method comprising culturing the cells to allow replication of the DNA thereby amplifying the DNA in the cells, wherein the promoter is an attenuated strength promoter.

115. A method for reducing the occurrence of Cas nuclease cutting of a DNA construct in a population of bacterial or archaeal production strain cells in a process of amplifying copies of the construct, wherein the construct comprises a nucleotide sequence encoding the Cas and the sequence is under the control of a promoter, the method comprising culturing the cells to allow replication of the DNA thereby amplifying the DNA in the cells, wherein the promoter is an attenuated strength promoter.

116. The use of paragraph 108 or 110, or the method of paragraph 113 or 115, wherein the mutation or cutting is mutation or cutting of host cell chromosomal DNA or the construct DNA.

117. The use or method of any one of paragraphs 105 to 116, wherein the promoter is a constitutive promoter.

118. The use or method of any one of paragraphs 105 to 117, wherein the promoter is repressible (optionally repressible by a tetracycline repressor or a lac repressor).

In an example, the promoter is a constitutive promoter and optionally the DNA is comprised by a high copy number plasmid or phagemid.

119. The use or method of any one of paragraphs 105 to 118, wherein the promoter is $P_{LtetO-1}$, $P_{LlacO-1}$ or a repressible homologue thereof.

$P_{LlacO-1}$ is repressed by lac repressor (LacR). $P_{LetO-1}$ is repressed by tet repressor (TetR).

120. The use or method of any one of paragraphs 105 to 119, wherein the promoter is a medium strength promoter.
121. The use or method of any one of paragraphs 105 to 120, wherein the promoter has an Anderson Score (AS) of 0.5>AS>0.1.
122. The use or method of any one of paragraphs 105 to 121, wherein the nucleotide sequence encoding said Cas is under the control of a promoter and translation initiation site (TIS) combination that is capable of producing expression of green fluorescent protein (GFP) from a first expression operating unit (EOU) in *E. coli* strain BW25113 cells with a fluorescence of from 0.5 to 4 times the fluorescence produced in *E. coli* strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.
123. The use or method of paragraph 122, wherein fluorescence using the first EOU is 0.5 to 2 times the fluorescence using the second EOU.
124. The use or method of any one of paragraphs 105 to 123, wherein the nuclease is Cas3 and optionally the DNA construct encodes cognate Cascade proteins.
125. The use or method of any one of paragraphs 105 to 123, wherein the Cas is a Cas9.
126. The use or method of any one of paragraphs 105 to 123, wherein the Cas is a Type IIIA csm protein or a Type IIIB cmr protein.
127. The use or method of any one of paragraphs 105 to 123, wherein the Cas is a Csf1.
128. The use or method of any one of paragraphs 105 to 123, wherein the Cas is a Cpf1.
129. The use or method of any one of paragraphs 105 to 123, wherein the Cas is a Cas13 (optionally Cas13a or Cas13b).
130. The use or method of any one of paragraphs 105 to 123, wherein the Cas is selected from a Cas3, Cas8a, Cas5, Cas8b, Cas8c, Cas10d, Cse1, Cse2, Csy1, Csy2, Csy3, GSU0054, Cas10, Csm2, Cmr5, Cas10, Csx11, Csx10, Csf1, Cas9, Csn2, Cas4, Cpf1, C2c1, C2c3, Cas13a, Cas13b and Cas13c.
131. The use or method of any one of paragraphs 105 to 130, wherein the DNA construct comprises one or more nucleotide sequences for producing crRNAs or gRNAs that are operable for Cas nuclease targeting.
132. The use or method of any one of paragraphs 105 to 131, wherein the production strain cells comprise a helper phage genome that is inducible to produce phage coat proteins in the cells, wherein the method further comprises inducing production of the phage proteins and causing packaging of the amplified DNA into phage particles or non-self-replicative transduction particles, and further isolating the phage or transduction particles and optionally formulating the particles into a pharmaceutical composition for administration to a human or animal subject for treating or reducing the risk of a disease or condition in the subject.
133. The method of paragraph 132, wherein the particles are capable of infecting target host cells in the subject and transducing the cells with the DNA, wherein the Cas and crRNAs (or gRNAs) encoded by the DNA are expressed in the cells, the crRNAs or (gRNAs) being operable to guide the Cas to a target nucleotide sequence (optionally a chromosomal sequence) comprised by the cells, wherein the Cas cuts the target sequences in the cells, thereby killing host cells and treating or reducing the risk of the disease or condition.
134. The method of paragraph 133, wherein the host cells are bacterial or archaeal cells, optionally, the host cells are *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cells.
135. The use or method of any one of paragraphs 105 to 134, wherein each DNA is comprised by a high copy number vector, optionally a high copy number plasmid (an optionally the promoter is a constitutive promoter).
136. The use or method of any one of paragraphs 105 to 135, wherein each DNA is comprised by a vector according to any one of paragraphs 1 to 78 and 81 to 83.

Clauses

The invention provides, by way of example, the following Clauses; the features of these are combinable with any other disclosure herein.

1. A nucleic acid vector for introduction into a host cell, the vector comprising a first nucleotide sequence encoding a Type I Cas3 and a second nucleotide sequence encoding one or more Cascade proteins, wherein the first and second sequences are under the control of one or more promoters comprised by the vector for expression of the proteins in the cell.
2. The vector of Clause 1, wherein the vector comprises an operon for expression in the cell of the Cas3 and Cascade proteins from a Cas module, the module comprising the nucleotide sequences encoding the Cas3 and Cascade proteins, and the operon comprising the Cas module under the control of a promoter for controlling the expression of both the Cas3 and Cascade proteins.
3. The vector of Clause 2, wherein
   (a) the first sequence is between the promoter and the second sequence in the operon;
   (b) the operon comprises no Cas-encoding nucleotide sequences between the promoter and the first nucleotide sequence; and/or
   (c) the operon comprises (in 5' to 3' direction) the promoter, the first sequence and the second sequence.
4. The vector of any preceding Clause, wherein each promoter is a constitutive promoter.
5. The vector of any one of Clauses 1 to 3, wherein the promoter is repressible (optionally repressible by a tetracycline repressor or lac repressor).
6. The vector of any one of Clauses 1 to 3, wherein the promoter is inducible.
7. The vector of any preceding Clause, wherein the first sequence is under the control of a medium strength promoter.
8. The vector of any preceding Clause, wherein the first sequence is under the control of a promoter that has an Anderson Score (AS) of 0.5>AS>0.1.

9. The vector of any preceding Clause, wherein the first sequence (and optionally the second sequence) is under the control of a promoter and translation initiation site (TIS) combination that is capable of producing expression of green fluorescent protein (GFP) from a first expression operating unit (EOU) in *E. coli* strain BW25113 cells with a fluorescence of from 0.5 to 4 times the fluorescence produced in *E. coli* strain BW25113 cells using a second EOU comprising a P10 promoter (SEQ ID NO: 1) combined with a BCD14 TIS (SEQ ID NO: 2), wherein the EOUs differ only in their promoter and TIS combinations, wherein each EOU comprises (in 5' to 3' direction) an upstream initiator, the respective promoter, the respective TIS, a nucleotide sequence encoding GFP, a 3' UTR, a transcription terminator and a downstream insulator.

10. The vector of Clause 9, wherein fluorescence using the first EOU is 0.5 to 2 times the fluorescence using the second EOU.

11. The vector of any preceding Clause, wherein the vector comprises an origin of replication that is operable in the host cell.

12. The vector of any preceding Clause, wherein the vector comprises an origin of replication that is operable in a bacterial cell of a vector production strain, wherein the Cas3 is not operable in the production strain cell to target and cut a chromosomal sequence thereof.

13. The vector of Clause 12, wherein the first sequence is under the control of a promoter that is capable of controlling expression of the Cas3 at a level that is not toxic to the production strain cell.

14. The vector of any preceding Clause, wherein the vector is a high copy number vector.

15. The vector of any preceding Clause, wherein the first nucleotide sequence or operon is comprised by a mobile genetic element.

16. The vector of any preceding Clause, wherein the vector is devoid of a Cas adaption module.

17. The vector of any preceding Clause, wherein the vector is devoid of nucleotide sequence encoding one, more or all of a Cas1, Cast, Cas4, Cas6, Cas7 and Cas 8.

18. The vector of any preceding Clause, wherein the vector comprises (optionally in 5' to 3' direction) nucleotide sequence encoding one, more or all of Cas11, Cas7 and Cas8a1.

19. The vector of Clause 18, wherein the vector comprises nucleotide sequence encoding Cas3' and/or Cas3".

20. The vector or Clause 19, wherein the nucleotide sequences encoding the Cas3' and/or Cas3" are between the promoter and the sequence(s) recited in Clause 18.

21. The vector of any one of Clauses 18 to 20, wherein the host cell comprises a Type IA CRISPR array that is cognate with the Cas3.

22. The vector of any one of Clauses 18 to 20, wherein the host cell comprises an endogenous Type 1B, C, U, D, E or F CRISPR/Cas system.

23. The vector of any one of Clauses 1 to 17, wherein the vector comprises (optionally in 5' to 3' direction) nucleotide sequence encoding one, more or all of Cas8b1, Cas7 and Cas5.

24. The vector of Clause 23, wherein the vector comprises a nucleotide sequence encoding Cas3 between the promoter and the sequence(s) recited in Clause 23.

25. The vector of Clause 23 or 24, wherein the host cell comprises a Type IB CRISPR array that is cognate with the Cas3.

26. The vector of Clause 23 or 24, wherein the host cell comprises an endogenous Type IA, C, U, D, E or F CRISPR/Cas system.

27. The vector of any one of Clauses 1 to 17, wherein the vector comprises (optionally in 5' to 3' direction) nucleotide sequence encoding one, more or all of Cas5, Cas8c and Cas7.

28. The vector of Clause 27, wherein the vector comprises a nucleotide sequence encoding Cas3 between the promoter and the sequence(s) recited in Clause 27.

29. The vector of Clause 27 or 28, wherein the host cell comprises a Type IC CRISPR array that is cognate with the Cas3.

30. The vector of Clause 27 or 28, wherein the host cell comprises an endogenous Type IA, B, U, D, E or F CRISPR/Cas system.

31. The vector of any one of Clauses 1 to 17, wherein the vector comprises (optionally in 5' to 3' direction) nucleotide sequence encoding one, more or all of Cas8U2, Cas7, Cas5 and Cas6.

32. The vector of Clause 31, wherein the vector comprises a nucleotide sequence encoding Cas3 between the promoter and the sequence(s) recited in Clause 31.

33. The vector of Clause 31 or 32, wherein the host cell comprises a Type IU CRISPR array that is cognate with the Cas3.

34. The vector of Clause 31 or 32, wherein the host cell comprises an endogenous Type IA, B, C, D, E or F CRISPR/Cas system.

35. The vector of any one of Clauses 1 to 17, wherein the vector comprises (optionally in 5' to 3' direction) nucleotide sequence encoding one, more or all of Cas10d, Cas7 and Cas5.

36. The vector of Clause 35, wherein the vector comprises a nucleotide sequence encoding Cas3' and/or Cas3".

37. The vector of Clause 36, wherein the nucleotide sequences encoding the Cas3' and/or Cas3" are between the promoter and the sequence(s) recited in Clause 35.

38. The vector of any one of Clauses 35 to 37, wherein the host cell comprises a Type ID CRISPR array that is cognate with the Cas3.

39. The vector of any one of Clauses 35 to 37, wherein the host cell comprises an endogenous Type IA, B, C, U, E or F CRISPR/Cas system.

40. The vector of any one of Clauses 1 to 17, wherein the vector comprises (optionally in 5' to 3' direction) nucleotide sequence encoding one, more or all of Cas8e, Cas11, Cas7, Cas5 and Cas6.

41. The vector of Clause 40, wherein the vector comprises a nucleotide sequence encoding Cas3 between the promoter and the sequence(s) recited in Clause 40.

42. The vector of Clause 40 or 41, wherein the host cell comprises a Type IE CRISPR array that is cognate with the Cas3.

43. The vector of Clause 40 or 41, wherein the host cell comprises an endogenous Type IA, B, C, D, U or F CRISPR/Cas system.

44. The vector of any one of Clauses 1 to 17, wherein the vector comprises (optionally in 5' to 3' direction) nucleotide sequence encoding one, more or all of Cas8f, Cas5, Cas7 and Cas6f.

45. The vector of Clause 44, wherein the vector comprises a nucleotide sequence encoding Cas3 between the promoter and the sequence(s) recited in Clause 44, wherein the vector is devoid of nucleotide sequence encoding further Cas between the promoter and the sequence encoding the Cas3.

46. The vector of Clause 44 or 45, wherein the host cell comprises a Type IF CRISPR array that is cognate with the Cas3.
47. The vector of Clause 44 or 45, wherein the host cell comprises an endogenous Type IA, B, C, D, U or E CRISPR/Cas system.
48. The vector of any one of Clauses 1 to 17, wherein the Cas and Cascade are
    (a) Type IA Cas and Cascade proteins;
    (b) Type IB Cas and Cascade proteins;
    (c) Type IC Cas and Cascade proteins;
    (d) Type ID Cas and Cascade proteins;
    (e) Type IE Cas and Cascade proteins;
    (f) Type IF Cas and Cascade proteins; or
    (g) Type IU Cas and Cascade proteins.
49. The vector of any preceding Clause, wherein the Cas and Cascade are *E coli* (optionally Type IE or IF) Cas and Cascade proteins.
50. The vector of Clause 49, wherein the *E coli* is ESBL-producing *E. coli* or *E. coli* ST131-025b:H4.
51. The vector of any preceding Clause, wherein the Cas and Cascade are
    (a) *Clostridium* (eg, *C dificile*) Cas and Cascade proteins, optionally *C dificile* resistant to one or more antibiotics selected from aminoglycosides, lincomycin, tetracyclines, erythromycin, clindamycin, penicillins, cephalosporins and fluoroquinolones;
    (b) *Pseudomonas aeruginosa* Cas and Cascade proteins, optionally *P aeruginosa* resistant to one or more antibiotics selected from carbapenems, aminoglycosides, cefepime, ceftazidime, fluoroquinolones, piperacillin and tazobactam; or
    (c) *Klebsiella pneumoniae* (eg, carbapenem-resistant *Klebsiella pneumoniae* or Extended-Spectrum Beta-Lactamase (ESBL)-producing *K pneumoniae*) Cas and Cascade proteins.
52. The vector of any preceding Clause, wherein the Cas and Cascade are *E coli, C difficile, P aeruginosa, K pneumoniae, P furiosus* or *B halodurans* Cas and Cascade proteins.
53. The vector of any preceding Clause, wherein the Cas3 is a Cas3 of a CRISPR/Cas locus of a first bacterial or archaeal species, wherein the distance between the Cas3-encoding sequence of the locus and its cognate promoter is further than the distance between the Cas3-encoding sequence and the respective promoter comprised by the vector.
54. The vector of any preceding Clause, wherein the distance between the promoter and the Cas3-encoding sequence and/or Cascade protein-encoding sequence(s) is shorter than in a corresponding wild-type Type I locus.
55. The vector of any preceding Clause, wherein the vector comprises (i) a CRISPR array for producing crRNAs in the host cell and/or (ii) one or more nucleotide sequences encoding one or more guide RNAs (gRNAs or single gRNAs), wherein the crRNAs or gRNAs are cognate to the Cas3 (and optionally cognate to the Cascade proteins).
56. The vector of Clause 55 when dependent from Clause 2, wherein the array or gRNA-encoding sequence(s) are comprised by the operon and under the control of the promoter.
57. The vector of Clause 56, wherein the array or gRNA-encoding sequence(s) are under the control of a promoter that is different from the promoter that controls the expression of the Cas3.
58. The vector of Clause 56 or 57, wherein one or more of the crRNAs or gRNAs comprises a spacer sequence that is capable of hybridising to a target nucleotide sequence of the host cell, wherein the target sequence is adjacent a PAM, the PAM being cognate to the Cas3.
59. The vector of Clause 58, wherein the target sequence is a chromosomal sequence of the host cell.
60. The vector of Clause 58 or 59, wherein the Cas3 is operable to cut the target sequence.
61. The vector of any preceding Clause, wherein the vector is a plasmid or phagemid.
62. A delivery vehicle comprising the vector of any preceding Clause, wherein the delivery vehicle is capable of delivering the vector into the host cell.
63. The vehicle of Clause 62, wherein the delivery vehicle is a phage, non-replicative transduction particle, nanoparticle carrier, bacterium or liposome.
64. The vector or vehicle of any preceding Clause, wherein the host cell is a bacterial or archaeal cell, optionally, the host cell is a *C dificile, P aeruginosa, K pneumoniae* (eg, carbapenem-resistant *Klebsiella pneumoniae* or Extended-Spectrum Beta-Lactamase (ESBL)-producing *K pneumoniae*), *E coli* (eg, ESBL-producing *E. coli*, or *E. coli* ST131-025b:H4), *H pylori, S pneumoniae* or *S aureus* cell.
65. The vector or vehicle of any preceding Clause for administration to a human or animal subject for treating or reducing the risk of a disease or condition in the subject.
66. The vector or vehicle of Clause 65, wherein the disease or condition is an infection of the subject with host cells (eg, bacterial cells), or wherein the disease or condition is mediated by host cells (eg, bacterial cells).
67. A pharmaceutical composition comprising the vector or vehicle of any preceding Clause and a pharmaceutically acceptable diluent, excipient or carrier.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. Reference is made to WO2017/118598, US20180140698, US20170246221, US20180273940, US20160115488, US20180179547, US20170175142, US20160024510, US20150064138, US20170022499, US20160345578, US20180155729, US20180200342, WO2017112620, WO2018081502, PCT/EP2018/066954, PCT/EP2018/066980, PCT/EP2018/071454 and U.S. Ser. No. 15/985,658 and equivalent publications by the US Patent and Trademark Office (USPTO) or WIPO, the disclosures of which are incorporated herein by reference for providing disclosure that may be used in the present invention and/or to provide one or more features (eg, of a vector) that may be included in one or more claims herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non-limiting Examples.

EXAMPLES

The examples illustrate fast and precision killing of *Escherichia coli* strains. As a model programmable nuclease system, we used a CRISPR guided vector (CGV™) to specifically target *Escherichia coli* MG1655.

Example 1. Single-Vector Cas3 & Cascade: Type I CRISPR-Cas System Targeting *E. coli*

A plasmid (which we call a CRISPR Guided Vector™, CGV™) was constructed comprising an operon with nucleotide sequences encoding a Type I Cas3 and Cascade proteins under the control of a common promoter. *C. dificile* Type IB Cas3 and Cascade was used. A cognate CRISPR array comprising *C. dificile* repeat sequences and spacer sequence for targeting an *E. coli* host cell chromosome was also introduced into target cells. An adaptation module containing Cas1, Cas1 and Cas4 was omitted in the vector (see FIG. 1A). In the wild-type *C. dificile* Type IB CRISPR/Cas locus, the cas3 gene is 3' of the Cascade genes (cas8b1, cas7 and cas5) and thus spaced away from the promoter upstream of the Cascade genes. When we tried this arrangement, we found killing of *E. coli* cells, but surprisingly when we changed to a synthetic operon arrangement (in 5' to 3' orientation) of promoter, cas3, cas8b1, cas7 and cas5 we saw significantly higher killing of the target *E. coli* cells.

Figure 1B:
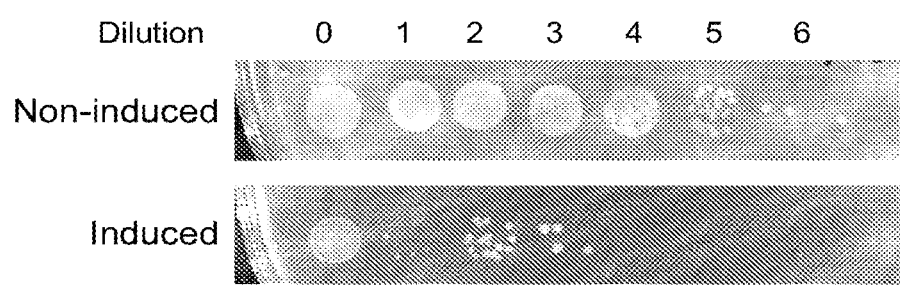
Figure 1C:
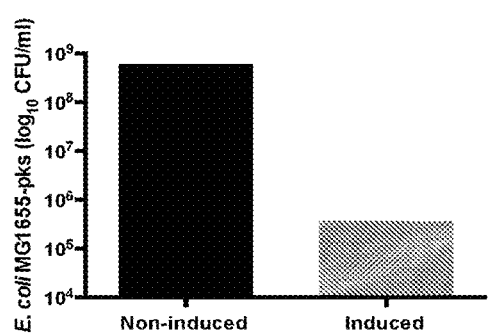

Results using this synthetic operon arrangement are shown in FIGS. 1A-1C. In FIG. 1B there is shown a dilution series ($10^1$-$10^6$) of drop spots (5 µl) of target *E. coli* MG1655 cells harboring the CGV on LB agar plates with and without inducers. CRISPR/Cas induction surprisingly killed 99.9% of the population (FIG. 1C, grey bar). Growth in absence of induction is shown in black. CGV™ refers to a CRISPR Guided Vector™, which is a nucleic acid vector comprising nucleotide sequences encoding CRISPR/Cas components.

We also managed to achieve desirable targeted killing of *E coli* cells using a similar set-up, except that *E coli* Type IE Cas and Cascade were used, together with a cognate array targeting host cell *E coli* chromosomal DNA (data not shown). In this case, a vector was used comprising (in 5' to 3' direction) a promoter controlling the expression of Cas3, Cas8e, Cas11, Cas7, Cas5 and Cas6 in an operon.

Materials and Methods

*E. coli* MG1655 was grown in lysogeny broth (LB) with shaking (250 rpm) at 37° C. When necessary, cultures were supplemented with tetracycline (10 µg/mL), and spectinomycin (400 µg/mL).

To construct a plasmid containing *C. difficile* CRISPR system under arabinose inducible pBAD promoter, cas3, cas6, cas8b, cas7 and cas5 genes from *C. difficile* were amplified and cloned in a low copy number plasmid (pSC101 ori). cas3 was located in the beginning of the operon followed by cas6, cas8b, cas7 and cas5. The adaptation module (consisting of cas1, cast, and cas4) was omitted in the vector (FIG. 1A). A second plasmid containing an IPTG inducible single-spacer array targeting a chromosomal intergenic region in *E. coli* MG1655 was constructed (FIG. 1A). The spacer was cloned under control of the IPTG-inducible Ptrc promoter, in a CloDF13 on backbone. It contains 37 nucleotides from the genome of *E. coli* MG1655 (ctttgccgcgcgcttcgtcacgtaattctcgtcgcaa) (SEQ ID NO: 26). Additionally, the 3'-CCT protospacer adjacent motif (PAM) is located adjacent to the selected target sequence in the genome of *E. coli* MG1655 (FIG. 1A).

To perform killing assays, both plasmids were transformed into *E. coli* MG1655 by electroporation. Transformants were grown in liquid LB with antibiotics to mid-log phase, and the killing efficiency was determined by serial dilution and spot plating onto LB, and LB+inducers (0.5 mM IPTG and 1 arabinose). Viability was calculated by counting colony forming units (CFUs) on the plates and data were calculated as viable cell concentration (CFU/ml).

Example 2. Single-Vector Cas3-Cascade & Array: Type I CRISPR-Cas System Targeting *E. coli*

A plasmid (which we call a CRISPR Guided Vector™, CGV™, which is a nucleic acid vector comprising nucleotide sequences encoding CRISPR/Cas components) was constructed comprising an operon with nucleotide sequences encoding a Type I Cas3 and Cascade proteins under the control of a common promoter. *C. difficile* Type IB Cas3 and Cascade was used. Adaptation module containing Cas1, Cas2 and Cas4 was omitted in the vector. A cognate CRISPR array comprising *C. difficile* repeat sequences and spacer sequence for targeting an *E. coli* host cell chromosome was also cloned in the vector (see FIG. 2A). Similarly we also constructed a plasmid comprising of an operon with nucleotide sequences encoding *E. coli* Type IE Cas3 and Cascade proteins under control of a common promoter. The *E. coli* adaption module containing Cas1 and Cas2 was omitted, in the vector. A cognate CRISPR array comprising *E. coli* repeat sequences and spacer sequence for targeting an *E. coli* host cell chromosome was also cloned in the vector.

Figure 2A:
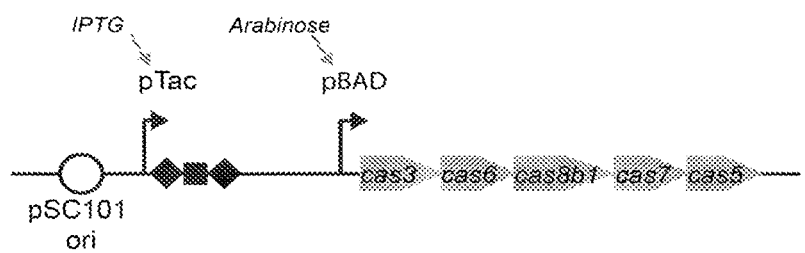
FIGS. 2A-2C. Type I CRISPR-Cas system of *C. difficile* targeting *E. coli* MG1655.
Figure 2B:
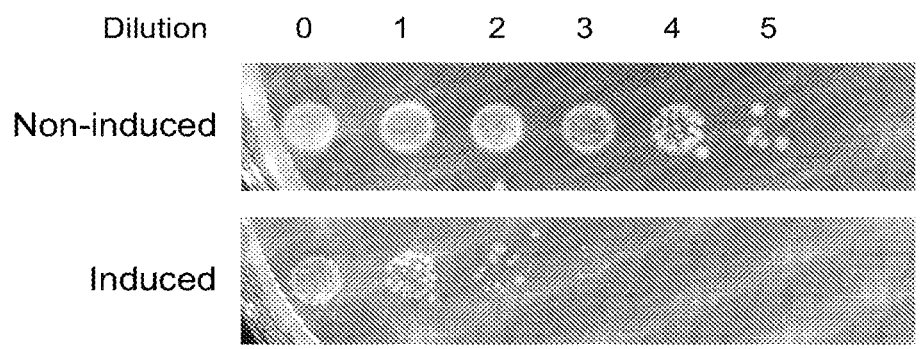
Figure 2C:
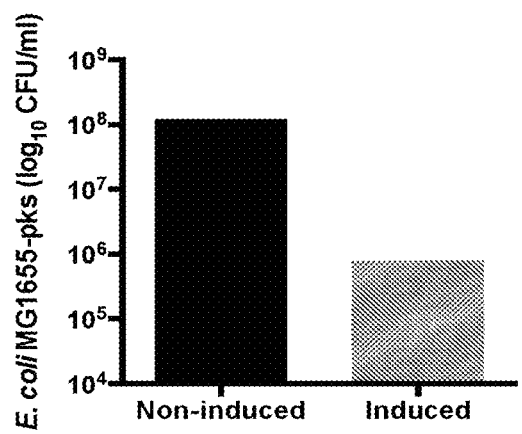

The CGV containing the *C. difficile* CRISPR-Cas system was transformed into *E. coli* MG1655 which contains a pks sequence incorporated into the genome. Results using this synthetic operon arrangement are shown in FIGS. 2A-2C. In FIG. 2B there is shown a dilution series ($10^1$-$10^5$) of drop spots (5 µl) of target *E. coli* MG1655 cells harboring the CGV on synthetic medium (SM) agar plates with and without inducers. CRISPR/Cas induction resulted in more than 2-$\log_{10}$ reductions in viable cells of *E. coli* MG1655 (FIG. 2C, grey bar). Growth in absence of induction is shown in black. CGV™ refers to a CRISPR Guided Vector™.

Figure 3A:
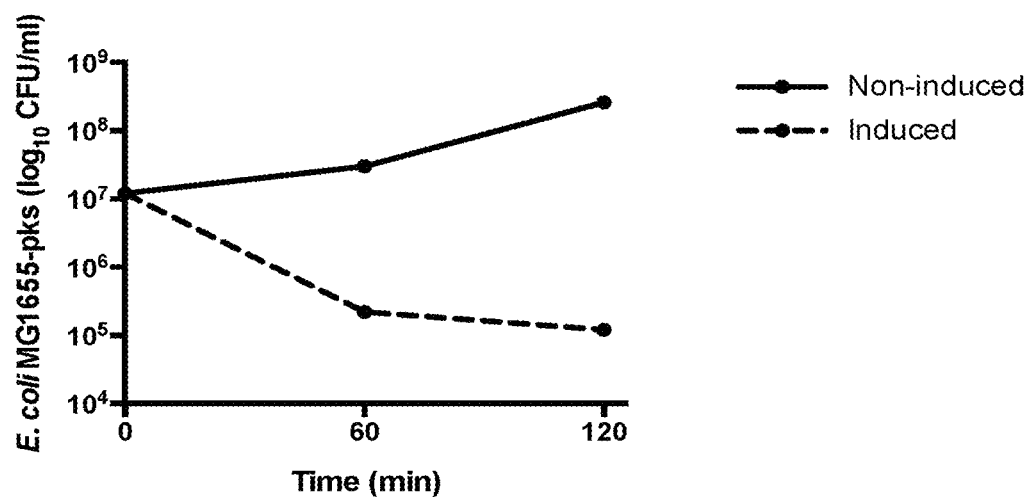
FIGS. 3A-3B. Time-kill curves for *E. coli* MG1655 harboring the CGV.
Figure 3B:
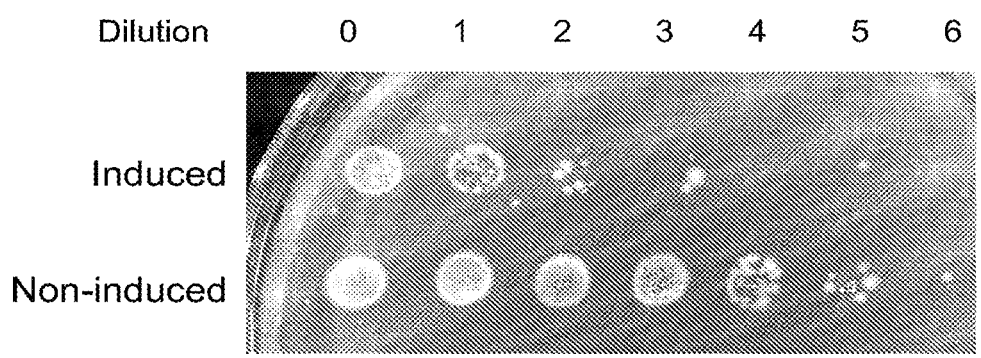

The survival of *E. coli* MG1655 upon induction was followed over time by plating the cultures in serial dilutions every 60 minutes, for 2 h (FIG. 3A). Killing curves revealed that CRISPR/Cas induction mediated rapid killing of *E. coli* MG1655, generating a two-$\log_{10}$ reduction in *E. coli* by the first 60 minutes. FIG. 3B shows a dilution series ($10^1$-$10^6$) of drop spots (5 µl) of induced and non-induced cultures of target *E. coli* MG1655 on SM agar plates.

Figure 6A:
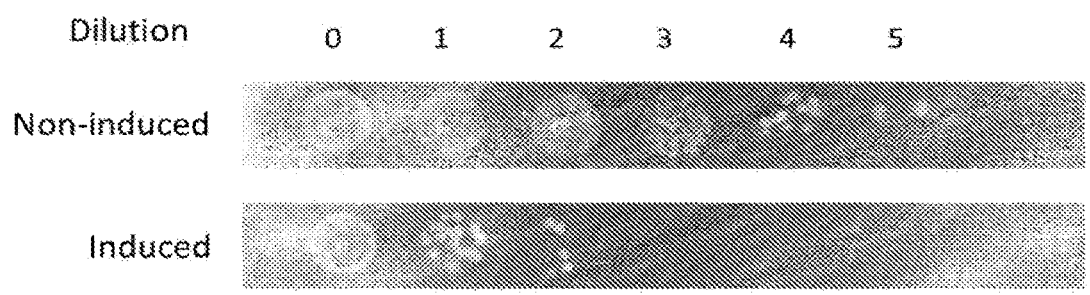
FIGS. 6A-6B. Type I CRISPR-Cas system of *E. coli* targeting *E. coli* MG1655.
Figure 6B:
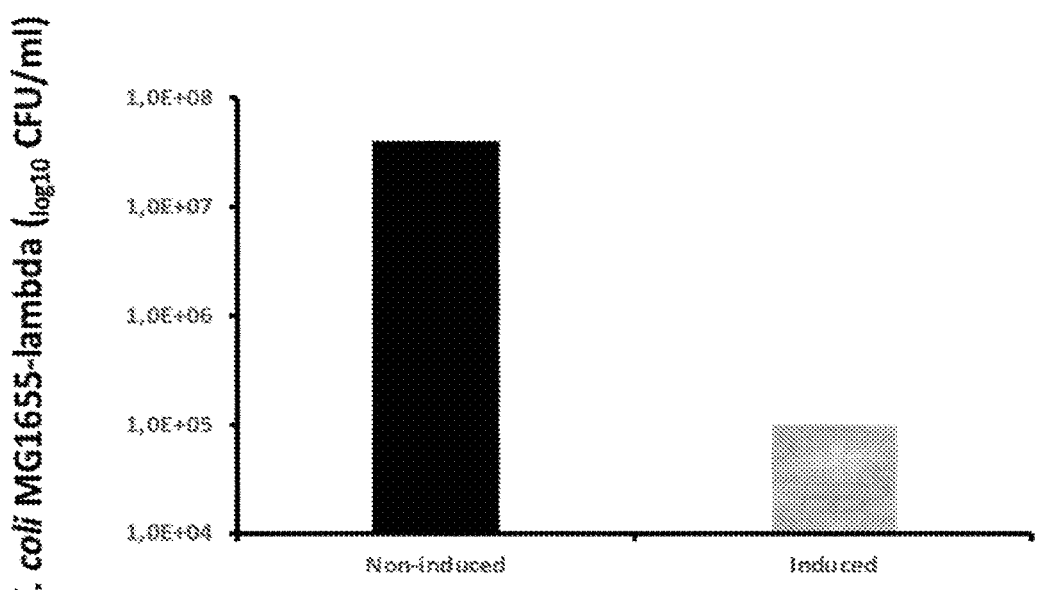

The CGV containing the *E. coli* CRISPR-Cas system was transformed into other *E. coli* MG1655 cells which contain a lambda sequence incorporated into the genome. Results using this synthetic operon arrangement are shown in FIGS. 6A-6B. In FIG. 6A there is shown a dilution series ($10^1$-$10^5$) of drop spots (5 µl) of target *E. coli* MG1655 cells harboring the CGV on synthetic medium (SM) agar plates with and without inducers. CRISPR/Cas induction resulted in more than 2-$\log_{10}$ reductions in viable cells of *E. coli* MG1655 (FIG. 6B, grey bar). Growth in absence of induction is shown in black. In a repeat experiment (not shown) we saw a 3-$\log_{10}$ reductions in viable cells of *E. coli* MG1655 with CRISPR/Cas induction.

Materials and Methods

*E. coli* MG1655 was grown in synthetic medium (SM) with shaking (250 rpm) at 37° C. Cultures were supplemented with 10 µg/mL tetracycline when required.

To construct a plasmid containing *C. difficile* CRISPR system under arabinose inducible pBAD promoter, cas3, cas6, cas8b, cas7 and cas5 genes from *C. difficile* were amplified and cloned in a low copy number plasmid (pSC101 ori). cas3 was located in the beginning of the operon followed by cas6, cas8b, cas7 and cas5. Additionally, an IPTG inducible single-spacer array targeting a chromosomal intergenic region in *E. coli* MG1655 was included in the vector under control of the IPTG-inducible Ptrc promoter (FIG. 2A). It contains 37 nucleotides from the PKS gene (previously integrated into the genome of *E. coli* MG1655) (gtttggcgatggcgcgggtgtggttgtgcttcggcgt) (SEQ ID NO: 27). Additionally, the 3'-CCT protospacer adjacent motif (PAM) is located adjacent to the selected target sequence in the genome of *E. coli* MG1655 (FIG. 2A).

To construct a plasmid containing *E. coli* CRISPR system under arabinose inducible pBAD promoter, cas3, cse1, cse2, cas7, cas5 and cas6 genes from *E. coli* were amplified and cloned in a low copy number plasmid (pSC101 ori). The operon comprised (in 5' to 3' direction) cas3 followed by cse1 cse2, cas7, cas5 and cas6. Additionally, an IPTG inducible single-spacer array targeting a chromosomal intergenic region in *E. coli* MG1655 was included in the vector under control of the IPTG-inducible Ptrc promoter. It contained 32 nucleotides from the lambda sequence (previously integrated into the genome of *E. coli* MG1655) (tgggatgcctaccgcaagcagcttggcctgaa) (SEQ ID NO: 28) and found to efficiently target in Brouns et al., 2008 (Science. 2008 Aug. 15; 321(5891):960-4. doi: 10.1126/science.1159689; "Small CRISPR RNAs guide antiviral defense in prokaryotes"). Additionally, the 3'-ATG protospacer adjacent motif (PAM) is located adjacent to the selected target sequence in the genome of *E. coli* MG1655.

The CGVs were transformed into *E. coli* MG1655 by electroporation. Transformants were grown in liquid SM with antibiotics to mid-log phase, and the killing efficiency was determined by serial dilution and spot plating onto LB, and LB+inducers (0.5 mM IPTG and 1% arabinose). Viability was calculated by counting colony forming units (CFUs) on the plates and data were calculated as viable cell concentration (CFU/ml).

To perform killing curves, *E. coli* MG1655 harboring the CGV was grown in liquid SM with antibiotics to mid-log phase. The culture was divided into two tubes and either inducers (0.5 mM IPTG and 1% arabinose) or PBS were added. Survival of the strain was followed over time by plating the cultures in serial dilutions ($10^1$-$10^6$) of drop spots (5 µl) every 60 minutes, for 2 h, on SM plates with antibiotics. Survival frequency was calculated by counting colony forming units (CFUs) on the plates and data were calculated as viable cell concentration (CFU/ml).

Example 3. Precision Killing of Target Strain *E. coli* MG1655 in a Microbiome

An artificial microbial consortium was constructed to study the efficiency of the CGV carrying the CRISPR-Cas system of *C. difficile*, to specifically target *E. coli* MG1655 in the presence of other microbes, mimicking the human microbiome.

Figure 4A:
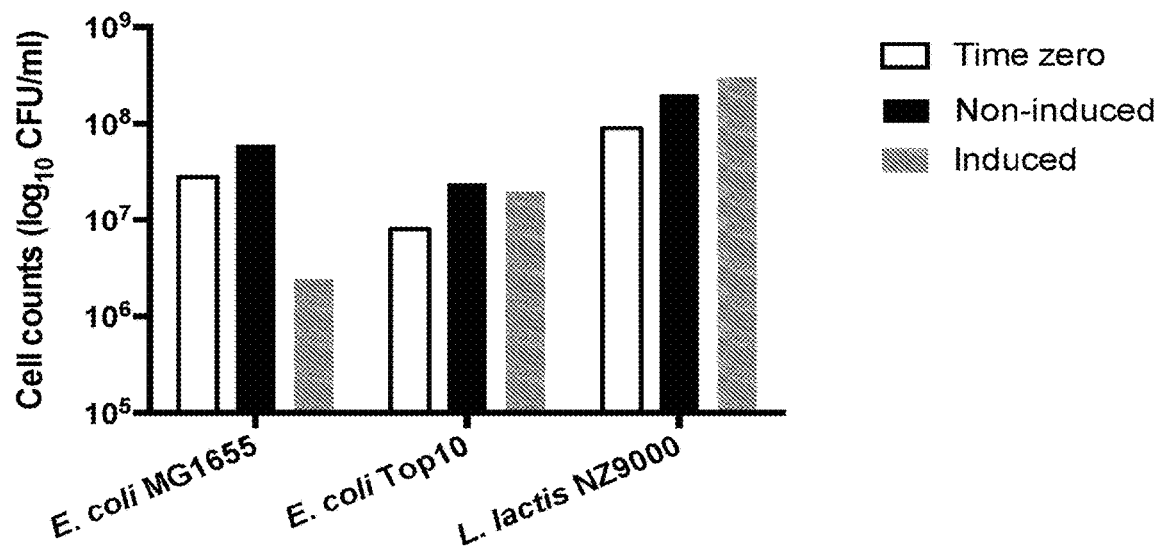
FIGS. 4A-4B. Specific killing of *E. coli* MG1655 with type I-B CRISPR-Cas system of *C. difficile* in a synthetic microbial consortium.
Figure 4B:
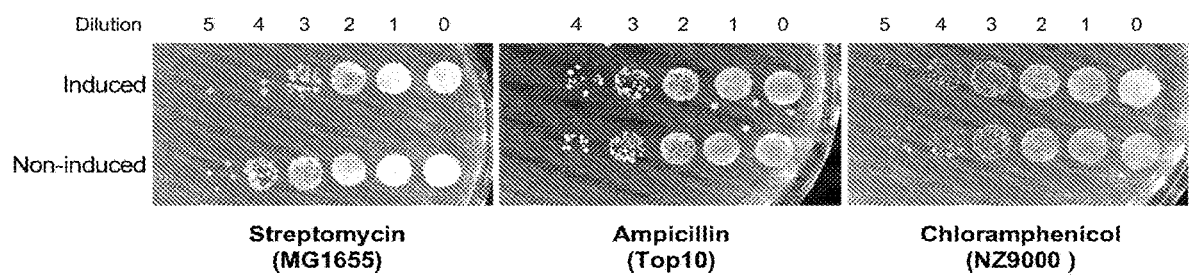

The synthetic consortium consisted of three strains (two different species) with differential antibiotic resistance profiles: a streptomycin-resistant *E. coli* MG1655 (target strain), an ampicillin-resistant *E. coli* Top10, and a chloramphenicol-resistant *Lactococcus lactis* NZ9000. To create the consortium, bacterial cultures were grown separately in Brain Heart Infusion broth (BHI, optimal growth medium for *L. lactis*) to mid-log phase and mixed in fresh BHI broth with and without inducers. After 1 h induction at 30° C., the composition of the consortium was determined by counting viable colonies on selective plates. Induction of the CRISPR system in the mixed community, resulted in >10-fold killing of target *E. coli* MG1655, while leaving *E. coli* Top10 and *L. lactis* NZ9000 cell populations unharmed (FIG. 4A). In FIG. 4B there is shown a dilution series ($10^1$-$10^5$) of drop spots (5 µl) of the synthetic consortium after 1 h induction on BHI agar plates.

Figure 5A:
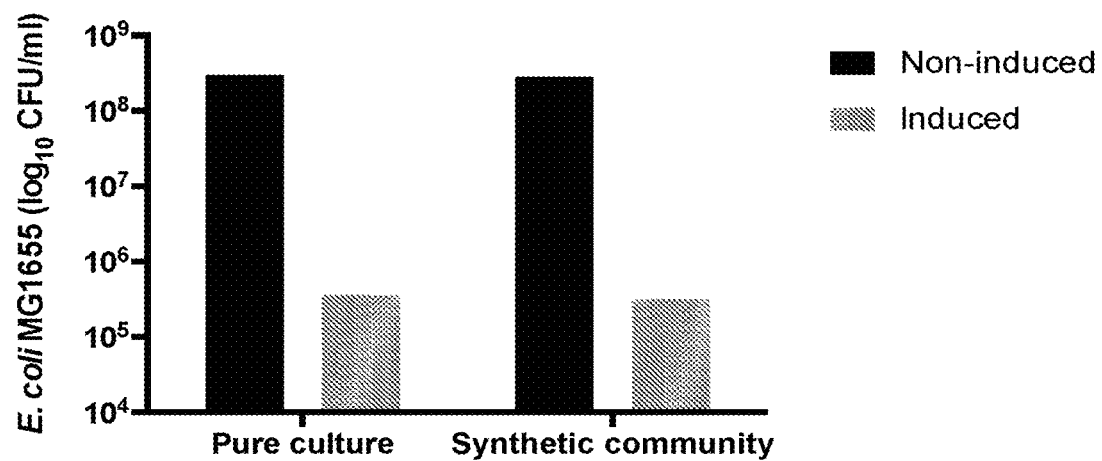
FIGS. 5A-5B. Killing of *E. coli* MG1655 with type I-B CRISPR-Cas system of *C. difficile* in a synthetic microbial consortium compared to a pure culture of *E. coli* MG1655.
Figure 5B:
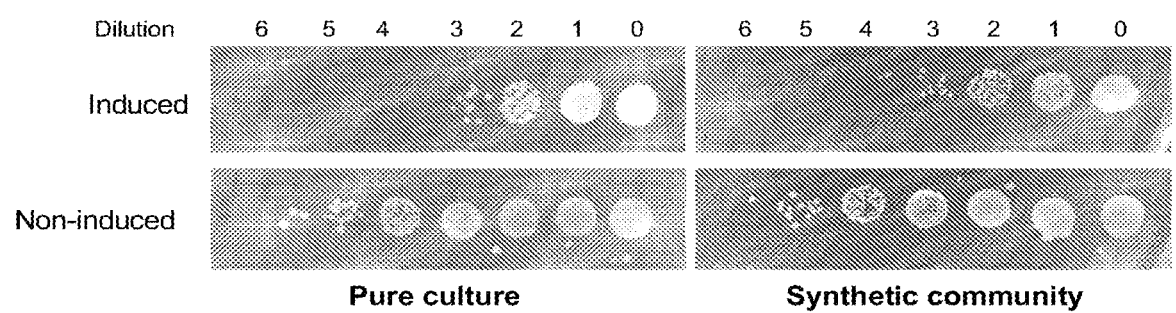

Additionally, CRISPR killing of target strain *E. coli* MG1655 in the synthetic microbial consortium was compared to a pure culture (ie, target strain *E. coli* MG1655 that is not mixed with another strain or species). Unexpectedly, in both conditions, killing of 3 logs was achieved when plated on BHI agar plates with inducers (FIG. 5A). Thus, surprisingly the killing in the microbiome setting was as efficient as the killing in pure culture. In FIG. 5B there is shown a dilution series ($10^1$-$10^5$) of drop spots (5 µl) of the synthetic consortium and *E. coli* MG1655 in pure culture on BHI agar plates with and without inducers.

Materials and Methods

*E. coli* MG1655, *E. coli* Top10, and *Lactococcus lactis* NZ9000 were grown in BHI broth with shaking (250 rpm) at 30° C. Cultures were supplemented with 1000 µg/mL streptomycin, 100 µg/mL ampicillin, or 10 µg/mL chloramphenicol, respectively.

To create the consortium, bacterial cultures were grown in BHI with appropriate antibiotics to mid-log phase. Cultures were washed twice in PBS to remove the antibiotics and mixed in fresh BHI broth. The mixed culture was spotted onto BHI plates with streptomycin, ampicillin or chloramphenicol to quantify the initial concentration of *E. coli* MG1655, *E. coli* Top10 and *L. lactis* NZ9000, respectively. The mixed culture was divided into two tubes and either inducers (0.5 mM IPTG and 1% arabinose) or PBS were added. After 1 h induction at 30° C., the composition of the consortium was calculated by counting colony forming units (CFUs) on selective plates and data were calculated as viable cell concentration (CFU/ml).

Example 4. Use of Promoter Repression in Vector Amplification Strains

We engineered an *E coli* Top10 production strain cell population comprising plasmid CGV DNA and an expressible sequence encoding a Tet repressor (TetR). The DNA comprised a Cas9-encoding nucleotide sequence under the control of a Tet promoter (pLtetO-1 promoter). The promoter is normally constitutively ON, but it was repressed by TetR in our cells. Thus, in this way we could successfully culture the cells and amplify the CGV without observing adverse toxicity due to Cas9 expression.

In an experiment in the absence of repression, we did not observe any colonies of production strain bacteria, and we surmise that this was due to Cas9 toxicity. We believe, in addition to providing a way of increasing CGV yield (eg, for subsequent packaging into phage or non-self-replicative transduction particles), our method using repression can minimize selection for mutations in the DNA that would otherwise be forced by higher Cas9 expression and cutting (eg, due to CGV cutting).

REFERENCES

Mutalik et al, Nat Methods. 2013 April; 10(4):354-60. doi: 10.1038/nmeth. 2404. Epub 2013 Mar. 10, "Precise and reliable gene expression via standard transcription and translation initiation elements".

TABLE 1

Example Bacteria
Optionally, the target host cells are cells of a genus or species selected from this Table
and/or the production strain cells are cells of a genus or species selected from this Table

| | | | | |
|---|---|---|---|---|
| Abiotrophia | Acidocella | Actinomyces | Alkalilimnicola | Aquaspirillum |
| Abiotrophia defectiva | Acidocella aminolytica | Actinomyces bovis | Alkalilimnicola ehrlichii | Aquaspirillum polymorphum |
| Acaricomes | Acidocella facilis | Actinomyces denticolens | Alkaliphilus | Aquaspirillum |
| Acaricomes phytoseiuli | Acidomonas | Actinomyces europaeus | Alkaliphilus oremlandii | putridiconchylium |
| Acetitomaculum | Acidomonas methanolica | Actinomyces georgiae | Alkaliphilus transvaalensis | Aquaspirillum serpens |
| Acetitomaculum ruminis | Acidothermus | Actinomyces gerencseriae | Allochromatium | Aquimarina |
| Acetivibrio | Acidothermus cellulolyticus | Actinomyces hordeovulneris | Allochromatium vinosum | Aquimarina latercula |
| Acetivibrio cellulolyticus | Acidovorax | Actinomyces howellii | Alloiococcus | Arcanobacterium |
| Acetivibrio ethanolgignens | Acidovorax anthurii | Actinomyces hyovaginalis | Alloiococcus otitis | Arcanobacterium haemolyticum |
| Acetivibrio multivorans | Acidovorax caeni | Actinomyces israelii | Allokutzneria | |
| Acetoanaerobium | Acidovorax cattleyae | Actinomyces johnsonii | Allokutzneria albata | Arcanobacterium pyogenes |
| Acetoanaerobium noterae | Acidovorax citrulli | Actinomyces meyeri | Altererythrobacter | Archangium |
| Acetobacter | Acidovorax defluvii | Actinomyces naeslundii | Altererythrobacter ishigakiensis | Archangium gephyra |
| Acetobacter aceti | Acidovorax delafieldii | Actinomyces neuii | Altermonas | Arcobacter |
| Acetobacter cerevisiae | Acidovorax facilis | Actinomyces odontolyticus | Altermonas haloplanktis | Arcobacter butzleri |
| Acetobacter cibinongensis | Acidovorax konjaci | Actinomyces oris | Altermonas macleodii | Arcobacter cryaerophilus |
| Acetobacter estunensis | Acidovorax temperans | Actinomyces radingae | Alysiella | Arcobacter halophilus |
| Acetobacter fabarum | Acidovorax valerianellae | Actinomyces slackii | Alysiella crassa | Arcobacter nitrofigilis |
| Acetobacter ghanensis | Acinetobacter | | Alysiella filifomis | Arcobacter skirrowii |
| Acetobacter indonesiensis | Acinetobacter baumannii | Actinomyces turicensis | Aminobacter | Arhodomonas |
| Acetobacter lovaniensis | Acinetobacter baylyi | Actinomyces viscosus | Aminobacter aganoensis | Arhodomonas aquaeolei |
| Acetobacter malorum | Acinetobacter bouvetii | Actinoplanes | Aminobacter aminovorans | Arsenophonus |
| Acetobacter nitrogenifigens | Acinetobacter calcoaceticus | Actinoplanes auranticolor | Aminobacter niigataensis | Arsenophonus nasoniae |
| Acetobacter oeni | Acinetobacter gerneri | Actinoplanes brasiliensis | Aminobacterium | |
| Acetobacter orientalis | Acinetobacter haemolyticus | Actinoplanes consettensis | Aminobacterium mobile | Arthrobacter |
| Acetobacter orleanensis | Acinetobacter johnsonii | Actinoplanes deccanensis | Aminomonas | Arthrobacter agilis |
| Acetobacter pasteurianus | Acinetobacter junii | Actinoplanes derwentensis | Aminomonas paucivorans | Arthrobacter albus |
| Acetobacter pornorum | Acinetobacter lwoffi | Actinoplanes digitatis | Ammoniphilus | Arthrobacter aurescens |
| Acetobacter senegalensis | Acinetobacter parvus | Actinoplanes durhamensis | Ammoniphilus oxalaticus | Arthrobacter chlorophenolicus |
| Acetobacter xylinus | Acinetobacter radioresistens | Actinoplanes ferrugineus | Ammoniphilus oxalivorans | Arthrobacter citreus |
| Acetobacterium | Acinetobacter schindleri | Actinoplanes globisporus | Amphibacillus | Arthrobacter clystallopoietes |
| Acetobacterium bakii | Acinetobacter soli | Actinoplanes humidus | Amphibacillus xylanus | |
| Acetobacterium carbinolicum | Acinetobacter tandoii | | | |
| Acetobacterium dehalogenans | Acinetobacter tjernbergiae | Actinoplanes italicus | Amphritea | Arthrobacter cumminsii |
| Acetobacterium fimetarium | Acinetobacter towneri | Actinoplanes liguriensis | Amphritea balenae | Arthrobacter globiformis |
| Acetobacterium malicum | Acinetobacter ursingii | Actinoplanes lobatus | Amphritea japonica | Arthrobacter histidinolovorans |
| Acetobacterium paludosum | Acinetobacter venetianus | Actinoplanes missouriensis | Amycolatopsis | Arthrobacter ilicis |
| Acetobacterium tundrae | Acrocarpospora | Actinoplanes palleronii | Amycolatopsis alba | Arthrobacter luteus |
| Acetobacterium wieringae | Acrocarpospora corrugata | Actinoplanes philippinensis | Amycolatopsis albidoflavus | Arthrobacter methylotrophus |
| Acetobacterium woodii | Acrocarpospora | Actinoplanes rectilineatus | Amycolatopsis azurea | |

TABLE 1-continued

Example Bacteria
Optionally, the target host cells are cells of a genus or species selected from this Table
and/or the production strain cells are cells of a genus or species selected from this Table

| | | | | |
|---|---|---|---|---|
| Acetofilamentum | macrocephala | Actinoplanes regularis | Amycolatopsis coloradensis | Arthrobacter mysorens |
| Acetofilamentum rigidum | Acrocarpospora pleiomorpha | Actinoplanes | Amycolatopsis lurida | Arthrobacter nicotianae |
| Acetohalobium | Actibacter | teichomyceticus | Amycolatopsis mediterranei | Arthrobacter nicotinovorans |
| Acetohalobium arabaticum | Actibacter sediminis | Actinoplanes utahensis | Amycolatopsis rifamycinica | Arthrobacter oxydans |
| Acetomicrobium | Actinoalloteichus | Actinopolyspora | Amycolatopsis rubida | Arthrobacter pascens |
| Acetomicrobium faecale | Actinoalloteichus | Actinopolyspora halophila | Amycolatopsis sulphurea | Arthrobacter |
| Acetomicrobium flavidum | cyanogriseus | Actinopolyspora | Amycolatopsis tolypomycina | phenanthrenivorans |
| Acetonema | Actinoalloteichus | mortivallis | Anabaena | Arthrobacter |
| Acetonema longum | hymeniacidonis | Actinosynnema | Anabaena cylindrica | polychromogenes |
| Acetothermus | Actinoalloteichus spitiensis | Actinosynnema mirum | Anabaena flos-aquae | Atrhrobacter protophomiae |
| Acetothermus paucivorans | Actinobaccillus | Actinotalea | Anabaena variabilis | Arthrobacter |
| Acholeplasma | Actinobacillus capsulatus | Actinotalea fermentans | Anaeroarcus | psychrolactophilus |
| Acholeplasma axanthum | Actinobacillus delphinicola | Aerococcus | Anaeroarcus burkinensis | Arthrobacter ramosus |
| Acholeplasma brassicae | Actinobacillus hominis | Aerococcus sanguinicola | Anaerobaculum | Arthrobacter sulfonivorans |
| Acholeplasma cavigenitalium | Actinobacillus indolicus | Aerococcus urinae | Anaerobaculum mobile | Arthrobacter sulfureus |
| | | | Anaerobiospirillum | Arthrobacter uratoxydans |
| Acholeplasma equifetale | Actinobacillus lignieresii | Aerococcus urinaeequi | Anaerobiospirillum | Arthrobacter ureafaciens |
| Acholeplasma granularum | Actinobacillus minor | Aerococcus urinaehominis | succiniciproducens | Arthrobacter viscosus |
| Acholeplasma hippikon | Actinobacillus muris | Aerococcus viridans | Anaerobiospirillum thomasii | Arthrobacter woluwensis |
| Acholeplasma laidlawii | Actinobacillus | Aeromicrobium | Anaerococcus | Asaia |
| Acholeplasma modicum | pleuropneumoniae | Aeromicrobium elythreum | Anaerococcus hydrogenalis | Asaia bogorensis |
| Acholeplasma morum | Actinobacillus porcinus | Aeromonas | Anaerococcus lactolyticus | Asanoa |
| Acholeplasma multilocale | Actinobacillus rossii | Aeromonas | Anaerococcus prevotii | Asanoa ferruginea |
| Acholeplasma oculi | Actinobacillus scotiae | allosaccharophila | Anaerococcus tetradius | Asticcacaulis |
| Acholeplasma palmae | Actinobacillus seminis | Aeromonas bestiarum | Anaerococcus vaginalis | Asticcacaulis biprosthecium |
| Acholeplasma parvum | Actinobacillus succinogenes | Aeromonas caviae | | Asticcacaulis excentricus |
| Acholeplasma pleciae | Actinobaccillus suis | Aeromonas encheleia | Anaerofustis | Atopobacter |
| Acholeplasma vituli | Actinobacillus ureae | Aeromonas | Anaerofustis stercorihominis | Atopobacter phocae |
| Achromobacter | Actinobaculum | enteropelogenes | Anaeromusa | Atopobium |
| Achromobacter denitrificans | Actinobaculum massiliense | Aeromonas eucrenophila | Anaeromusa acidaminophila | Atopobium fossor |
| Achromobacter insolitus | Actinobaculum schaalii | Aeromonas ichthiosmia | Anaeromyxobacter | Atopobium minutum |
| Achromobacter piechaudii | Actinobaculum suis | Aeromonas jandaei | Anaeromyxobacter | Atopobium parvulum |
| Achromobacter ruhlandii | Actinomyces urinale | Aeromonas media | dehalogenans | Atopobium rimae |
| Achromobacter spanius | Actinocatenispora | Aeromonas popoffii | Anaerorhabdus | Atopobium vaginae |
| Acidaminobacter | Actinocatenispora rupis | Aeromonas sobria | Anaerorhabdus furcosa | Aureobacterium |
| Acidaminobacter hydrogenoformans | Actinocatenispora thailandica | Aeromonas veronii | Anaerosinus | Aureobacterium barkeri |
| Acidaminococcus | Actinocatenispora sera | Agrobacterium | Anaerosinus glycerini | Aurobacterium |
| Acidaminococcus fermentans | Actinocorallia | Agrobacterium gelatinovorum | Anaerovirgula | Aurobacterium liquefaciens |
| Acidaminococcus intestini | Actinocorallia aurantiaca | Agrococcus | Anaerovirgula multivorans | Avibacterium |
| Acidicaldus | Actinocorallia aurea | Agrococcus citreus | Ancalomicrobium | Avibacterium avium |
| Acidicaldus organivorans | Actinocorallia cavernae | Agrococcus jenensis | Ancalomicrobium adetum | Avibacterium gallinarum |
| Acidimicrobium | Actinocorallia glomerata | Agromonas | Ancylobacter | Avibacterium paragallinarum |
| Acidimicrobium ferrooxidans | Actinocorallia herbida | Agromonas oligotrophica | Ancylobacter aquaticus | Avibacterium volantium |
| | | | Aneurinibacillus | Azoarcus |
| Acidiphilium | Actinocorallia libanotica | Agromyces | Aneurinibacillus | Azoarcus indigens |
| Acidiphilium acidophilum | Actinocorallia longicatena | Agromyces fucosus | aneurinilyticus | Azoarcus tolulyticus |
| Acidiphilium angustum | Actinomadura | Agromyces hippuratus | Aneurinibacillus migulanus | Azoarcus toluvorans |
| Acidiphilium cryptum | Actinomadura alba | Agromyces luteolus | Aneurinibacillus | |
| Acidiphilium multivorum | Actinomadura atramentaria | Agromyces mediolanus | themioaerophilus | |
| Acidiphilium organovorum | Actinomadura | Agromyces ramosus | Angiococcus | Azohydromonas |
| Acidiphilium rubrum | bangladeshensis | Agromyces rhizospherae | Angiococcus disciformis | Azohydromonas australica |
| Acidisoma | Actinomadura catellatispora | Akkermansia | Angulomicrobium | Azohydromonas lata |
| Acidisoma sibiricum | Actinomadura chibensis | Akkermansia muciniphila | Angulomicrobium tetraedrale | Azomonas |
| Acidisoma tundrae | Actinomadura chokoriensis | Albidiferax | Anoxybacillus | Azomonas agilis |
| Acidisphaera | Actinomadura citrea | Albidiferax ferrireducens | Anoxybacillus pushchinoensis | Azomonas insignis |
| Acidisphaera rubrifaciens | Actinomadura coerulea | Albidovulum | Aquabacterium | Azomonas macrocytogenes |
| Acidithiobacillus | Actinomadura echinospora | Albidovulum inexpectatum | Aquabacterium commune | Azorhizobium |
| Acidithiobacillus albertensis | Actinomadura fibrosa | Alcaligenes | Aquabacterium parvum | Azorhizobium caulinodans |
| Acidithiobacillus caldus | Actinomadura formosensis | Alcaligenes denitrificans | | Azorhizophilus |
| Acidithiobacillus ferrooxidans | Actinomadura hibisca | Alcaligenes faecalis | | Azorhizophilus paspali |
| Acidithiobacillus thiooxidans | Actinomadura kijaniata | Alcanivorax | | Azospirillum |
| Acidobacterium | Actinomadura latina | Alcanivorax borkumensis | | Azospirillum brasilense |
| Acidobacterium capsulatum | Actinomadura livida | Alcanivorax jadensis | | Azospirillum halopraeferens |
| | Actinomadura | Algicola | | Azospirillum irakense |
| | luteofluorescens | Algicola bacteriolytica | | Azotobacter |
| | Actinomadura macra | Alicyclobacillus | | Azotobacter beijerinckii |
| | Actinomadura madurae | Alicyclobacillus | | Azotobacter chroococcum |
| | Actinomadura oligospora | disulfidooxidans | | Azotobacter nigricans |
| | Actinomadura pelletieri | Alicyclobacillus | | Azotobacter salinestris |
| | Actinomadura rubrobrunea | sendaiensis | | Azotobacter vinelandii |
| | Actinomadura rugatobispora | Alicyclobacillus vulcanalis | | |

TABLE 1-continued

Example Bacteria
Optionally, the target host cells are cells of a genus or species selected from this Table
and/or the production strain cells are cells of a genus or species selected from this Table

| | | | | |
|---|---|---|---|---|
| | *Actinomadura umbrina* | | | |
| | *Actinomadura verrucosospora* | *Alishewanella* | | |
| | *Actinomadura vinacea* | *Alishewanella fetalis* | | |
| | *Actinomadura viridilutea* | *Alkalibacillus* | | |
| | *Actinomadura viridis* | *Alkalibacillus haloalkaliphilus* | | |
| | *Actinomadura yumaensis* | | | |
| *Bacillus* | *Bacteroides* | *Bibersteinia* | *Borrelia* | *Brevinema* |
| [see below] | *Bacteroides caccae* | *Bibersteinia trehalosi* | *Borrelia afzelii* | *Brevinema andersonii* |
| | *Bacteroides coagulans* | *Bifidobacterium* | *Borrelia americana* | *Brevundimonas* |
| *Bacteriovorax* | *Bacteroides eggerthii* | *Bifidobacterium adolescentis* | *Borrelia burgdorferi* | *Brevundimonas alba* |
| *Bacteriovorax stolpii* | *Bacteroides fragilis* | *Bifidobacterium angulatum* | *Borrelia carolinensis* | *Brevundimonas aurantiaca* |
| | *Bacteroides galacturonicus* | *Bifidobacterium animalis* | *Borrelia coriaceae* | *Brevundimonas diminuta* |
| | *Bacteroides helcogenes* | *Bifidobacterium asteroides* | *Borrelia garinii* | *Brevundimonas intermedia* |
| | *Bacteroides ovatus* | *Bifidobacterium bifidum* | *Borrelia japonica* | *Brevundimonas subvibrioides* |
| | *Bacteroides pectinophilus* | *Bifidobacterium bourn* | *Bosea* | *Brevundimonas vancanneytii* |
| | *Bacteroides pyogenes* | *Bifidobacterium breve* | *Bosea minatitlanensis* | *Brevundimonas variabilis* |
| | *Bacteroides salyersiae* | *Bifidobacterium catenulatum* | *Bosea thiooxidans* | *Brevundimonas vesicularis* |
| | *Bacteroides stercoris* | *Bifidobacterium choerinum* | *Brachybacterium* | *Brochothrix* |
| | *Bacteroides suis* | *Bifidobacterium colyneforme* | *Brachybacterium alimentarium* | *Brochothrix campestris* |
| | *Bacteroides tectus* | *Bifidobacterium cuniculi* | | *Brochothrix thermosphacta* |
| | *Bacteroides thetaiotaomicron* | *Bifidobacterium dentium* | *Brachybacterium faecium* | |
| | *Bacteroides unifomiis* | *Bifidobacterium gallicum* | *Brachybacterium paraconglomeratum* | *Brucella* |
| | *Bacteroides ureolyticus* | *Bifidobacterium gallinarum* | | *Brucella canis* |
| | *Bacteroides vulgatus* | *Bifidobacterium indicum* | *Brachybacterium rhamnosum* | *Brucella neotomae* |
| | *Balnearium* | *Bifidobacterium longum* | *Brachybacterium tyrofermentans* | *Bryobacter* |
| | *Balnearium lithotrophicum* | *Bifidobacterium magnum*  *Bifidobacterium merycicum* | *Brachyspira* | *Biyobacter aggregatus* |
| | *Balneatrix* | | *Brachyspira alvinipulli* | *Burkholderia* |
| | *Balneatrix alpica* | | | *Burkholderia ambifaria* |
| | *Balneola* | *Bifidobacterium minimum* | *Brachyspira hyodysenteriae* | *Burkholderia andropogonis* |
| | *Balneola vulgaris* | *Bifidobacterium pseudocatenulatum* | *Brachyspira innocens* | *Burkholderia anthina* |
| | *Barnesiella* | | *Brachyspira murdochii* | *Burkholderia caledonica* |
| | *Barnesiella viscericola* | *Bifidobacterium pseudolongum* | *Brachyspira pilosicoli* | *Burkholderia caryophylli* |
| | *Bartonella* | | | *Burkholderia cenocepacia* |
| | *Bartonella alsatica* | *Bifidobacterium pullorum* | *Bradyrhizobium* | *Burkholderia cepacia* |
| | *Bartonella bacilliformis* | *Bifidobacterium ruminantium* | *Bradyrhizobium canariense* | *Burkholderia cocovenenans* |
| | *Bartonella clarridgeiae* | *Bifidobacterium saeculare* | *Bradyrhizobium elkanii* | *Burkholderia dolosa* |
| | *Bartonella doshiae* | *Bifidobacterium subtile* | *Bradyrhizobium japonicum* | *Burkholderia fungorum* |
| | *Bartonella elizabethae* | *Bifidobacterium thermophilum* | *Bradyrhizobium liaoningense* | *Burkholderia glathei* |
| | *Bartonella grahamii* | | *Brenneria* | *Burkholderia glumae* |
| | *Bartonella henselae* | *Bilophila* | *Brenneria alni* | *Burkholderia graminis* |
| | *Bartonella rochalimae* | *Bilophila wadsworthia* | *Brenneria nigrifluens* | *Burkholderia kururiensis* |
| | *Bartonella vinsonii* | *Biostraticola* | *Brenneria quercina* | *Burkholderia multivorans* |
| | *Bavariicoccus* | *Biostraticola tofi* | *Brenneria quercina* | *Burkholderia phenazinium* |
| | *Bavariicoccus seileri* | | *Brenneria salicis* | *Burkholderia plantarii* |
| | *Bdellovibrio* | *Bizionia* | *Brevibacillus* | *Burkholderia pyrrocinia* |
| | *Bdellovibrio bacteriovorus* | *Bizionia argentinensis* | *Brevibacillus agri* | *Burkholderia silvatlantica* |
| | *Bdellovibrio exovorus* | *Blastobacter* | *Brevibacillus borstelensis* | *Burkholderia stabilis* |
| | *Beggiatoa* | *Blastobacter capsulatus* | *Brevibacillus brevis* | *Burkholderia thailandensis* |
| | *Beggiatoa alba* | *Blastobacter denitrificans* | *Brevibacillus centrosporus* | *Burkholderia tropica* |
| | *Beijerinckia* | *Blastococcus* | *Brevibacillus choshinensis* | *Burkholderia unamae* |
| | *Beijerinckia derxii* | *Blastococcus aggregatus* | *Brevibacillus invocatus* | *Burkholderia vietnamiensis* |
| | *Beijerinckia fluminensis* | *Blastococcus saxobsidens* | *Brevibacillus laterosporus* | *Buttiauxella* |
| | *Beijerinckia indica* | *Blastochloris* | *Brevibacillus parabrevis* | *Buttiauxella agrestis* |
| | *Beijerinckia mobilis* | *Blastochloris viridis* | *Brevibacillus reuszeri* | *Buttiauxella brennerae* |
| | *Belliella* | *Blastomonas* | *Brevibacterium* | *Buttiauxella ferragutiae* |
| | *Belliella baltica* | *Blastomonas natatoria* | *Brevibacterium abidum* | *Buttiauxella gaviniae* |
| | *Bellilinea* | *Blastopirellula* | *Brevibacterium album* | *Buttiauxella izardii* |
| | *Bellilinea caldifistulae* | *Blastopirellula marina* | *Brevibacterium aurantiacum* | *Buttiauxella noackiae* |
| | *Belnapia* | *Blautia* | *Brevibacterium celere* | *Buttiauxella wamiboldiae* |
| | *Belnapia moabensis* | *Blautia coccoides* | *Brevibacterium epidermidis* | *Butyrivibrio* |
| | *Bergeriella* | *Blautia hansenii* | *Brevibacterium frigoritolerans* | *Butyrivibrio fibrisolvens* |
| | *Bergeriella denitrificans* | *Blautia producta* | | *Butyrivibrio hungatei* |
| | *Beutenbergia* | *Blautia wexlerae* | *Brevibacterium halotolerans* | *Butyrivibrio proteoclasticus* |
| | *Beutenbergia cavernae* | *Bogoriella* | *Brevibacterium iodinum* | |
| | | *Bogoriella caseilytica* | *Brevibacterium linens* | |
| | | *Bordetella* | *Brevibacterium lyticum* | |
| | | *Bordetella avium* | *Brevibacterium mcbrellneri* | |
| | | *Bordetella bronchiseptica* | *Brevibacterium otitidis* | |
| | | *Bordetella hinzii* | *Brevibacterium oxydans* | |
| | | *Bordetella holmesii* | *Brevibacterium paucivorans* | |
| | | *Bordetella parapertussis* | *Brevibacterium stationis* | |
| | | *Bordetella pertussis* | | |
| | | *Bordetella petrii* | | |
| | | *Bordetella trematum* | | |

TABLE 1-continued

Example Bacteria
Optionally, the target host cells are cells of a genus or species selected from this Table
and/or the production strain cells are cells of a genus or species selected from this Table

*Bacillus*

| | | | | |
|---|---|---|---|---|
| B. acidiceler | B. aminovorans | B. glucanolyticus | B. taeanensis | B. lautus |
| B. acidicola | B. amylolyticus | B. gordonae | B. tequilensis | B. lehensis |
| B. acidiproducens | B. andreesenii | B. gottheilii | B. thermantarcticus | B. lentimorbus |
| B. acidocaldarius | B. aneurinilyticus | B. graminis | B. thermoaerophilus | B. lentus |
| B. acidoterrestris | B. anthracis | B. halmapalus | B. thermoamylovorans | B. licheniformis |
| B. aeolius | B. aquimaris | B. haloalkaliphilus | B. thermocatenulatus | B. ligniniphilus |
| B. aerius | B. arenosi | B. halochares | B. thermocloacae | B. litoralis |
| B. aerophilus | B. arseniciselenatis | B. halodenitfificans | B. thermocopriae | B. locisalis |
| B. agaradhaerens | B. arsenicus | B. halodurans | B. thermodenitrificans | B. luciferensis |
| B. agri | B. aurantiacus | B. halophilus | B. thermoglucosidasius | B. luteolus |
| B. aidingensis | B. arvi | B. halosaccharovorans | B. thermolactis | B. luteus |
| B. akibai | B. aryabhattai | B. hemicellulosilyticus | B. thermoleovorans | B. macauensis |
| B. alcalophilus | B. asahii | B. hemicentroti | B. thermophilus | B. macerans |
| B. algicola | B. atrophaeus | B. herbersteinensis | B. thermoruber | B. macquariensis |
| B. alginolyticus | B. axarquiensis | B. horikoshii | B. thermosphaericus | B. macyae |
| B. alkalidiazotrophicus | B. azotofixans | B. horneckiae | B. thiaminolyticus | B. malacitensis |
| B. alkalinitrilicus | B. azotoformans | B. horti | B. thioparans | B. mannanilyticus |
| B. alkalisediminis | B. badius | B. huizhouensis | B. thuringiensis | B. marisflavi |
| B. alkalitelluris | B. barbaricus | B. humi | B. tianshenii | B. marismortui |
| B. altitudinis | B. bataviensis | B. hwajinpoensis | B. trypoxylicola | B. marmarensis |
| B. alveayuensis | B. beijingensis | B. idriensis | B. tusciae | B. massiliensis |
| B. alvei | B. benzoevorans | B. indicus | B. validus | B. megaterium |
| B. amyloliquefaciens | B. beringensis | B. infantis | B. vallismortis | B. mesonae |
| B. | B. berkeleyi | B. infernus | B. vedderi | B. methanolicus |
| a. subsp. amyloliquefaciens | B. beveridgei | B. insolitus | B. velezensis | B. methylotrophicus |
| B. a. subsp. plantarum | B. bogoriensis | B. invictae | B. vietnamensis | B. migulanus |
| | B. boroniphilus | B. iranensis | B. vireti | B. mojavensis |
| B. dipsosauri | B. borstelensis | B. isabeliae | B. vulcani | B. mucilaginosus |
| B. drentensis | B. brevis Migula | B. isronensis | B. wakoensis | B. muralis |
| B. edaphicus | B. butanolivorans | B. jeotgali | B. weihenstephanensis | B. murimartini |
| B. ehimensis | B. canaveralius | B. kaustophilus | B. xiamenensis | B. mycoides |
| B. eiseniae | B. carboniphilus | B. kobensis | B. xiaoxiensis | B. naganoensis |
| B. enclensis | B. cecembensis | B. kochii | B. zhanjiangensis | B. nanhaiensis |
| B. endophyticus | B. cellulosilyticus | B. kokeshiifomiis | B. peoriae | B. nanhaiisediminis |
| B. endoradicis | B. centrosporus | B. koreensis | B. persepolensis | B. nealsonii |
| B. farraginis | B. cereus | B. korlensis | B. persicus | B. neidei |
| B. fastidiosus | B. chagannorensis | B. kribbensis | B. pervagus | B. neizhouensis |
| B. fengqiuensis | B. chitinolyticus | B. krulwichiae | B. plakortidis | B. niabensis |
| B. firmus | B. chondroitinus | B. laevolacticus | B. pocheonensis | B. niacini |
| B. flexus | B. choshinensis | B. larvae | B. polygoni | B. novalis |
| B. foraminis | B. chungangensis | B. laterosporus | B. polymyxa | B. oceanisediminis |
| B. fordii | B. cibi | B. salexigens | B. popilliae | B. odysseyi |
| B. formosus | B. circulans | B. saliphilus | B. pseudalcalophilus | B. okhensis |
| B. fortis | B. clarkii | B. schlegelii | B. pseudofirmus | B. okuhidensis |
| B. fumarioli | B. clausii | B. sediminis | B. pseudomycoides | B. oleronius |
| B. funiculus | B. coagulans | B. selenatarsenatis | B. psychrodurans | B. olyzaecorticis |
| B. fusiformis | B. coahuilensis | B. selenitireducens | B. psychrophilus | B. oshimensis |
| B. galactophilus | B. cohnii | B. seohaeanensis | B. psychrosaccharolyticus | B. pabuli |
| B. galactosidilyticus | B. composti | B. shacheensis | B. psychrotolerans | B. pakistanensis |
| B. galliciensis | B. curdlanolyticus | B. shackletonii | B. pulvifaciens | B. pallidus |
| B. gelatini | B. cycloheptanicus | B. siamensis | B. pumilus | B. pallidus |
| B. gibsonii | B. cytotoxicus | B. silvestris | B. purgationiresistens | B. panacisoli |
| B. ginsengi | B. daliensis | B. simplex | B. pycnus | B. panaciterrae |
| B. ginsengihumi | B. decisifrondis | B. siralis | B. qingdaonensis | B. pantothenticus |
| B. ginsengisoli | B. decolorationis | B. smithii | B. qingshengii | B. parabrevis |
| B. globisporus (eg, B. | B. deserti | B. soli | B. reuszeri | B. paraflexus |
| g. subsp. Globisporus; or B. | | B. solimangrovi | B. rhizosphaerae | B. pasteurii |
| g. subsp. Marinus) | | B. solisalsi | B. rigui | B. patagoniensis |
| | | B. songklensis | B. ruris | |
| | | B. sonorensis | B. safensis | |
| | | B. sphaericus | B. salarius | |
| | | B. sporothermodurans | | |
| | | B. stearothermophilus | | |
| | | B. stratosphericus | | |
| | | B. subterraneus | | |
| | | B. subtilis (eg, B. | | |
| | | s. subsp. Inaquosorum; or B. | | |
| | | s. subsp. Spizizeni; or B. | | |
| | | s. subsp. Subtilis) | | |
| Caenimonas | Campylobacter | Cardiobacterium | Catenuloplanes | Curtobacterium |
| Caenimonas koreensis | Campylobacter coli | Cardiobacterium hominis | Catenuloplanes atrovinosus | Curtobacterium albidum |
| Caldalkalibacillus | Campylobacter concisus | Carnimonas | Catenuloplanes castaneus | |
| Caldalkalibacillus uzonensis | Campylobacter curvus | Carnimonas nigrificans | Catenuloplanes crispus | Curtobacterium citreus |
| Caldanaerobacter | Campylobacter fetus | Carnobacterium | Catenuloplanes indicus | |

TABLE 1-continued

Example Bacteria
Optionally, the target host cells are cells of a genus or species selected from this Table
and/or the production strain cells are cells of a genus or species selected from this Table

| | | | |
|---|---|---|---|
| *Caldanaerobacter subterraneus* | *Campylobacter gracilis* | *Carnobacterium* | *Catenuloplanes japonicus* |
| *Caldanaerobius* | *Campylobacter helveticus* | *alterfunditum* | *Catenuloplanes nepalensis* |
| *Caldanaerobius fijiensis* | *Campylobacter hominis* | *Carnobacterium divergens* | *Catenuloplanes niger* |
| *Caldanaerobius polysaccharolyticus* | *Campylobacter hyointestinalis* | *Carnobacterium funditum* | *Chryseobacterium* |
| | *Campylobacter jejuni* | *Carnobacterium gallinarum* | *Chlyseobacterium balustinum* |
| *Caldanaerobius zeae* | *Campylobacter lari* | *Carnobacterium maltaromaticum* | |
| | *Campylobacter mucosalis* | | |
| *Caldanaerovirga* | *Campylobacter rectus* | *Carnobacterium mobile* | *Citrobacter* |
| *Caldanaerovirga acetigignens* | *Campylobacter showae* | *Carnobacterium viridans* | *C. amalonaticus* |
| *Caldicellulosiruptor* | *Campylobacter sputorum* | *Caryophanon* | *C. braakii* |
| *Caldicellulosiruptor bescii* | *Campylobacter upsaliensis* | *Calyophanon latum* | *C. diversus* |
| *Caldicellulosiruptor kristjanssonii* | *Capnocytophaga* | *Calyophanon tenue* | *C. farmeri* |
| *Caldicellulosiruptor owensensis* | *Capnocytophaga canimorsus* | *Catellatospora* | *C. freundii* |
| | *Capnocytophaga cynodegmi* | *Catellatospora citrea* | *C. gillenii* |
| | *Capnocytophaga gingivalis* | *Catellatospora methionotrophica* | *C. koseri* |
| | *Capnocytophaga granulosa* | | *C. murliniae* |
| | *Capnocytophaga haemolytica* | *Catenococcus* | *C. pasteurii*[1] |
| | *Capnocytophaga ochracea* | *Catenococcus thiocycli* | *C. rodentium* |
| | *Capnocytophaga sputigena* | | *C. sedlakii* |
| | | | *C. werkmanii* |
| | | | *C. youngae* |
| | | | *Clostridium* (see below) |
| | | | *Coccochloris* |
| | | | *Coccochloris elabens* |
| | | | *Corynebacterium* |
| | | | *Corynebacterium flavescens* |
| | | | *Corynebacterium variabile* |

*Clostridium*
*Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarni, Clostridium algidixylanolyticum, Clostridium algifaecis, Clostridium algoriphilum, Clostridium alkalicellulosi, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium autoethanogenum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium colletant, Clostridium colicanis, Clostridium colinum, Clostridium collagenovorans, Clostridium cylindrosporum, Clostridium difficile, Clostridium diolis, Clostridium disporicum, Clostridium drakei, Clostridium durum, Clostridium estertheticum, Clostridium estertheticum estertheticum, Clostridium estertheticum laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogenifomians, Clostridium hydroxybenzoicum, Clostridium hylemonae, Clostridium jejuense, Clostridium indolis, Clostridium innocuum, Clostridium intestinale, Clostridium irregulare, Clostridium isatidis, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium litorale, Clostridium lituseburense, Clostridium ljungdahlii, Clostridium lortetii, Clostridium lundense, Clostridium magnum, Clostridium malenominatum, Clostridium mangenotii, Clostridium mayombei, Clostridium methoxybenzovorans, Clostridium methylpentosum, Clostridium neopropionicum, Clostridium nexile, Clostridium nitrophenolicum, Clostridium novyi, Clostridium oceanicum, Clostridium orbiscindens, Clostridium oroticum, Clostridium oxalicum, Clostridium papyrosolvens, Clostridium paradoxum, Clostridium paraperfringens (Alias: C. welchii), Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium pilifomie, Clostridium polysaccharolyticum, Clostridium populeti, Clostridium propionicum, Clostridium proteoclasticum, Clostridium proteolyticum, Clostridium psychrophilum, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium scatologenes, Clostridium schirmacherense, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium leptospartum, Clostridium stercorarium stercorarium, Clostridium stercorarium thermolacticum, Clostridium sticklandii, Clostridium straminisolvens, Clostridium subterminale, Clostridium sufflavum, Clostridium sulfidigenes, Clostridium symbiosum, Clostridium tagluense, Clostridium tepidiprofundi, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium villosum, Clostridium vincentii, Clostridium viride, Clostridium xylanolyticum, Clostridium xylanovorans*

TABLE 1-continued

Example Bacteria
Optionally, the target host cells are cells of a genus or species selected from this Table
and/or the production strain cells are cells of a genus or species selected from this Table

| | | | | |
|---|---|---|---|---|
| *Dactylosporangium* | *Deinococcus* | *Delftia* | *Echinicola* | |
| *Dactylosporangium aurantiacum* | *Deinococcus aerius* | *Delftia acidovorans* | *Echinicola pacifica* | |
| *Dactylosporangium fulvum* | *Deinococcus apachensis* | *Desulfovibrio* | *Echinicola vietnamensis* | |
| *Dactylosporangium matsuzakiense* | *Deinococcus aquaticus* | *Desulfovibrio desulfuricans* | | |
| *Dactylosporangium roseum* | *Deinococcus aquatilis* | *Diplococcus* | | |
| *Dactylosporangium thailandense* | *Deinococcus caeni* | *Diplococcus pneumoniae* | | |
| *Dactylosporangium vinaceum* | | | | |
| | *Deinococcus radiodurans* | | | |
| | *Deinococcus radiophilus* | | | |
| *Enterobacter* | *Enterobacter kobei* | *Faecalibacterium* | *Flavobacterium* | |
| *E. aerogenes* | *E. ludwigii* | *Faecalibacterium prausnitzii* | *Flavobacterium antarcticum* | |
| *E. amnigenus* | *E. mori* | *Fangia* | *Flavobacterium aquatile* | |
| *E. agglomerans* | *E. nimipressuralis* | *Fangia hongkongensis* | *Flavobacterium aquidurense* | |
| *E. arachidis* | *E. olyzae* | *Fastidiosipila* | | |
| *E. asburiae* | *E. pulveris* | *Fastidiosipila sanguinis* | *Flavobacterium balustinum* | |
| *E. cancerogenous* | *E. pyrinus* | *Fusobacterium* | *Flavobacterium croceum* | |
| *E. cloacae* | *E. radicincitans* | *Fusobacterium nucleatum* | *Flavobacterium cucumis* | |
| *E. cowanii* | *E. taylorae* | | *Flavobacterium daejeonense* | |
| *E. dissolvens* | *E. turicensis* | | | |
| *E. gergoviae* | *E. sakazakii* | | *Flavobacterium defluvii* | |
| | *Enterobacter soli* | | | |
| *E. helveticus* | *Enterococcus* | | *Flavobacterium degerlachei* | |
| *E. hormaechei* | *Enterococcus durans* | | *Flavobacterium denitrificans* | |
| *E. intermedius* | *Enterococcus faecalis* | | | |
| | *Enterococcus faecium* | | *Flavobacterium filum* | |
| | *Erwinia* | | *Flavobacterium flevense* | |
| | *Erwinia hapontici* | | *Flavobacterium frigidarium* | |
| | *Escherichia* | | *Flavobacterium mizutaii* | |
| | *Escherichia coli* | | | |
| | | | *Flavobacterium okeanokoites* | |
| *Gaetbulibacter* | *Haemophilus* | *Ideonella* | *Janibacter* | |
| *Gaetbulibacter saemankumensis* | *Haemophilus aegyptius* | *Ideonella azotifigens* | *Janibacter anophelis* | |
| *Gallibacterium* | *Haemophilus aphrophilus* | *Idiomarina* | *Janibacter corallicola* | |
| *Gallibacterium anatis* | *Haemophilus felis* | *Idiomarina abyssalis* | *Janibacter limosus* | |
| *Gallicola* | *Haemophilus gallinarum* | *Idiomarina baltica* | *Janibacter melonis* | |
| *Gallicola barnesae* | *Haemophilus haemolyticus* | *Idiomarina fontislapidosi* | *Janibacter terrae* | |
| *Garciella* | *Haemophilus influenzae* | *Idiomarina loihiensis* | *Jannaschia* | |
| *Garciella nitratireducens* | *Haemophilus paracuniculus* | *Idiomarina ramblicola* | *Jannaschia cystaugens* | |
| *Geobacillus* | *Haemophilus parahaemolyticus* | *Idiomarina seosinensis* | *Jannaschia helgolandensis* | |
| *Geobacillus thermoglucosidasius* | *Haemophilus parainfluenzae* | *Idiomarina zobellii* | *Jannaschia pohangensis* | |
| *Geobacillus stearothermophilus* | *Haemophilus paraphrohaemolyticus* | *Ignatzschineria* | *Jannaschia rubra* | |
| *Geobacter* | | *Ignatzschineria larvae* | | |
| *Geobacter bemidjiensis* | *Haemophilus parasuis* | | *Janthinobacterium* | |
| *Geobacter bremensis* | *Haemophilus pittmaniae* | *Ignavigranum* | *Janthinobacterium agaricidamnosum* | |
| *Geobacter chapellei* | *Hafnia* | *Ignavigranum ruoffiae* | | |
| *Geobacter grbiciae* | *Hafnia alvei* | *Ilumatobacter* | *Janthinobacterium lividum* | |
| *Geobacter hydrogenophilus* | *Hahella* | *Ilumatobacter fluminis* | *Jejuia* | |
| *Geobacter lovleyi* | *Hahella ganghwensis* | *Ilyobacter* | *Jejuia pallidilutea* | |
| *Geobacter metallireducens* | | *Ilyobacter delafieldii* | | |
| *Geobacter pelophilus* | *Halalkalibacillus* | *Ilyobacter insuetus* | *Jeotgalibacillus* | |
| *Geobacter pickeringii* | *Halalkalibacillus halophilus* | *Ilyobacter polytropus* | *Jeotgalibacillus alimentarius* | |
| *Geobacter sulfurreducens* | *Helicobacter* | *Ilyobacter tartaricus* | | |
| *Geodermatophilus* | *Helicobacter pylori* | | *Jeotgalicoccus* | |
| *Geodermatophilus obscurus* | | | *Jeotgalicoccus halotolerans* | |
| *Gluconacetobacter* | | | | |
| *Gluconacetobacter xylinus* | | | | |
| *Gordonia* | | | | |
| *Gordonia rubripertincta* | | | | |
| *Kaistia* | *Labedella* | *Listeria ivanovii* | *Micrococcus* | *Nesterenkonia* |
| *Kaistia adipata* | *Labedella gwakjiensis* | *L. marthii* | *Micrococcus luteus* | *Nesterenkonia holobia* |
| *Kaistia soli* | *Labrenzia* | *L. monocytogenes* | *Micrococcus lylae* | *Nocardia* |
| *Kangiella* | *Labrenzia aggregata* | *L. newyorkensis* | *Moraxella* | *Nocardia argentinensis* |
| *Kangiella aquimarina* | *Labrenzia alba* | *L. riparia* | *Moraxella bovis* | *Nocardia corallina* |
| *Kangiella koreensis* | *Labrenzia alexandrii* | *L. rocourtiae* | *Moraxella nonliquefaciens* | *Nocardia otitidiscaviarum* |
| | *Labrenzia marina* | *L. seeligeri* | *Moraxella osloensis* | |
| *Kerstersia* | *Labrys* | *L. weihenstephanensis* | *Nakamurella* | |
| *Kerstersia gyiorum* | *Labrys methylaminiphilus* | *L. welshimeri* | *Nakamurella multipartita* | |

TABLE 1-continued

Example Bacteria
Optionally, the target host cells are cells of a genus or species selected from this Table
and/or the production strain cells are cells of a genus or species selected from this Table

| | | | | |
|---|---|---|---|---|
| *Kiloniella* | *Labrys miyagiensis* | *Listonella* | *Nannocystis* | |
| *Kiloniella laminariae* | *Labrys monachus* | *Listonella anguillarum* | *Nannocystis pusilla* | |
| *Klebsiella* | *Labrys okinawensis* | *Macrococcus* | *Natranaerobius* | |
| *K. granulomatis* | *Labrys portucalensis* | *Macrococcus bovicus* | *Natranaerobius* | |
| *K. oxytoca* | | *Marinobacter* | *themophilus* | |
| *K. pneumoniae* | *Lactobacillus* | *Marinobacter algicola* | *Natranaerobius trueperi* | |
| *K. terrigena* | [see below] | *Marinobacter bryozoorum* | *Naxibacter* | |
| *K. variicola* | *Laceyella* | *Marinobacter flavimaris* | *Naxibacter alkalitolerans* | |
| *Kluyvera* | *Laceyella putida* | *Meiothermus* | *Neisseria* | |
| *Kluyvera ascorbata* | *Lechevalieria* | *Meiothermus ruber* | *Neisseria cinerea* | |
| *Kocuria* | *Lechevalieria* | *Methylophilus* | *Neisseria denitrificans* | |
| | *aerocolonigenes* | | | |
| *Kocuria roasea* | *Legionella* | *Methylophilus* | *Neisseria gonorrhoeae* | |
| *Kocuria varians* | [see below] | *methylotrophus* | *Neisseria lactamica* | |
| *Kurthia* | *Listeria* | *Microbacterium* | *Neisseria mucosa* | |
| *Kurthia zopfii* | *L. aquatica* | *Microbacterium* | *Neisseria sicca* | |
| | *L. booriae* | *ammoniaphilum* | *Neisseria subflava* | |
| | *L. cornellensis* | *Microbacterium arborescens* | *Neptunomonas* | |
| | *L. fleischmannii* | *Microbacterium liquefaciens* | *Neptunomonas japonica* | |
| | *L. floridensis* | *Microbacterium oxydans* | | |
| | *L. grandensis* | | | |
| | *L. grayi* | | | |
| | *L. innocua* | | | |
| *Lactobacillus* | | | | |
| *L. acetotolerans* | *L. catenaformis* | *L. mali* | *L. parakefiri* | *L. sakei* |
| *L. acidifarinae* | *L. ceti* | *L. manihotivorans* | *L. paralimentarius* | *L. salivarius* |
| *L. acidipiscis* | *L. coleohominis* | *L. mindensis* | *L. paraplantarum* | *L. sanfranciscensis* |
| *L. acidophilus* | *L. collinoides* | *L. mucosae* | *L. pentosus* | *L. satsumensis* |
| *Lactobacillus agilis* | *L. composti* | *L. murinus* | *L. perolens* | *L. secaliphilus* |
| *L. algidus* | *L. concavus* | *L. nagelii* | *L. plantarum* | *L. sharpeae* |
| *L. alimentarius* | *L. colyniformis* | *L. namurensis* | *L. pontis* | *L. siliginis* |
| *L. amylolyticus* | *L. crispatus* | *L. nantensis* | *L. protectus* | *L. spicheri* |
| *L. amylophilus* | *L. crustorum* | *L. oligofermentans* | *L. psittaci* | *L. suebicus* |
| *L. amylotrophicus* | *L. curvatus* | *L. oris* | *L. rennini* | *L. thailandensis* |
| *L. amylovorus* | *L. delbrueckii* subsp. | *L. panis* | *L. reuteri* | *L. ultunensis* |
| *L. animalis* | *bulgaricus* | *L. pantheris* | *L. rhamnosus* | *L. vaccinostercus* |
| *L. antri* | *L. delbrueckii* subsp. | *L. parabrevis* | *L. rimae* | *L. vaginalis* |
| *L. apodemi* | *delbrueckii* | *L. parabuchneri* | *L. rogosae* | *L. versmoldensis* |
| *L. aviarius* | *L. delbrueckii* subsp. *lactis* | *L. paracasei* | *L. rossiae* | *L. vini* |
| *L. bifementans* | *L. dextrinicus* | *L. paracollinoides* | *L. ruminis* | *L. vitulinus* |
| *L. brevis* | *L. diolivorans* | *L. parafarraginis* | *L. saerimneri* | *L. zeae* |
| *L. buchneri* | *L. equi* | *L. homohiochii* | *L. jensenii* | *L. zymae* |
| *L. camelliae* | *L. equigenerosi* | *L. iners* | *L. johnsonii* | *L. gastricus* |
| *L. casei* | *L. farraginis* | *L. ingluviei* | *L. kalixensis* | *L. ghanensis* |
| *L. kitasatonis* | *L. farciminis* | *L. intestinalis* | *L. kefiranofaciens* | *L. graminis* |
| *L. kunkeei* | *L. fermentum* | *L. fuchuensis* | *L. kefiri* | *L. hammesii* |
| *L. leichmannii* | *L. fomicalis* | *L. gallinarum* | *L. kimchii* | *L. hamsteri* |
| *L. lindneri* | *L. fructivorans* | *L. gasseri* | *L. helveticus* | *L. harbinensis* |
| *L. malefermentans* | *L. frumenti* | | *L. hilgardii* | *L. hayakitensis* |
| *Legionella* | | | | |
| *Legionella adelaidensis* | *Legionella drancourtii* | *Candidatus Legionella jeonii* | *Legionella quinlivanii* | |
| *Legionella anisa* | *Legionella dresdenensis* | *Legionella jordanis* | *Legionella rowbothamii* | |
| *Legionella beliardensis* | *Legionella drozanskii* | *Legionella lansingensis* | *Legionella rubrilucens* | |
| *Legionella birminghamensis* | *Legionella dumoffii* | *Legionella londiniensis* | *Legionella sainthelensi* | |
| *Legionella bozemanae* | *Legionella erythra* | *Legionella longbeachae* | *Legionella santicrucis* | |
| *Legionella brunensis* | *Legionella fairfieldensis* | *Legionella lytica* | *Legionella shakespearei* | |
| *Legionella busanensis* | *Legionella fallonii* | *Legionella maceachernii* | *Legionella spiritensis* | |
| *Legionella cardiaca* | *Legionella feeleii* | *Legionella massiliensis* | *Legionella steelei* | |
| *Legionella cherrii* | *Legionella geestiana* | *Legionella micdadei* | *Legionella steigerwaltii* | |
| *Legionella cincinnatiensis* | *Legionella genomospecies* | *Legionella monrovica* | *Legionella taurinensis* | |
| Legionella clemsonensis | *Legionella gormanii* | *Legionella moravica* | *Legionella tucsonensis* | |
| *Legionella donaldsonii* | *Legionella gratiana* | *Legionella nagasakiensis* | *Legionella tunisiensis* | |
| | *Legionella gresilensis* | *Legionella nautarum* | *Legionella wadsworthii* | |
| | *Legionella hackeliae* | *Legionella norrlandica* | *Legionella waltersii* | |
| | *Legionella impletisoli* | *Legionella oakridgensis* | *Legionella worsleiensis* | |
| | *Legionella israelensis* | *Legionella parisiensis* | *Legionella yabuuchiae* | |
| | *Legionella jamestowniensis* | *Legionella pittsburghensis* | | |
| | | *Legionella pneumophila* | | |
| | | *Legionella quateirensis* | | |
| *Oceanibulbus* | *Paenibacillus* | *Prevotella* | *Quadrisphaera* | |
| *Oceanibulbus indolifex* | *Paenibacillus* | *Prevotella albensis* | *Quadrisphaera granulorum* | |
| | *thiaminolyticus* | | | |
| *Oceanicaulis* | *Pantoea* | *Prevotella amnii* | *Quatrionicoccus* | |
| *Oceanicaulis alexandrii* | *Pantoea agglomerans* | *Prevotella bergensis* | *Quatrionicoccus* | |
| *Oceanicola* | | *Prevotella bivia* | *australiensis* | |
| *Oceanicola batsensis* | *Paracoccus* | *Prevotella brevis* | | |

TABLE 1-continued

Example Bacteria
Optionally, the target host cells are cells of a genus or species selected from this Table
and/or the production strain cells are cells of a genus or species selected from this Table

| | | | | |
|---|---|---|---|---|
| Oceanicola granulosus | Paracoccus alcaliphilus | Prevotella bryantii | Quinella | |
| Oceanicola nanhaiensis | Paucimonas | Prevotella buccae | Quinella ovalis | |
| Oceanimonas | Paucimonas lemoignei | Prevotella buccalis | | |
| Oceanimonas baumannii | Pectobacterium | Prevotella copri | Ralstonia | |
| Oceaniserpentilla | Pectobacterium aroidearum | Prevotella dentalis | Ralstonia eutropha | |
| Oceaniserpentilla haliotis | Pectobacterium atrosepticum | Prevotella denticola | Ralstonia insidiosa | |
| Oceanisphaera | Pectobacterium | Prevotella disiens | Ralstonia mannitolilytica | |
| Oceanisphaera donghaensis | betavasculorum | Prevotella histicola | Ralstonia pickettii | |
| Oceanisphaera litoralis | Pectobacterium cacticida | Prevotella intermedia | Ralstonia | |
| Oceanithermus | Pectobacterium carnegieana | Prevotella maculosa | pseudosolanacearum | |
| Oceanithermus desulfurans | Pectobacterium carotovorum | Prevotella marshii | Ralstonia syzygii | |
| Oceanithermus profundus | Pectobacterium chrysanthemi | Prevotella melaninogenica | Ralstonia solanacearum | |
| | Pectobacterium cypripedii | Prevotella micans | | |
| Oceanobacillus | Pectobacterium rhapontici | Prevotella multiformis | Ramlibacter | |
| Oceanobacillus caeni | Pectobacterium wasabiae | Prevotella nigrescens | Ramlibacter henchirensis | |
| Oceanospirillum | Planococcus | Prevotella oralis | Ramlibacter tataouinensis | |
| Oceanospirillum linum | Planococcus citreus | Prevotella oris | | |
| | Planomicrobium | Prevotella oulorum | Raoultella | |
| | Planomicrobium okeanokoites | Prevotella pallens | Raoultella ornithinolytica | |
| | Plesiomonas | Prevotella salivae | Raoultella planticola | |
| | Plesiomonas shigelloides | Prevotella stercorea | Raoultella terrigena | |
| | Proteus | Prevotella tannerae | Rathayibacter | |
| | Proteus vulgaris | Prevotella timonensis | Rathayibacter caricis | |
| | | Prevotella veroralis | Rathayibacter festucae | |
| | | Providencia | Rathayibacter iranicus | |
| | | Providencia stuartii | Rathayibacter rathayi | |
| | | Pseudomonas | Rathayibacter toxicus | |
| | | Pseudomonas aeruginosa | Rathayibacter tritici | |
| | | Pseudomonas alcaligenes | Rhodobacter | |
| | | Pseudomonas anguillispetica | Rhodobacter sphaeroides | |
| | | Pseudomonas fluorescens | Ruegeria | |
| | | Pseudoalteromonas haloplanktis | Ruegeria gelatinovorans | |
| | | Pseudomonas mendocina | | |
| | | Pseudomonas pseudoalcaligenes | | |
| | | Pseudomonas putida | | |
| | | Pseudomonas tutzeri | | |
| | | Pseudomonas syringae | | |
| | | Psychrobacter | | |
| | | Psychrobacter faecalis | | |
| | | Psychrobacter phenylpyruvicus | | |
| Saccharococcus | Sagittula | Sanguibacter | Stenotrophomonas | Tatlockia |
| Saccharococcus thermophilus | Sagittula stellata | Sanguibacter keddieii | Stenotrophomonas maltophilia | Tatlockia maceachernii |
| Saccharomonospora | Salegentibacter | Sanguibacter suarezii | | Tatlockia micdadei |
| Saccharomonospora azurea | Salegentibacter salegens | Saprospira | Streptococcus | Tenacibaculum |
| Saccharomonospora cyanea | Salimicrobium | Saprospira grandis | [also see below] | Tenacibaculum amylolyticum |
| Saccharomonospora viridis | Salimicrobium album | Sarcina | Streptomyces | Tenacibaculum discolor |
| Saccharophagus | Salinibacter | Sarcina maxima | Streptomyces achromogenes | Tenacibaculum gallaicum |
| Saccharophagus degradans | Salinibacter ruber | Sarcina ventriculi | | |
| Saccharopolyspora | Salinicoccus | Sebaldella | Streptomyces cesalbus | Tenacibaculum lutimaris |
| Saccharopolyspora elythraea | Salinicoccus alkaliphilus | Sebaldella termitidis | Streptomyces cescaepitosus | |
| Saccharopolyspora gregorii | Salinicoccus hispanicus | | Streptomyces cesdiastaticus | Tenacibaculum mesophilum |
| Saccharopolyspora hirsuta | Salinicoccus roseus | Serratia | Streptomyces cesexfoliatus | |
| Saccharopolyspora hordei | | Serratia fonticola | Streptomyces fimbriatus | |
| Saccharopolyspora rectivirgula | | Serratia marcescens | | |
| Saccharopolyspora spinosa | Salinispora | Sphaerotilus | Streptomyces fradiae | Tenacibaculum skagerrakense |
| Saccharopolyspora taberi | Salinispora arenicola | Sphaerotilus natans | Streptomyces fulvissimus | |
| Saccharothrix | Salinispora tropica | Sphingobacterium | Streptomyces griseoruber | Tepidanaerobacter |
| Saccharothrix australiensis | Salinivibrio | Sphingobacterium multivorum | Streptomyces griseus | Tepidanaerobacter syntrophicus |
| Saccharothrix coeruleofusca | Salinivibrio costicola | Staphylococcus | Streptomyces lavendulae | |
| Saccharothrix espanaensis | Salmonella | [see below] | Streptomyces phaeochromogenes | Tepidibacter |
| Saccharothrix longispora | Salmonella bongori | | | Tepidibacter |
| Saccharothrix mutabilis | Salmonella enterica | | Streptomyces themodiastaticus | Tepidibacter formicigenes |
| Saccharothrix syringae | Salmonella subterranea | | | Tepidibacter thalassicus |
| Saccharothrix tangerinus | Salmonella typhi | | Streptomyces tubercidicus | |
| Saccharothrix texasensis | | | | Thermus |
| | | | | Thermus aquaticus |

TABLE 1-continued

Example Bacteria
Optionally, the target host cells are cells of a genus or species selected from this Table
and/or the production strain cells are cells of a genus or species selected from this Table

| | | | | *Thermus filiformis* |
|---|---|---|---|---|
| | | | | *Thermus thermophilus* |

*Staphylococcus*
| | | | |
|---|---|---|---|
| *S. arlettae* | *S. equorum* | *S. microti* | *S. schleiferi* |
| *S. agnetis* | *S. felis* | *S. muscae* | *S. sciuri* |
| *S. aureus* | *S. fleurettii* | *S. nepalensis* | *S. simiae* |
| *S. auricularis* | *S. gallinarum* | *S. pasteuri* | *S. simulans* |
| *S. capitis* | *S. haemolyticus* | *S. petrasii* | *S. stepanovicii* |
| *S. caprae* | *S. hominis* | *S. pettenkoferi* | *S. succinus* |
| *S. carnosus* | *S. hyicus* | *S. piscifermentans* | *S. vitulinus* |
| *S. caseolyticus* | *S. intermedius* | *S. pseudintermedius* | *S. warneri* |
| *S. chromogenes* | *S. kloosii* | *S. pseudolugdunensis* | *S. xylosus* |
| *S. cohnii* | *S. leei* | *S. pulvereri* | |
| *S. condimenti* | *S. lentus* | *S. rostri* | |
| *S. delphini* | *S. lugdunensis* | *S. saccharolyticus* | |
| *S. devriesei* | *S. lutrae* | *S. saprophyticus* | |
| *S. epidermidis* | *S. lyticans* | | |
| | *S. massiliensis* | | |

*Streptococcus*
| | | | |
|---|---|---|---|
| Streptococcus agalactiae | Streptococcus infantarius | Streptococcus orisratti | Streptococcus themophilus |
| Streptococcus anginosus | Streptococcus iniae | Streptococcus parasanguinis | Streptococcus sanguinis |
| Streptococcus bovis | Streptococcus intermedius | Streptococcus peroris | Streptococcus sobrinus |
| Streptococcus canis | Streptococcus lactarius | Streptococcus pneumoniae | Streptococcus suis |
| Streptococcus constellatus | Streptococcus milleri | Streptococcus pseudopneumoniae | Streptococcus uberis |
| Streptococcus downei | Streptococcus mitis | Streptococcus pyogenes | Streptococcus vestibularis |
| Streptococcus dysgalactiae | Streptococcus mutans | Streptococcus ratti | Streptococcus viridans |
| Streptococcus equines | Streptococcus oralis | Streptococcus salivariu | Streptococcus zooepidemicus |
| Streptococcus faecalis | Streptococcus tigurinus | | |
| Streptococcus ferus | | | |

| | | | | |
|---|---|---|---|---|
| Uliginosibacterium | Vagococcus | Vibrio | Virgibacillus | Xanthobacter |
| | Vagococcus carniphilus | Vibrio aerogenes | Virgibacillus halodenitrificans | Xanthobacter agilis |
| Uliginosibacterium gangwonense | Vagococcus elongatus | Vibrio aestuarianus | | Xanthobacter aminoxidans |
| Ulvibacter | Vagococcus fessus | Vibrio albensis | Virgibacillus pantothenticus | |
| Ulvibacter litoralis | Vagococcus fluvialis | Vibrio alginolyticus | | Xanthobacter autotrophicus |
| Umezawaea | Vagococcus lutrae | Vibrio campbellii | Weissella | |
| Umezawaea tangerina | Vagococcus salmoninarum | Vibrio cholerae | Weissella cibaria | Xanthobacter flavus |
| Undibacterium | Variovorax | Vibrio cincinnatiensis | Weissella confusa | Xanthobacter tagetidis |
| Undibacterium pigrum | Variovorax boronicumulans | Vibrio coralliilyticus | Weissella halotolerans | Xanthobacter viscosus |
| Ureaplasma | Variovorax dokdonensis | Vibrio cyclitrophicus | Weissella hellenica | Xanthomonas |
| Ureaplasma urealyticum | Variovorax paradoxus | Vibrio diazotrophicus | Weissella kandleri | Xanthomonas albilineans |
| | Variovorax soli | Vibrio fluvialis | Weissella koreensis | |
| Ureibacillus | Veillonella | Vibrio furnissii | Weissella minor | Xanthomonas alfalfae |
| Ureibacillus composti | Veillonella atypica | Vibrio gazogenes | Weissella paramesenteroides | Xanthomonas arboricola |
| Ureibacillus suwonensis | Veillonella caviae | Vibrio halioticoli | | |
| Ureibacillus terrenus | Veillonella criceti | Vibrio harveyi | Weissella soli | Xanthomonas axonopodis |
| Ureibacillus thermophilus | Veillonella dispar | Vibrio ichthyoenteri | Weissella thailandensis | |
| Ureibacillus thermosphaericus | Veillonella montpellierensis | Vibrio mediterranei | Weissella viridescens | Xanthomonas campestris |
| | Veillonella parvula | Vibrio metschnikovii | Williamsia | |
| | Veillonella ratti | Vibrio mytili | Williamsia marianensis | Xanthomonas citri |
| | Veillonella rodentium | Vibrio natriegens | Williamsia maris | Xanthomonas codiaei |
| | Venenivibrio | Vibrio navarrensis | Williamsia serinedens | Xanthomonas cucurbitae |
| | Venenivibrio stagnispumantis | Vibrio nereis | | |
| | | Vibrio nigripulchritudo | Winogradskyella | Xanthomonas euvesicatoria |
| | Verminephrobacter | Vibrio ordalii | Winogradskyella thalassocola | |
| | Verminephrobacter eiseniae | Vibrio orientalis | | Xanthomonas fragariae |
| | | Vibrio parahaemolyticus | Wolbachia | Xanthomonas fuscans |
| | Verrucomicrobium | Vibrio pectenicida | Wolbachia persica | Xanthomonas gardneri |
| | Verrucomicrobium spinosum | Vibrio penaeicida | | Xanthomonas hortorum |
| | | Vibrio proteolyticus | Wolinella | Xanthomonas hyacinthi |
| | | Vibrio shilonii | Wolinella succinogenes | Xanthomonas perforans |
| | | Vibrio splendidus | | Xanthomonas phaseoli |
| | | Vibrio tubiashii | Zobellia | Xanthomonas pisi |
| | | Vibrio vulnificus | Zobellia galactanivorans | Xanthomonas populi |
| | | | Zobellia uliginosa | Xanthomonas theicola |
| | | | Zoogloea | Xanthomonas translucens |
| | | | Zoogloea ramigera | |
| | | | Zoogloea resiniphila | |
| | | | | Xanthomonas vesicatoria |
| | | | | Xylella |
| | | | | Xylella fastidiosa |
| | | | | Xylophilus |

TABLE 1-continued

Example Bacteria
Optionally, the target host cells are cells of a genus or species selected from this Table
and/or the production strain cells are cells of a genus or species selected from this Table

| | | | | |
|---|---|---|---|---|
| | | | | *Xylophilus ampelinus* |
| *Xenophilus* | *Yangia* | *Yersinia mollaretii* | *Zooshikella* | *Zobellella* |
| *Xenophilus azovorans* | *Yangia pacifica* | *Yersinia philomiragia* | *Zooshikella ganghwensis* | *Zobellella denitrificans* |
| *Xenorhabdus* | *Yaniella* | *Yersinia pestis* | *Zunongwangia* | *Zobellella taiwanensis* |
| *Xenorhabdus beddingii* | *Yaniella flava* | *Yersinia pseudotuberculosis* | *Zunongwangia profunda* | |
| *Xenorhabdus bovienii* | *Yaniella halotolerans* | *Yersinia rohdei* | *Zymobacter* | *Zeaxanthinibacter* |
| *Xenorhabdus cabanillasii* | *Yeosuana* | *Yersinia ruckeri* | *Zymobacter palmae* | *Zeaxanthinibacter enoshimensis* |
| *Xenorhabdus doucetiae* | *Yeosuana aromativorans* | *Yokenella* | *Zymomonas* | *Zhihengliuella* |
| *Xenorhabdus griffiniae* | *Yersinia* | *Yokenella regensburgei* | *Zymomonas mobilis* | *Zhihengliuella halotolerans* |
| *Xenorhabdus hominickii* | *Yersinia aldovae* | *Yonghaparkia* | *Zymophilus* | *Xylanibacterium* |
| *Xenorhabdus koppenhoeferi* | *Yersinia bercovieri* | *Yonghaparkia alkaliphila* | *Zymophilus paucivorans* | *Xylanibacterium ulmi* |
| *Xenorhabdus nematophila* | *Yersinia enterocolitica* | *Zavarzinia* | *Zymophilus raffinosivorans* | |
| *Xenorhabdus poinarii* | *Yersinia entomophaga* | *Zavarzinia compransoris* | | |
| *Xylanibacter* | *Yersinia frederiksenii* | | | |
| *Xylanibacter olyzae* | *Yersinia intermedia* | | | |
| | *Yersinia kristensenii* | | | |

TABLE 2

Sequences
Nucleic acid sequences herein are written in 5'
to 3' direction; amino acid sequences are
written in N- to C-terminal direction.

SEQ ID NO: 1 (P10)
TTTCAATTTAATCATCCGGCTCGTATAATGTGTGGA

SEQ ID NO: 2 (BCD14)
GGGCCCAAGTTCACTTAAAAAGGAGATCAACAATGAAAGCAATTTTCGTA
CTGAAACATCTTAATCATGCGGTGGAGGGTTTCTAATG

SEQ ID NO: 3 (gfp)
ATGAGCAAAGGAGAAGAACTTTTCACTGGAGTTGTC

SEQ IDs NO: 4 & 29 (example Expression Operating
Unit, EOU)
The EOU is (in 5' to 3' direction):-
[SEQ ID NO: 4]-[promoter]-[TIS]-[GFP-encoding
nucleotide sequence]-[SEQ ID NO: 29]
Where
SEQ ID NO: 4 is
GAATTCAAAAGATCTTAAGTAAGTAAGAGTATACGTATATCGGCTAATAA
CGTATTAAGGCGCTTCGGCGCCTTTTTTTTATGGGGGTATTTTCATCCCAA
TCCACACGTCCAACGCACAGCAAACACCACGTCGACCCTATCAGCTGCGT
GCTTTCTATGAGTCGTTGCTGCATAACTTGACAATTAATCATCCGGCTCG
TATAATGTGTGGAA SEQ ID NO: 29 is
GGATCCAAACTCGAGTAAGGATCTCCAGGCATCAAATAAAACGAAAGGCT
CAGTCGAAAGACTGGGCCTTTCGTTTTATCTGTTGTTTGTCGGTGAACGC
TCTCTACTAGAGTCACACTGGCTCACCTTCGGGTGGGCCTTTCTGCGTTT
ATA SEQ ID NO: 5 (Example Shine Dalgarno Sequence)
AAAGAGGAGAAA SEQ ID NO: 26 (Spacer sequence)
CTTTGCCGCGCGCTTCGTCACGTAATTCTCGTCGCAA SEQ ID NO: 27 (Spacer sequence)
GTTTGGCGATGGCGCGGGTGTGGTTGTGCTTCGGCGT SEQ ID NO: 28 (Spacer sequence)
TGGGATGCCTACCGCAAGCAGCTTGGCCTGAA

TABLE 3

Anderson Promoter Collection

| SEQ ID NO: | Identifier | Sequence[a] | Measured Strength[b] |
|---|---|---|---|
| 6 | BBa J23119 | TTGACAGCTAGCTCAGTCCTAGGTA TAATGCTAGC | n/a |
| 7 | BBa J23100 | TTGACGGCTAGCTCAGTCCTAGGTA CAGTGCTAGC | 1 |
| 8 | BBa J23101 | TTTACAGCTAGCTCAGTCCTAGGTA TTATGCTAGC | 0.7 |
| 9 | BBa J23102 | TTGACAGCTAGCTCAGTCCTAGGTA CTGTGCTAGC | 0.86 |
| 10 | BBa J23103 | CTGATAGCTAGCTCAGTCCTAGGGA TTATGCTAGC | 0.01 |
| 11 | BBa J23104 | TTGACAGCTAGCTCAGTCCTAGGTA TTGTGCTAGC | 0.72 |
| 12 | BBa J23105 | TTTACGGCTAGCTCAGTCCTAGGTA CTATGCTAGC | 0.24 |
| 13 | BBa J23106 | TTTACGGCTAGCTCAGTCCTAGGTA TAGTGCTAGC | 0.47 |
| 14 | BBa J23107 | TTTACGGCTAGCTCAGCCCTAGGTA TTATGCTAGC | 0.36 |
| 15 | BBa J23108 | CTGACAGCTAGCTCAGTCCTAGGTA TAATGCTAGC | 0.51 |
| 16 | BBa J23109 | TTTACAGCTAGCTCAGTCCTAGGGA CTGTGCTAGC | 0.04 |
| 17 | BB3 J23110 | TTTACGGCTAGCTCAGTCCTAGGTA CAATGCTAGC | 0.33 |
| 18 | BBa J23111 | TTGACGGCTAGCTCAGTCCTAGGTA TAGTGCTAGC | 0.58 |
| 19 | BBa J23112 | CTGATAGCTAGCTCAGTCCTAGGGA TTATGCTAGC | 0 |
| 20 | BBa J23113 | CTGATGGCTAGCTCAGTCCTAGGGA TTATGCTAGC | 0.01 |
| 21 | BBa J23114 | TTTATGGCTAGCTCAGTCCTAGGTA CAATGCTAGC | 0.1 |

TABLE 3-continued

Anderson Promoter Collection

| SEQ ID NO: | Identifier | Sequence[a] | Measured Strength[b] |
|---|---|---|---|
| 22 | BBa J23115 | TTTATAGCTAGCTCAGCCCTTGGTA CAATGCTAGC | 0.15 |
| 23 | BBa J23116 | TTGACAGCTAGCTCAGTCCTAGGGA CTATGCTAGC | 0.16 |
| 24 | BBa J23117 | TTGACAGCTAGCTCAGTCCTAGGGA TTGTGCTAGC | 0.06 |
| 25 | BBa J23118 | TTGACGGCTAGCTCAGTCCTAGGTA TTGTGCTAGC | 0.56 |

[a]also shown in the Anderson Catalog, see parts.igem.org/Promoters/Catalog/Anderson
[b]Strength is the Anderson Score (AS), e.g., a strength of 1 is a AS of 1. Reported activities of the promoters are given as the relative fluorescence of plasmids in strain TG1 grown in LB media to saturation. A suitable plasmid is EX-Ptet-S-rbsRFP-P/RFP reporter/ as described at parts.igem.org/Part:BBa_J61002; insertion of a promoter element between XbaI and SpeI sites results in a RFP reporter.

The invention claimed is:

1. A cell of a production strain of *Escherichia coli* (*E. coli*) cells, comprising a first DNA construct wherein:

the first DNA construct comprises a nucleotide sequence encoding a Cas nuclease, wherein the nucleotide sequence is under the control of a promoter for controlling the expression of the Cas nuclease in the production strain cell, wherein the first DNA construct comprises an origin of replication that is operable in the cell for replication of the construct;

the promoter comprises a nucleotide sequence that is capable of binding to a repressor;

wherein the production strain cell comprises a nucleic acid encoding the repressor;

wherein the promoter is capable of being repressed by the repressor in the production strain;

wherein the cell of the production strain comprises amplified copies of the first DNA construct, wherein the amplified copies of the first DNA construct do not comprise the nucleic acid encoding the repressor, wherein the nucleic acid encoding the repressor is a chromosomally-integrated sequence or comprised by a second DNA construct; and wherein the nucleic acid encoding the repressor is capable of expressing the repressor in the cell of the production strain comprising the amplified copies of the first DNA construct;

wherein the cell of the production strain comprises a nucleotide sequence whose expression is inducible to produce phage coat proteins in the cell of the production strain, wherein the cell of the production strain is capable of packaging the amplified copies of the first DNA construct into phage particles or non-self-replicative transduction particles for introducing the first DNA into a target host cell, and wherein the phage particles or non-self-replicative transduction particles are devoid of a nucleotide sequence encoding the repressor; and wherein the Cas nuclease is operable with one or more crRNAs or gRNAs to cut target nucleotide sequences in the target host cell, and wherein the production strain cell does not comprise a crRNA or gRNA operable with the Cas nuclease to target and cut a chromosomal sequence of the production strain cell.

2. The cell of claim 1, wherein the nucleotide sequence that is capable of binding to the repressor is a tetO or lacO.

3. The cell of claim 2, wherein the promoter is $P_{LtetO-1}$, $P_{Llaco-1}$, or a repressible homologue thereof.

4. The cell of claim 1, wherein the repressor is a tetracycline repressor (TetR) or a lac repressor (LacR).

5. The cell of claim 1, wherein the nucleic acid encoding the repressor is a chromosomally-integrated sequence.

6. The cell of claim 1, wherein the nucleic acid encoding the repressor is a sequence comprised by an episome.

7. The cell of claim 1, wherein the first DNA construct is a plasmid or phagemid.

8. The cell of claim 7, wherein the first DNA construct is a high copy number plasmid or phagemid.

9. The cell of claim 1, wherein the promoter for controlling the expression of the Cas nuclease in the production strain cell combined with a translation initiation site (TIS) is capable of producing expression of green fluorescent protein (GFP) from a first expression operating unit (EOU) in E. coli strain BW25113 cells with a fluorescence of from 0.5 to 4 times the fluorescence produced in E. coli strain BW25113 cells using a second EOU comprising a P10 promoter having a sequence of SEQ ID NO: 1 combined with a BCD14 TIS having a sequence of SEQ ID NO: 2, wherein the EOUs differ only in their promoter and TIS combinations, wherein each EOU comprises in 5' to 3' direction an upstream initiator, the respective promoter, the respective TIS, a nucleotide sequence encoding GFP, a 3' UTR, a transcription terminator and a downstream insulator.

10. The cell of claim 9, wherein fluorescence using the first EOU is 0.5 to 2 times the fluorescence using the second EOU.

11. The cell of claim 1, wherein the cell is capable of growth and propagation sufficient to produce at least 1000 copies of the first DNA construct.

12. The cell of claim 1, wherein at least $10^5$ copies of the first DNA construct can be produced per $10^3$ cells of the production strain.

13. The cell of claim 1, wherein a cell of the production strain is capable of at least 2 or 3 logs of expansion when the first DNA construct is comprised therein.

14. The cell of claim 1, wherein the Cas nuclease is a Type I Cas nuclease.

15. The cell of claim 1, wherein the Cas nuclease is a Cas3 nuclease.

16. The cell of claim 15, wherein the first DNA construct or the cell encodes Cascade proteins that are cognate with the Cas3 nuclease.

17. The cell of claim 1, wherein the Cas nuclease is a Cas9 nuclease.

18. The cell of claim 1, wherein the Cas nuclease is a Cpf1 nuclease.

19. The cell of claim 1, wherein the first DNA construct comprises one or more nucleotide sequences for producing crRNAs or gRNAs that are operable with the Cas nuclease to cut target nucleotide sequences in the target host cell.

20. The cell of claim 1, wherein the target host cell is comprised by a gut microbiota.

21. The cell of claim 1, wherein the target host cell is selected from the group consisting of a C. difficile, P. aeruginosa, K. pneumoniae, E. coli, H. pylori, S. pneumoniae and S. aureus cell.

\* \* \* \* \*

SEQUENCE LISTING

```
<160> NUMBER OF SEQ ID NOS: 29

<210> SEQ ID NO 1
<211> LENGTH: 36
<212> TYPE: DNA
<213> ORGANISM: Artificial Sequence
<220> FEATURE:
<223> OTHER INFORMATION: Synthetic Construct

<400> SEQUENCE: 1
tttcaattta atcatccggc tcgtataatg tgtgga                              36

<210> SEQ ID NO 2
<211> LENGTH: 88
<212> TYPE: DNA
<213> ORGANISM: Artificial Sequence
<220> FEATURE:
<223> OTHER INFORMATION: Synthetic Construct

<400> SEQUENCE: 2
gggcccaagt tcacttaaaa aggagatcaa caatgaaagc aatttcgta ctgaaacatc     60 ttaatcatgc ggtggagggt ttctaatg                                       88

<210> SEQ ID NO 3
<211> LENGTH: 36
<212> TYPE: DNA
<213> ORGANISM: Artificial Sequence
<220> FEATURE:
<223> OTHER INFORMATION: Synthetic Construct

<400> SEQUENCE: 3
atgagcaaag gagaagaact tttcactgga gttgtc                              36

<210> SEQ ID NO 4
<211> LENGTH: 214
<212> TYPE: DNA
<213> ORGANISM: Artificial Sequence
<220> FEATURE:
<223> OTHER INFORMATION: Synthetic Construct

<400> SEQUENCE: 4
gaattcaaaa gatcttaagt aagtaagagt atacgtatat cggctaataa cgtattaagg    60
cgcttcggcg ccttttttta tgggggtatt ttcatcccaa tccacacgtc caacgcacag   120
caaacaccac gtcgaccta tcagctgcgt gctttctatg agtcgttgct gcataacttg    180
acaattaatc atccggctcg tataatgtgt ggaa                               214
```

<210> SEQ ID NO 5
<211> LENGTH: 12
<212> TYPE: DNA
<213> ORGANISM: Artificial Sequence
<220> FEATURE:
<223> OTHER INFORMATION: Synthetic Construct

<400> SEQUENCE: 5
aaagaggaga aa                                                          12

<210> SEQ ID NO 6
<211> LENGTH: 35
<212> TYPE: DNA
<213> ORGANISM: Artificial Sequence
<220> FEATURE:
<223> OTHER INFORMATION: Synthetic Construct

<400> SEQUENCE: 6
ttgacagcta gctcagtcct aggtataatg ctagc                                 35

<210> SEQ ID NO 7
<211> LENGTH: 35
<212> TYPE: DNA
<213> ORGANISM: Artificial Sequence
<220> FEATURE:
<223> OTHER INFORMATION: Synthetic Construct

<400> SEQUENCE: 7
ttgacggcta gctcagtcct aggtacagtg ctagc                                 35

<210> SEQ ID NO 8
<211> LENGTH: 35
<212> TYPE: DNA
<213> ORGANISM: Artificial Sequence
<220> FEATURE:
<223> OTHER INFORMATION: Synthetic Construct

<400> SEQUENCE: 8
tttacagcta gctcagtcct aggtattatg ctagc                                 35

<210> SEQ ID NO 9
<211> LENGTH: 35
<212> TYPE: DNA
<213> ORGANISM: Artificial Sequence
<220> FEATURE:
<223> OTHER INFORMATION: Synthetic Construct

<400> SEQUENCE: 9
ttgacagcta gctcagtcct aggtactgtg ctagc                                 35

<210> SEQ ID NO 10
<211> LENGTH: 35
<212> TYPE: DNA
<213> ORGANISM: Artificial Sequence
<220> FEATURE:
<223> OTHER INFORMATION: Synthetic Construct

<400> SEQUENCE: 10
ctgatagcta gctcagtcct agggattatg ctagc                                 35

<210> SEQ ID NO 11
<211> LENGTH: 35
<212> TYPE: DNA
<213> ORGANISM: Artificial Sequence
<220> FEATURE:
<223> OTHER INFORMATION: Synthetic Construct -continued

```
<400> SEQUENCE: 11
ttgacagcta gctcagtcct aggtattgtg ctagc                                    35

<210> SEQ ID NO 12
<211> LENGTH: 35
<212> TYPE: DNA
<213> ORGANISM: Artificial Sequence
<220> FEATURE:
<223> OTHER INFORMATION: Synthetic Construct

<400> SEQUENCE: 12
tttacggcta gctcagtcct aggtactatg ctagc                                    35

<210> SEQ ID NO 13
<211> LENGTH: 35
<212> TYPE: DNA
<213> ORGANISM: Artificial Sequence
<220> FEATURE:
<223> OTHER INFORMATION: Synthetic Construct

<400> SEQUENCE: 13
tttacggcta gctcagtcct aggtatagtg ctagc                                    35

<210> SEQ ID NO 14
<211> LENGTH: 35
<212> TYPE: DNA
<213> ORGANISM: Artificial Sequence
<220> FEATURE:
<223> OTHER INFORMATION: Synthetic Construct

<400> SEQUENCE: 14
tttacggcta gctcagccct aggtattatg ctagc                                    35

<210> SEQ ID NO 15
<211> LENGTH: 35
<212> TYPE: DNA
<213> ORGANISM: Artificial Sequence
<220> FEATURE:
<223> OTHER INFORMATION: Synthetic Construct

<400> SEQUENCE: 15
ctgacagcta gctcagtcct aggtataatg ctagc                                    35

<210> SEQ ID NO 16
<211> LENGTH: 35
<212> TYPE: DNA
<213> ORGANISM: Artificial Sequence
<220> FEATURE:
<223> OTHER INFORMATION: Synthetic Construct

<400> SEQUENCE: 16
tttacagcta gctcagtcct agggactgtg ctagc                                    35

<210> SEQ ID NO 17
<211> LENGTH: 35
<212> TYPE: DNA
<213> ORGANISM: Artificial Sequence
<220> FEATURE:
<223> OTHER INFORMATION: Synthetic Construct

<400> SEQUENCE: 17
tttacggcta gctcagtcct aggtacaatg ctagc                                    35

<210> SEQ ID NO 18
```

```
<211> LENGTH: 35
<212> TYPE: DNA
<213> ORGANISM: Artificial Sequence
<220> FEATURE:
<223> OTHER INFORMATION: Synthetic Construct

<400> SEQUENCE: 18
ttgacggcta gctcagtcct aggtatagtg ctagc                             35

<210> SEQ ID NO 19
<211> LENGTH: 35
<212> TYPE: DNA
<213> ORGANISM: Artificial Sequence
<220> FEATURE:
<223> OTHER INFORMATION: Synthetic Construct

<400> SEQUENCE: 19
ctgatagcta gctcagtcct agggattatg ctagc                             35

<210> SEQ ID NO 20
<211> LENGTH: 35
<212> TYPE: DNA
<213> ORGANISM: Artificial Sequence
<220> FEATURE:
<223> OTHER INFORMATION: Synthetic Construct

<400> SEQUENCE: 20
ctgatggcta gctcagtcct agggattatg ctagc                             35

<210> SEQ ID NO 21
<211> LENGTH: 35
<212> TYPE: DNA
<213> ORGANISM: Artificial Sequence
<220> FEATURE:
<223> OTHER INFORMATION: Synthetic Construct

<400> SEQUENCE: 21
tttatggcta gctcagtcct aggtacaatg ctagc                             35

<210> SEQ ID NO 22
<211> LENGTH: 35
<212> TYPE: DNA
<213> ORGANISM: Artificial Sequence
<220> FEATURE:
<223> OTHER INFORMATION: Synthetic Construct

<400> SEQUENCE: 22
tttatagcta gctcagccct tggtacaatg ctagc                             35

<210> SEQ ID NO 23
<211> LENGTH: 35
<212> TYPE: DNA
<213> ORGANISM: Artificial Sequence
<220> FEATURE:
<223> OTHER INFORMATION: Synthetic Construct

<400> SEQUENCE: 23
ttgacagcta gctcagtcct agggactatg ctagc                             35

<210> SEQ ID NO 24
<211> LENGTH: 35
<212> TYPE: DNA
<213> ORGANISM: Artificial Sequence
<220> FEATURE:
<223> OTHER INFORMATION: Synthetic Construct
```

```
<400> SEQUENCE: 24
ttgacagcta gctcagtcct agggattgtg ctagc                                35

<210> SEQ ID NO 25
<211> LENGTH: 35
<212> TYPE: DNA
<213> ORGANISM: Artificial Sequence
<220> FEATURE:
<223> OTHER INFORMATION: Synthetic Construct

<400> SEQUENCE: 25
ttgacggcta gctcagtcct aggtattgtg ctagc                                35

<210> SEQ ID NO 26
<211> LENGTH: 37
<212> TYPE: DNA
<213> ORGANISM: Artificial Sequence
<220> FEATURE:
<223> OTHER INFORMATION: Synthetic Construct

<400> SEQUENCE: 26
ctttgccgcg cgcttcgtca cgtaattctc gtcgcaa                              37

<210> SEQ ID NO 27
<211> LENGTH: 37
<212> TYPE: DNA
<213> ORGANISM: Artificial Sequence
<220> FEATURE:
<223> OTHER INFORMATION: Synthetic Construct

<400> SEQUENCE: 27
gtttggcgat ggcgcgggtg tggttgtgct tcggcgt                              37

<210> SEQ ID NO 28
<211> LENGTH: 32
<212> TYPE: DNA
<213> ORGANISM: Artificial Sequence
<220> FEATURE:
<223> OTHER INFORMATION: Synthetic Construct

<400> SEQUENCE: 28
tgggatgcct accgcaagca gcttggcctg aa                                   32

<210> SEQ ID NO 29
<211> LENGTH: 153
<212> TYPE: DNA
<213> ORGANISM: Artificial Sequence
<220> FEATURE:
<223> OTHER INFORMATION: Synthetic Construct

<400> SEQUENCE: 29
ggatccaaac tcgagtaagg atctccaggc atcaaataaa acgaaaggct cagtcgaaag     60
actgggcctt tcgttttatc tgttgtttgt cggtgaacgc tctctactag agtcacactg    120
gctcaccttc gggtgggcct ttctgcgttt ata                                 153
```